(12) United States Patent
Valentino et al.

(10) Patent No.: US 10,420,826 B2
(45) Date of Patent: Sep. 24, 2019

(54) CONJUNCTIVITIS VACCINES

(71) Applicant: Massachusetts Eye & Ear Infirmary, Boston, MA (US)

(72) Inventors: Michael Valentino, Boston, MA (US); Michael S. Gilmore, Boston, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 12 days.

(21) Appl. No.: 15/524,576

(22) PCT Filed: Nov. 10, 2015

(86) PCT No.: PCT/US2015/060009
§ 371 (c)(1),
(2) Date: May 4, 2017

(87) PCT Pub. No.: WO2016/077382
PCT Pub. Date: May 19, 2016

(65) Prior Publication Data
US 2018/0271968 A1    Sep. 27, 2018

Related U.S. Application Data

(60) Provisional application No. 62/078,357, filed on Nov. 11, 2014.

(51) Int. Cl.
*C07K 14/315* (2006.01)
*A61K 39/09* (2006.01)

(52) U.S. Cl.
CPC ........ *A61K 39/092* (2013.01); *C07K 14/3156* (2013.01)

(58) Field of Classification Search
None
See application file for complete search history.

(56) References Cited

U.S. PATENT DOCUMENTS 7,939,087 B2 * 5/2011 Telford ................ C07K 14/315
424/244.1

OTHER PUBLICATIONS (CDC), C. f. D. C. a. P. "Outbreak of bacterial conjunctivitis at a college—New Hampshire," MMWR Morb Mortal Wkly Rep, 2002, 51: 205-207.
(CDC), C. f. D. C. a. P. "Pneumococcal conjunctivitis at an elementary school—Maine," MMWR Morb Mortal Wkly Rep, 2003, 52(4): 64-66.
Aziz et al., "The Rast Server: rapid annotations using subsystems technology," BMC Genomics, 2008, 9(75): 1-15.
Bagnoli et al., "A second pilus type in *Streptococcus pneumoniae* is prevalent in emerging serotypes and mediates adhesion to host cells," J Bacteriol, 2008, 190(15): 5480-5492.

Brady et al., "The changing faces of *Streptococcus* antigen I/II polypeptide family adhesins," Mol Microbiol, 2010, 77(2): 276-286.
Brown et al., "A locus contained within a variable region of pneumococcal pathogenicity island 1 contributes to virulence in mice," Infect Immun, 2004, 72(3): 1587-1593.
Buck et al., "A community outbreak of conjunctivitis caused by nontypeable *Streptococcus pneumoniae* in Minnesota," Pediatr Infect Dis J, 2006, 25(10): 906-911.
Buznach et al., "Clinical and bacterial characteristics of acute bacterial conjunctivitis in children in the antibiotic resistance era," Pediatr Infect Dis J, 2005, 24(9): 823-828.
Carrolo et al., "Prophage spontaneous activation promotes DNA release enhancing biofilm formation in *Streptococcus pneumonia*," PLoS One, 2010, 5(12): e15678, 1-10.
Chewapreecha et al., "Dense genomic sampling identifies highways of pneumococcal recombination," Nat Genet, 2014, 46(3): 305-309.
Corander et al., "BAPS 2: enhanced possibilities for the analysis of genetic population structure," Bioinformatics, 2004, 20(15): 2363-2369.
Croucher et al., "Population genomics of post-vaccine changes in pneumococcal epidemiology," Nat Genet, 2013, 45(6): 656-663.
Croucher et al., "Rapid pneumococcal evolution in response to clinical interventions," Science, 2011, 331: 430-434.
Crum et al., "An outbreak of conjunctivitis due to a novel unencapsulated *Streptococcus pneumoniae* among military trainees," Clin Infect Dis 39: 1148-1154, 2004.
Delcher et al., "Improved microbial gene identification with GLIMMER," Nucleic Acids Res, 1999, 27(23): 4636-4641.
Donati et al., "Structure and dynamics of the pan-genome of *Streptococcus pneumoniae* and closely related species," Genome Biol, 2010, 11: R107, 1-19.
Enright et al., "A multilocus sequence typing scheme for *Streptococcus pneumoniae*: identification of clones associated with serious invasive disease," Microbiology, 1998, 144 ( Pt 11), 3049-3060.
Fagan et al., "Identification and characterization of a novel secreted immunoglobulin binding protein from group A *Streptococcus*," Infect Immun, 2001, 69(8): 4851-4857.
Farrell et al., "Increased antimicrobial resistance among nonvaccine serotypes of *Streptococcus pneumoniae* in the pediatric population after the introduction of 7-valent pneumococcal vaccine in the United States," Pediatr Infect Dis J, 2007, 26(2): 123-128.
Finn et al., "The Pfam protein families database," Nucleic Acids Res, 2008, 36: D281-288.
Frost et al., "Mobile genetic elements: the agents of open source evolution," Nat Rev Microbiol, 2005, 3: 722-732.
Gosink et al., "Role of novel choline binding proteins in virulence of *Streptococcus pneumonia*," Infect Immun, 2000, 68(10): 5690-5695.
Govindarajan et al., "A metalloproteinase secreted by *Streptococcus pneumoniae* removes membrane mucin MUC16 from the epithelial glycocalyx barrier," PLoS One, 2012, 7(3): e32418, 1-12.
Guindon et al., "New algorithms and methods to estimate maximum-likelihood phylogenies: assessing the performance of PhyML 3.0.," Syst Biol, 2010, 59(3): 307-321.
Haas et al., "High proportion of nontypeable *Streptococcus pneumoniae* isolates among sporadic, nonoutbreak cases of bacterial conjunctivitis," Curr Eye Res 36(12): 1078-1085, 2011.

(Continued)

*Primary Examiner* — Oluwatosin A Ogunbiyi
(74) *Attorney, Agent, or Firm* — Fish & Richardson P.C.

(57) ABSTRACT

Compositions comprising antigenic peptides, and their use in inducing an immunoprotective response in a subject against an infection with *Streptococcus pneumonia*, or for treating or preventing, i.e., reducing risk of, an infection of *Streptococcus pneumonia*.

14 Claims, 17 Drawing Sheets

Specification includes a Sequence Listing.

(56) References Cited

OTHER PUBLICATIONS

Haas et al., "Microbiological etiology and susceptibility of bacterial conjunctivitis isolates from clinical trials with ophthalmic, twice-daily besifloxacin," Adv Ther, 2012, 29(5): 442-455.

Hanage et al., "A successful, diverse disease-associated lineage of nontypeable pneumococci that has lost the capsular biosynthesis locus," J. Clin. Microbiol, 2006, 44(3): 743-749.

Hazlett et al., "In vivo identification of sialic acid as the ocular receptor for Pseudomonas aeruginosa," Infect Immun, 1986, 51(2): 687-689.

Hilleringmann et al., "Molecular architecture of *Streptococcus pneumoniae* TIGR4 pili," Embo J, 2009, 28: 3921-3930.

International Search Report and Written Opinion in International Application No. PCT/US2015/060009, dated Jul. 4, 2016, 26 pages.

Isnard et al., "Studies on corneal wound healing. Effect of fucose on iodine vapor-burnt rabbit corneas," Ophthalmologica, 2005, 219: 324-333.

Jakubovics et al., "Differential binding specificities of oral streptococcal antigen I/II family adhesins for human or bacterial ligands," Mol Microbiol, 2005, 55(5): 1591-1605.

Jerlstrom et al., "Identification of an immunoglobulin A binding motif located in the beta-antigen of the c protein complex of group B streptococci," Infect Immun, 1996, 64(7): 2787-2793.

Jerlstrom et al., "The IgA-binding beta antigen of the c protein complex of Group B streptococci: sequence determination of its gene and detection of two binding regions," Mol Microbiol, 1991, 5(4): 843-849.

Jumblatt et al., "Glycoprotein 340 in normal human ocular surface tissues and tear film," Infect Immun, 2006, 74(4): 4058-4063.

Karpecki et al., "Besifloxacin ophthalmic suspension 0.6% in patients with bacterial conjunctivitis: A multicenter, prospective, randomized, double-masked, vehicle-controlled, 5-day efficacy and safety study," Clin Ther, 2009, 31(3): 514-526.

Keller et al., "Draft Genome Sequences of Five Multilocus Sequence Types of Nonencapsulated *Streptococcus pneumonia*," Genome Announc, 2013, 1(4): e00520-13, 2 pages.

Keller et al., "PspK of *Streptococcus pneumoniae* increases adherence to epithelial cells and enhances nasopharyngeal colonization," Infect Immun, 2013, 81(1): 173-181.

Kim et al., "Recurrent infections and immune evasion strategies of *Staphylococcus aureus*," Curr Opin Microbiol, 2012, 15(1): 92-99.

Konstantinidis et al., "Genomic insights that advance the species definition for prokaryotes," PNAS, 2005, 102(7): 2567-2572.

Konstantinidis et al., "The bacterial species definition in the genomic era," Philos Trans R Soc Lond B Biol Sci, 2006, 361: 1929-1940.

Lebreton et al., "Emergence of epidemic multidrug-resistant Enterococcus faecium from animal and commensal strains," MBio, 2013, 4(4): e00534-13, 1-10.

Li et al., "OrthoMCL: identification of ortholog groups for eukaryotic genomes," Genome Res, 2003, 13: 2178-2189.

Lofling et al., "Cellular interactions by LPxTG-anchored pneumococcal adhesins and their streptococcal homologues," Cell Microbiol, 2011, 13(2): 186-197.

Luo et al., "Solution structure of choline binding protein A, the major adhesin of *Streptococcus pneumonia*," Embo J, 2005, 24(1): 34-43.

Maiden et al., "Multilocus sequence typing: a portable approach to the identification of clones within populations of pathogenic microorganisms," PNAS, 1998, 95: 3140-3145.

Mann et al., "Broadly Protective Protein-Based Pneumococcal Vaccine Composed of Pneumolysin Toxoid-CbpA Peptide Recombinant Fusion Protein," J Infect Dis, 2013, 209: 1116-1125.

Marimon et al., "*Streptococcus pneumoniae* ocular infections, prominent role of unencapsulated isolates in conjunctivitis," Clin Microbiol Infect, 2013, 19(7): E298-305.

Martin et al., "An outbreak of conjunctivitis due to atypical *Streptococcus pneumonia*," N Engl J Med, 2003, 348, 1112-1121.

Marttinen et al. "Detection of recombination events in bacterial genomes from large population samples," Nucleic Acids Res, 2012, 40(1): e6.

McDonald et al., "Efficacy and safety of besifloxacin ophthalmic suspension 0.6% compared with moxifloxacin ophthalmic solution 0.5% for treating bacterial conjunctivitis," Ophthalmology, 2009, 116: 1615-1623.

Menon et al., "Identification of an atypical zinc metalloproteinase, ZmpC, from an epidemic conjunctivitis-causing strain of *Streptococcus pneumonia*," Microb Pathog, 2013, 56: 40-46.

Michel et al., "Cloned alpha and beta C-protein antigens of group B streptococci elicit protective immunity," Infect Immun, 1991, 59(6): 2023-2028.

Mook-Kanamori et al., "Pathogenesis and pathophysiology of pneumococcal meningitis," Clin Microbiol Rev, 2011, 24(3): 557-591.

Pacheco et al., "Fucose sensing regulates bacterial intestinal colonization," Nature, 2012, 492: 113-117.

Park et al., "Nontypeable pneumococci can be divided into multiple cps types, including one type expressing the novel gene pspK," MBio, 2012, 3(3): 3-11.

Pettigrew et al., "Variation in the presence of neuraminidase genes among *Streptococcus pneumoniae* isolates with identical sequence types," Infect Immun, 2006, 74(6): 3360-3365.

Rosch et al., "Convergence of regulatory networks on the pilus locus of *Streptococcus pneumonia*," Infect Immun, 2008, 76(7): 3187-3196.

Royle et al., "Glycan structures of ocular surface mucins in man, rabbit and dog display species differences," Glycoconj J, 2008, 25: 763-773.

Sachedina et al., "Phosphatic intermediate metabolites of the porcine ocular tunica fibrosa," Exp Eye Res, 1991, 52: 253-260.

Sanfilippo et al., "Strain ST448 causes the majority of pneumococcal conjunctivitis cases," in Association for Research in Vision and Ophthalmology (ARVO), Fort Lauderdale, Florida, 2012.

Shainheit et al., "Mutations in pneumococcal cpsE generated via in vitro mechanism of reduced encapsulation utilized by a conjunctival isolate," XP055256108, Journal of Bacteriology, May 2015, 197(10): 1781-1791.

Shayegani et al., "Characterization of nontypable *Streptococcus pneumoniae*-like organisms isolated from outbreaks of conjunctivitis," J Clin Microbiol, 1982, 16(1): 8-14.

Stahl et al., "L-fucose utilization provides Campylobacter jejuni with a competitive advantage," PNAS, 2011,108(17): 7194-7199.

Tepedino et al., "Phase III efficacy and safety study of besifloxacin ophthalmic suspension 0.6% in the treatment of bacterial conjunctivitis," Curr Med Res Opin, 2009, 25: 1159-1169.

Tuomanen et al., "Pathogenesis of pneumococcal infection," N Engl J Med, 1995, 332(19): 1280-1284.

Valentino et al., "Genomics of the conjunctival pathogen *Streptococcus pneumoniae*," ARVO Annual Meeting Abstract, Jun. 2013, IOVS, 54(15): 5222: 2 pages.

Valentino et al., "Unencapsulated *Streptococcus pneumoniae* from conjunctivitis encode variant traits and belong to a distinct phylogenetic cluster," Nature Communications, Nov. 2014, 5(12): 5411.

Vernatter et al., "Current concepts in host-microbe interaction leading to pneumococcal pneumonia," Curr Opin Infect Dis, 2013, 26(3): 277-283.

Weinert et al., "Molecular dating of human-to-bovid host jumps by *Staphylococcus aureus* reveals an association with the spread of domestication," Biol Lett 8: 829-832, 2012.

Wells et al., "Complex carbohydrates at the ocular surface of the mouse: an ultrastructural and cytochemical analysis," Exp Eye Res, 1984, 39(1): 19-35.

Zankari et al., "Identification of acquired antimicrobial resistance genes," J Antimicrob Chemother, 2012, 67: 2640-2644.

Zegans et al., "Clinical features, outcomes, and costs of a conjunctivitis outbreak caused by the ST448 strain of *Streptococcus pneumoniae*," Cornea, 2009, 28(5): 503-509.

Zhang et al., "The polymeric immunoglobulin receptor translocates pneumococci across human nasopharyngeal epithelial cells," Cell, 2000, 102: 827-837.

\* cited by examiner

```
TIGR4           AKSSDSSVGE ETLESFSLRP ERNVAEAENK VEEAMKKAED QNEEDRRNYP INTYKTLELE LAESDVEVRK
R6              AKSSDSSVGE ETLPSSSLKS GNKVAEAENK VEFAEKTARD QNEEDRRNYP INTYKTLDLE LAESDVRVKE
ST448           EKNS------ QVVQKIDDEL QELINEAKRE LEKLNQGIAE VDKLPELPAN DSDNVQKKY  IMDEDKETIP
S. agalactiae   DSKTEEKVPQ EPKSNDKNQL QELIKSAQQE LEKLEKAIKE LMEQPE--IP SNPEYGIQKS IWESDMEPIQ
                                                                     └─── 3G12 mAb epitope ───┘
                                                                                       414
                                                                                        |
TIGR4           AELELVREEA KEPRNEERVN QANAEVESKN AFATRLERIK TDRNKAEEFA FRKAAEEDNV KEKP
R6              AELELVREEA KEPRDEEKIN QAVAVESKN  AFATRLENIK TDRKKAEEFA FRKAAEEDNV KEKP
ST448           KKIAKFKENL G-----SKYIYN ESLQKFIDDC IYYQTHAKIE VMTRKVAGYR KAYPNNPEIE KFV
S. agalactiae   EAITSFKII  GDSSSKYTTE HYFNKYRSDE MNYQLHAQME MLTRFVVQYM MEYPDNAEIK KIFE
                           └─── 3H11 mAb epitope ───┘            └─── 14A3 mAb epitope ───┘
```

FIG. 11B

| | Start | Sequence | End |
|---|---|---|---|
| S. agalactiae | 204 | QVEKMAEQKG ITNEDKDSNL KRIEDIRKQA QQADKKEDAE | 243 |
| ST448 | 150 | QIRRNFEQKG ITNEDKDAML KKIAETHQEA EKDIKASGGY | 189 |
| TIGR4 | 195 | KDQKEEDRRN YPTITYKTLE LEIAESDVEV KKAELELVKV | 234 |
| R6 | 156 | EDQKEEDRRN YPTNTYKTLE LEIAEFDVKV KEAELELVKE | 195 |
|  |  | └──── Fc IgA binding domain ────┘ |  |

FIG. 11C

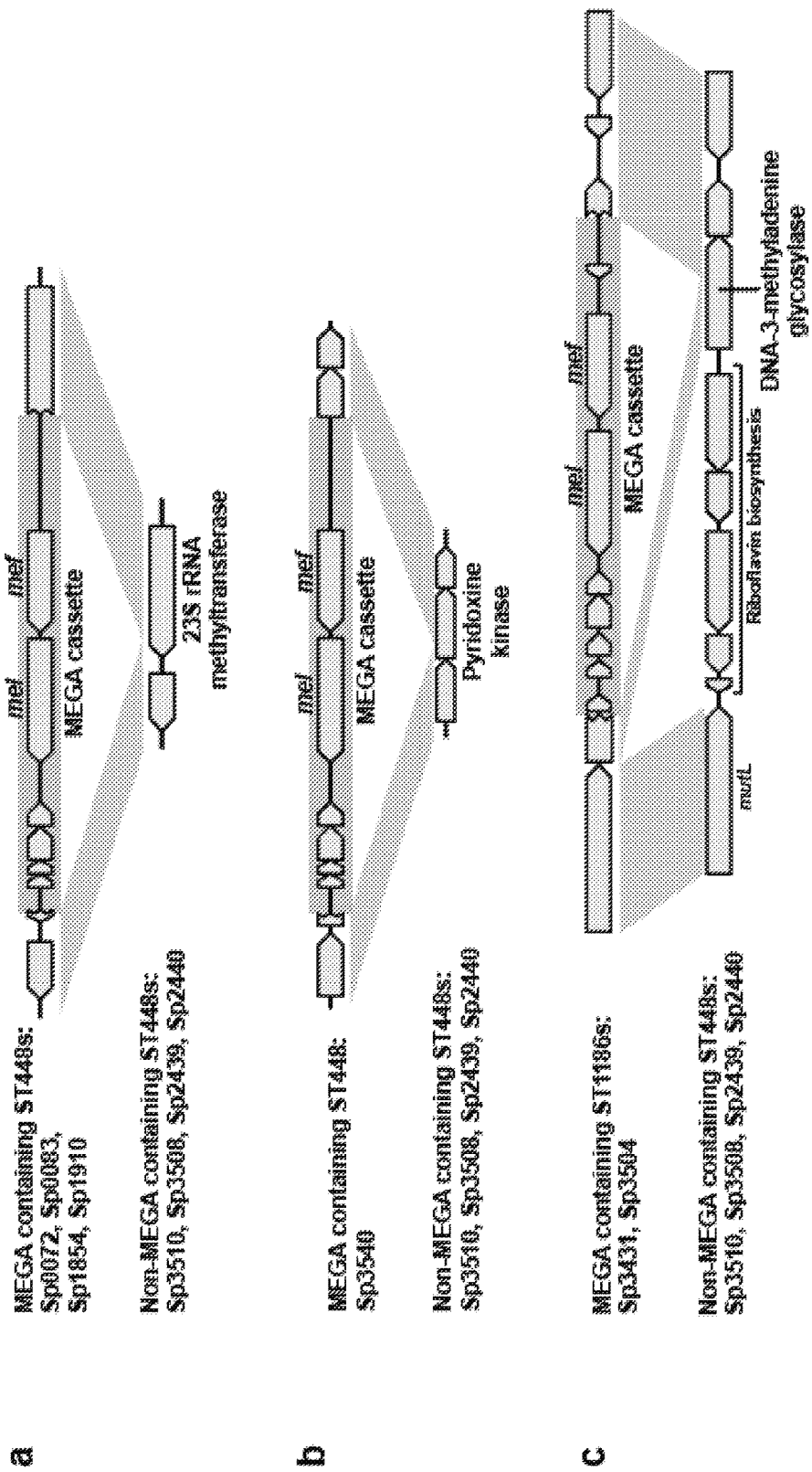
FIGS. 13A-C

US 10,420,826 B2

CONJUNCTIVITIS VACCINES

CLAIM OF PRIORITY

This application is a 371 U.S. National Application of PCT Application No. PCT/US2015/060009, filed on Nov. 10, 2015, which claims the benefit of U.S. Provisional Patent Application Ser. No. 62/078,357, filed on Nov. 11, 2014. The entire contents of the foregoing are hereby incorporated by reference.

FEDERALLY SPONSORED RESEARCH OR DEVELOPMENT

This invention was made with Government support under Grant No. EY024285 awarded by the National Eye Institute of the National Institutes of Health. The Government has certain rights in the invention.

TECHNICAL FIELD

Described herein are compositions comprising antigenic peptides, and their use in inducing an immunoprotective response in a subject against an infection Streptococcus pneumonia, or for treating or preventing, i.e., reducing risk of, an infection of Streptococcus pneumonia.

BACKGROUND

Streptococcus pneumoniae is a leading cause of invasive infections including pneumonia, meningitis, and sepsis, as well as non-invasive infections including pharyngitis and otitis media, and the polysaccharide capsule, a key virulence factor, is the target of current vaccines[1-3]. Vaccination has substantially reduced morbidity and mortality[3], but has had limited impact on infection of the mucous membrane covering the eye and lining the eyelids, conjunctivitis[4].

We recently collected 271 S. pneumoniae isolates during the course of clinical trials for the treatment of bacterial conjunctivitis[5-7], and found that over 90% were unencapsulated[8], and hence unaffected by current vaccine design. Unencapsulated S. pneumoniae strains have caused large conjunctivitis outbreaks in schools and colleges[9-13], military training facilities in the US[14], and other locations worldwide[15]. Recent outbreaks have involved one multilocus sequence type (MLST) in particular, ST448[13]. However, a previous study of epidemiologically unrelated conjunctivitis cases found that most cases were caused by encapsulated strains[4]. That study examined isolates prior to the widespread use of the PCV7 vaccine introduced in 20004.

SUMMARY

Streptococcus pneumoniae is an inhabitant of the upper respiratory mucosa, and a major cause of respiratory and invasive infection. It is also a leading cause of bacterial conjunctivitis. Strains that lack the capsule, a main virulence factor and the target of current vaccines, are often isolated from conjunctivitis cases. With a view toward understanding the diversity of S. pneumoniae causing conjunctivitis, their relationship to strains causing infection at other anatomical sites, and to identify potential virulence factors uniquely associated with conjunctivitis, we collected 271 strains from 72 postal codes in the US. By comparative genomic analysis, we found that the vast majority of conjunctivitis strains form a distinct cluster of closely related unencapsulated strains. This population exhibits large differences in gene repertoire, having acquired a number of novel traits from the Mitis-group and more distantly related streptococci. We found divergent forms of virulence factors that are characteristic of S. pneumoniae, including novel forms of CbpA and neuraminidases that were not shared with any other unencapsulated nasopharyngeal S. pneumoniae. Among novel genes not previously described to occur in encapsulated S. pneumoniae are putative adhesins otherwise widely distributed among streptococci. The cell surface proteins can be used to generate vaccines targeting these unencapsulated S. pneumonia.

Thus, provided herein are compositions comprising one or more peptides, each of said peptides comprising one or more antigenic epitopes from one or more of the following proteins: SspBC1 (X231_1085), SspBC2 (X231_1187), PspO (X231_1186), ZmpC2 (X231_0594), NanO1 (X231_0534), NanO2 (X231_0533), CbpI1 (BM49_0273), CbpI2 (X231_0220), CbpAC1 and CbpAC2.

In some embodiments, the compositions include peptides derived from one, two, three, or all four of CbpAC1, CbpAC2, NanO1, and NanO2. In some embodiments, the compositions include peptides derived from one, two, three, or all four of CbpAC1, CbpAC2, NanO1, and NanO2, plus one or both of SspBC1 and SspBC2. As an alternative, the composition may include nucleic acids encoding the peptides.

In some embodiments, the composition includes one or more of an antigen delivery system, an adjuvant, and/or a pharmaceutically acceptable excipient.

In some embodiments, the composition is a vaccine.

Also provided herein are methods for inducing an immunoprotective response in a subject against an infection Streptococcus pneumonia, or for treating or preventing, i.e., reducing risk of an infection of Streptococcus pneumonia, by administering a composition as described herein.

In some embodiments, the infection is an ocular infection, e.g., conjunctivitis.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 11A-D. ECC genomes carry an atypical virulence factor at the CbpA locus. (a) Western blot of total bacterial extracts, probed with three monoclonal antibodies (clones: 3H11, 14A-3, 3G12 see Mann et al.[34]) that recognize highly conserved epitopes within CbpA (see panel B). T4, TIGR4; delta-cbpA, TIGR4 with CbpA deleted. Pneumolysin served as positive control for protein loading (anti-Ply). (b) CbpA sequence of *S. pneumoniae* strains TIGR4, R6, and ST448, and *S. agalactiae* strain A909 C beta-antigen. Peptide sequences in agreement with the TIGR4 reference are highlighted. The anti-CbpA monoclonal epitopes from (a) are denoted. (c) Sequence of the IgA-Fc binding domain of C beta-antigen across *S. agalactiae*, ST448 and *S. pneumoniae* strains TIGR4 and R6. Peptide sequences in agreement with the *S. agalacticae* A909 reference are highlighted in gray. (d) Genome synteny surrounding CbpA-C1 and CbpA-C2, including the TCS system controlling CbpA expression, as compared to TIGR4 reference. CbpA, CbpA-C1, CbpA-C2 illustrated as described in FIG. 5. Sequence associated with *S. pneumoniae* (dark gray), *S. agalactiae* (white), *S. pseudopneumoniae* (black), and sequence that could not be assigned to an organism (star) are indicated. Nucleotide sequence with identity is shown by grey shading between the constructs. Loss of nucleotide synteny in the ECC genomes compared to TIGR4 occurs exactly at the end of SP_2189 and SP_2194, and is shared at the exact location in all ECC genomes.

FIGS. 13A-E. Structure of macrolide resistance elements in ECC isolates. Structure of the resistance elements within: ST448 genomes ECC_0071, ECC_0083, ECC_1854, ECC_1910 (a) or ECC_3510 (b) as compared to non-MEGA containing ST448s; (c) ST1186 genomes compared to TIGR4 as a reference; (d) ST344 and ST1270 genomes; (e) non-ocular references strains. Regions of shared sequence are shown by grey shading between the isolates.

DETAILED DESCRIPTION

Figure 14:
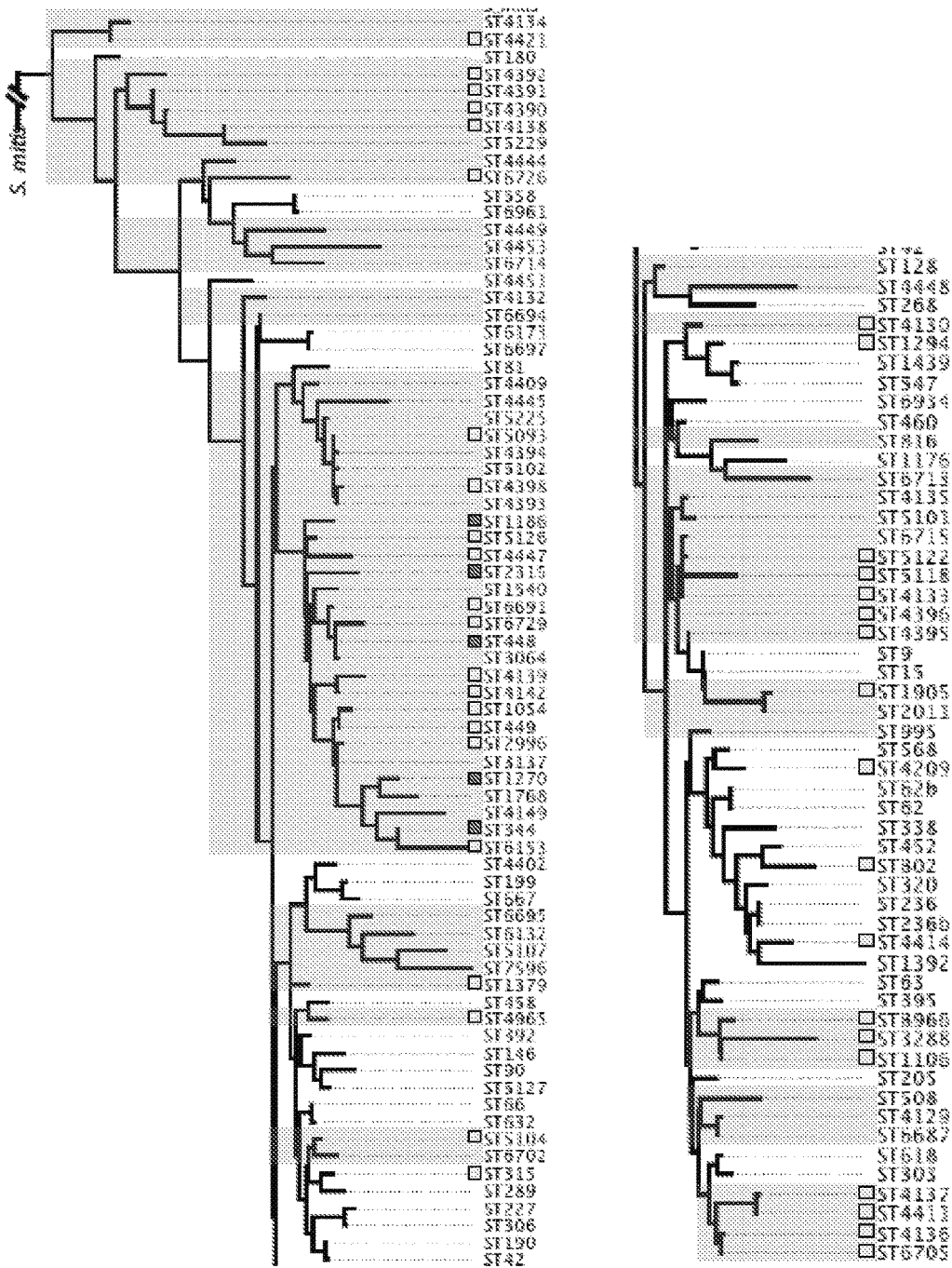
FIG. 14. MLST-based phylogenetic relationships among *S. pneumoniae* strains. Included are sequence types represented in FIG. 2 (from conjunctivitis and other infections) and sequence types found in two recent surveys of nasopharyngeal colonization[19,41]. Unencapsulated strains are highlighted in grey. ECC members are denoted with a dark grey box. A diverse set of genomes was selected from two recent nasopharyngeal carriage surveys[19,41] for additional analyses are denoted with a light grey box.
Figure 15:
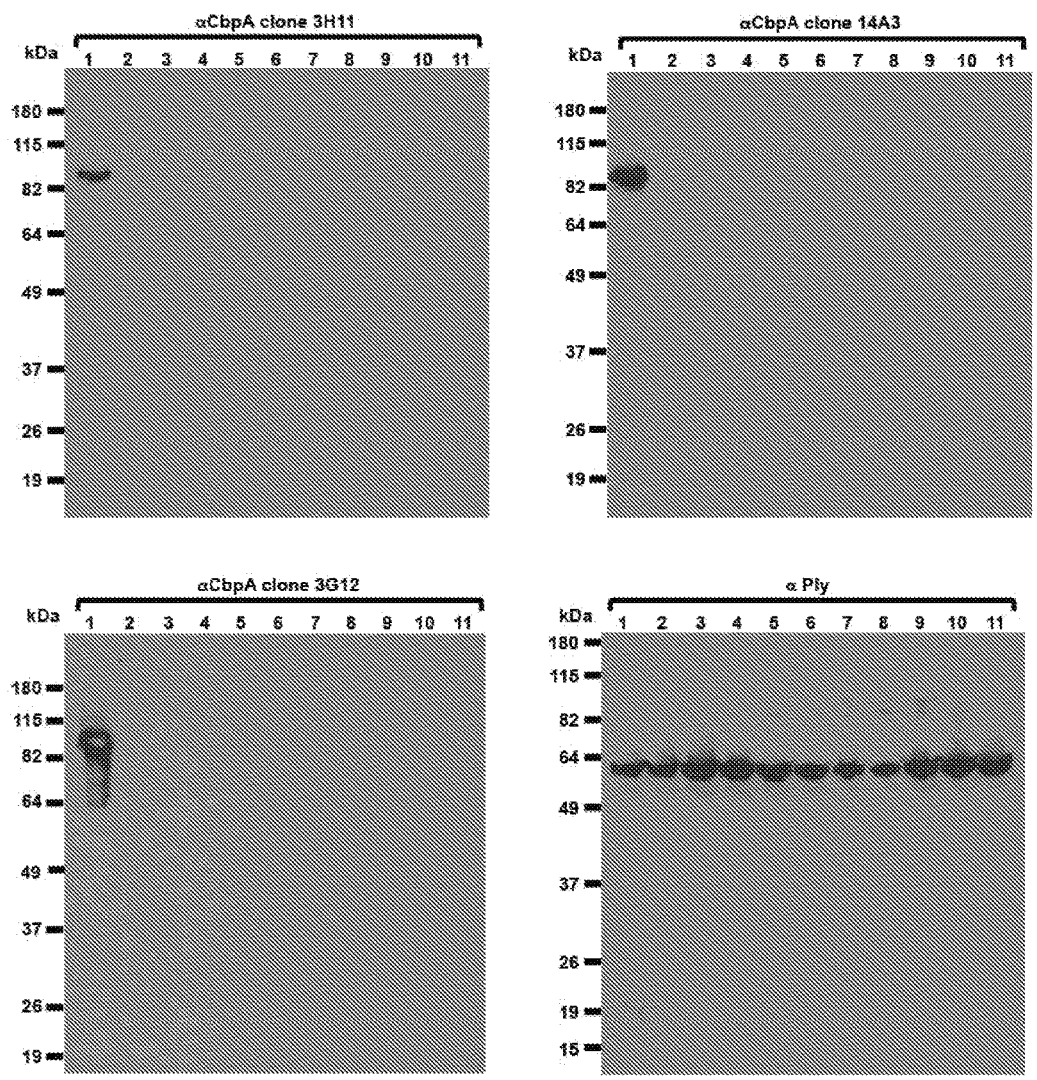
FIG. 15. Western blots for canonical CbpA. Western blot of total bacterial extracts, probed with monoclonal antibodies against CbpA (clones: 3H11, 14A-3, 3G12 see Mann et al.[2]) and pneumolysin (anti-Ply). Lanes 1 through 11 are identical to those shown in FIG. 11. Molecular weight markers are denoted.

With a view toward understanding strain diversity and the molecular basis for virulence of *S. pneumoniae* in conjunctivitis, and to improving vaccine design to cover this disease, we characterized recent isolates from across the US. We found that nearly 90% of conjunctivitis cases were caused by five related STs (ST448, ST344, ST1186, ST1270, ST2315) that fall within a deep branch of the *S. pneumoniae* species (see FIG. 6 and FIG. 14), a finding supported by two recent reports[19,41]. This divergence is characterized by novel gene content constituting approximately 10% of the genome. Although ECC strains possess a large amount of novel genes, shared genes exhibit an average nucleotide identity of 97.9%+/−0.11 ANI with strains from other types of infection, and therefore ECC strains do not constitute a new species (ANI<95%) by this definition[21,42,19].

Figure 6:
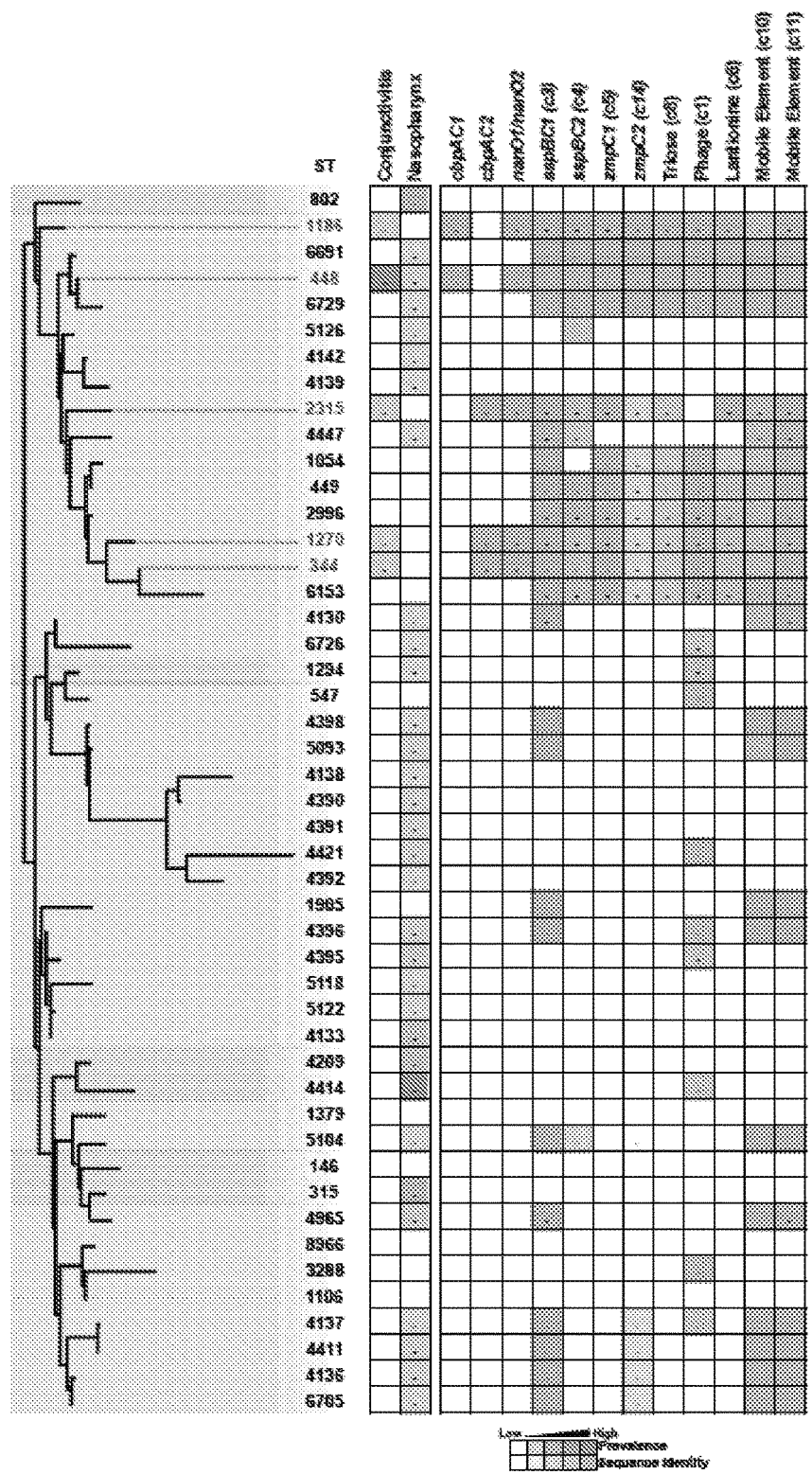
FIG. 6. Presence of ECC genes in genomes of nasopharyngeal isolates. All STs representative of unencapsulated strains (light grey highlight), and the most prevalent encapsulated strains (medium grey highlight), from two recent large scale surveys of asymptomatic nasopharyngeal carriage[19,41], compared to ECC members associated with conjunctivitis (grey text and line extension), shown in a PhyML SNP-based tree based on the concatenated alignments of MLST alleles. Bootstrapping was performed with 1000 iterations. Prevalence in conjunctivitis (this study) and nasopharyngeal carriage[41] is shown. Percent presence and sequence identity of gene (gene, cluster number) or cluster (predicted function, cluster number) is denoted with green boxes.
Figure 7:
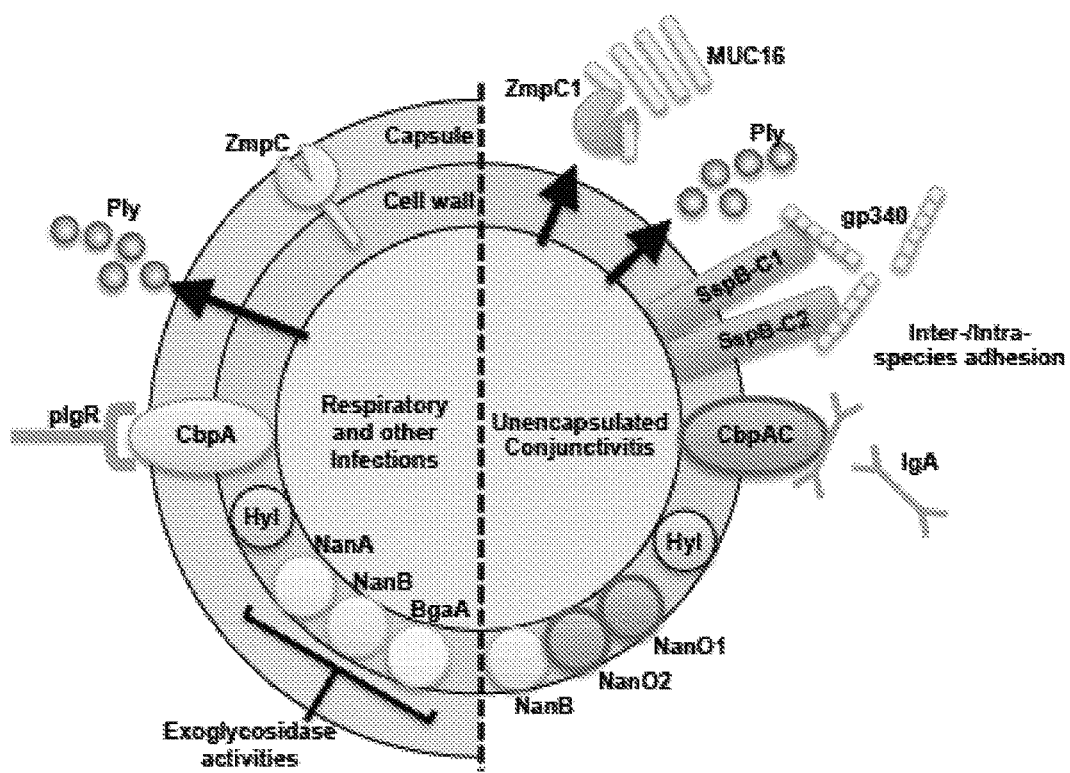
FIG. 7. Virulence factor differences between invasive and ECC strains. New traits found within ECC and closely related genomes are shown in solid grey, with those unique to STs associated with conjunctivitis highlighted with a darker grey outline. CbpAC1 and CbpAC2 are shown as CbpAC since ECC strains express one or the other, but not both. Predicted ligands for SspBC1, SspBC2, and CbpAC are shown. Arrows indicate secreted products.

We found genes cbpAC1, cbpAC2, nanO1, nanO2 were only carried by STs that are associated with conjunctivitis (see FIG. 6 and FIG. 7). Other genes enriched in ECC, including the sspBC agglutinins, zmpC1, zmpC2, and the triose metabolic cassette, were found to be shared among a few closely related unencapsulated STs (ST6153, ST6691, ST6729, ST2996, ST1054, ST449) that have not been identified in cases of conjunctivitis, which may stem from the paucity of studies that have identified MLST types of S. pneumoniae causing conjunctivitis. These additional genes are largely absent in encapsulated and more distantly related unencapsulated genomes unrelated to conjunctivitis however (see FIG. 6 and FIG. 7). These findings suggest that some of the genes enriched in ECC are fundamental to the formation of the larger unencapsulated lineage to which ECC members belong (see FIG. 6 and FIG. 14).

Typifying the conjunctivitis-associated strains is a lack of capsule, rendering them unaffected by current polyvalent pneumococcal capsule vaccines. As would be predicted for a lineage that professionally lacks the polyanionic capsule through which surface proteins must fold and extend, these strains have substantially different surface features, including those known to contribute to virulence (FIG. 7). Novel features, specific to ECC STs include substantially altered forms of CbpA, CbpAC1 and CbpAC2. Interestingly, these altered forms no longer possess the key domain that mediates binding to host polymeric immunoglobulin receptor (pIgR), which S. pneumoniae use to facilitate transcytosis from nasopharyngeal epithelia into the blood stream[35]. Instead, both CbpAC1 and CbpAC2 appear to have independently swapped that domain for one that mediates direct binding to secretory IgA (sIgA)[33,36,43]. The implication is that ECC strains bind sIgA in a subtly, but importantly different way, possibly coating themselves with IgA, in a manner analogous to that mediated by protein A of S. aureus[44]. Alternatively, these CbpA variants may act as adhesins for attachment to surfaces coated with antibodies, as suggested for immunoglobulin receptors in Streptococcus pyogenes[45]. That this change appears to have occurred twice, and that only variants of CbpA occur in unencapsulated STs associated with conjunctivitis, suggests that it is important for the ocular tropism. In addition to the variant CbpA, all ECC genomes also encode two novel, divergent choline binding protein CbpI's, here termed CbpI1 and CbpI2. No function has yet to be ascribed to CbpI, CbpI1 or CbpI2.

Other factors unique to STs associated with conjunctivitis that would affect the host/microbe interface include the displacement of NanA with two variant sialidases, NanO1 and NanO2. This recombination event is seen only in ECC members and is absent in even the closest non-ECC relatives. Since sialic acid residues exhibit variation among host cell types it has been suggested that they are mediators of tissue tropism[46]. This is of potential relevance to conjunctivitis, since proteins found at the ocular surface are decorated by covalently-bound sialic acids[47], which have been shown to mediate ocular surface binding of Pseudomonas aeruginosa and Escherichia coli[48,49].

A recurring motif was the replacement of surface features optimized for function in the presence of a capsule, with surface features derived from unencapsulated oral streptococci (e.g. S. mitis). Others have noted that S. mitis appears to be a reservoir for genetic diversity[50]. Additional novel surface features of ECC and closely related unencapsulated strains likely involved in colonization, and likely originating in oral streptococci, include two Antigen I/II (AgI/II) family of adhesins/agglutinins encoded in separate genomic islands, SspBC1 and SspBC2. Notably, sspBC2 is restricted to ECC and closely related strains potentially implicating its involvement in the unusual ocular surface tropism, whereas sspBC1 is also found within more distantly unencapsulated genomes, implicating its possible involvement in colonization of the nasopharynx and adnexa (see FIG. 6). The AgI/II family of adhesins are central to colonization and biofilm formation by commensal and pathogenic species of Streptococcus[24,51]. A previous review noted their ubiquitous presence among streptococci except for S. pneumoniae[51]. The observation here that these genes occur in unencapsulated strains of S. pneumoniae, suggests either incompatibility or functional redundancy with the pneumococcal capsule. In terms of colonization (nasopharyngeal and/or ocular) and conjunctivitis pathogenesis, SspB-domains of AgI/II proteins mediate binding to human scavenger protein gp-340[24], which occurs in tears and on the ocular surface[52].

All STs associated with conjunctivitis encoded a novel phage element (cluster 9/cluster 11). This element was also seen in closely related unencapsulated nasopharyngeal strains, whereas it was rarely found in more distantly related unencapsulated strains. Interestingly, this element is located at different sites in the genomes of the conjunctivitis associated sequence types, but is always consistent within an ST. This suggests that it was lacking from a common ancestor and has been acquired independently, or that it is internally mobile. There are no obvious adhesins or virulence traits encoded within this element, but it may contribute to biofilm formation as described for other phage elements in S. pneumoniae[53]. Its presence within numerous nasopharyngeal STs suggests it may play a basic function in colonization for unencapsulated varieties of S. pneumoniae.

A unique metabolic feature profile was found among ECC and closely related strains, suggesting that their colonization ability is likely nutritionally distinct from that of strains associated with invasive infection. A phosphoenolpyruvate-dihydroxyacetone PTS gene cluster occurring in ECC and closely related nasopharyngeal strains and only 1 distantly related strain from otitis media (Hungary19A-6), (cluster 8), also found in S. mitis and S. pseudopneumoniae, suggests that the ability to metabolize Dha is important for mucosal surface colonization. DhaP was detected among the phosphorylated intermediate metabolites present on the ocular sclera and corneal tissues[54].

In addition to the gain of putative metabolic capabilities described above, all ST genomes associated with conjunctivitis lacked the ability to metabolize fucose, a sugar that decorates ocular glycans present in the glycocalyx of corneal epithelial cells[49]. Fucosylated glycans coating mucins are known to promote bacterial colonization in the gut, serving as both adherence targets, as well as a carbon source[55,56]. Specifically at the ocular surface, fucose residues have been implicated in the attachment of P. aeruginosa and E. coli to ocular epithelial cells[49]. Moreover, application of exogenous fucose was shown to suppress inflammation in rabbit corneal and explanted human cornea models of wound healing[57]. Nasopharyngeal STs closely related to ECC members (ST6691, ST6729, ST1054, ST449, ST2996, ST6153) were also found to lack the elements to metabolize fucose. These findings suggest the inability to metabolize fucose is irrelevant for colonizing the nasopharynx, but may confer an advantage at the ocular surface, potentially by promoting an anti-inflammatory environment and/or by preserving an important bacterial ligand.

While asymptomatic carriage in the nasopharyngeal cavity is likely to be a precursor to infection, ST448[9,12,13,15,18] and related STs commonly isolated conjunctivitis were not highly prevalent in recent large scale surveys of asymptomatic *S. pneumoniae* carriage in the nasopharynx[19,41]. Whereas ST448 was found to be by far the leading cause of conjunctivitis in this study as well as in others[15,18], it represented only 1.43% of 3,084 isolates found to be asymptomatically carried by Chewapreecha et al.[41], and 1.14% of nasopharyngeal isolates examined by Croucher et al.[19]. Indeed, there are four other unencapsulated STs found at similar or higher prevalence within the nasopharynges (ST4133, ST4395, ST4965, ST4136 ranging from 1.43-2.92%), the most prevalent of which, ST4133, has not been reported as a cause of conjunctivitis, is not closely related to the STs most commonly associated with conjunctivitis and does not encode the genes enriched in ECC that were searched, highlighting the point that it is not the simple lack of capsule that predisposes these strains to cause conjunctivitis. The four most common STs (ST4414, ST802, ST315, ST4209) in nasopharyngeal carriage are all encapsulated (a cumulative 19.98% of 3,084 isolates), and lack all ECC-associated genes (except for a phage (cluster 1) shared only in ST4414) and were not found among our collection of 271 conjunctivitis isolates. Similar findings were seen by Croucher et al.[19], with 1.14% of nasopharyngeal isolates being ST448 (21$^{st}$ most common ST), in this case representing the most common unencapsulated ST recovered in their study. Taken together, these findings highlight that prevalence in the nasopharynges does not directly correlate with conjunctival infection, in further support of the hypothesis that genes unique to ECC genomes are critical for conjunctival infection.

It is unlikely that the unencapsulated cluster containing ECC members arose due to vaccine use, as has been speculated[8], based upon the extent of divergence between ECC lineages investigated herein and non-ocular lineages (an average 27,754+/−1,831 SNPs). Based on a recent determination of *S. pneumoniae* mutation rate[58] (and assuming this measure is true for ECC members as well), the bifurcation between ECC and the main branch of the species took place approximately 8,400 years ago (8,385+/−553 years). That the rate of divergence measured for other *S. pneumoniae* also applies to ECC rates of change stems from a comparison of the distance between strains isolated from geographically and temporally related outbreaks in Maine and New Hampshire. With epidemiologic centers about 7 months apart, strains from the New Hampshire outbreak (ECC_1854, ECC_1910) differ from those from the Maine outbreak (ECC_0072, ECC_0083) 4.67+/−2.1 SNPs, a mutation rate of $1.43 \times 10^{-6}$ substitutions per site per year, in agreement with previous calculations $1.57 \times 10^{-6}$ substitutions per site per year[58]. This dating is similar to estimates of clade divergence in *E. faecium*[59], and *S. aureus*[60], both of which were attributed to increasing urbanization. This suggests that in contrast to the ancestral line, there is an especially important role for person to person transmission in the propagation of either this lineage, or the branch associated with respiratory infection.

In summary, we found that 5 STs commonly associated with conjunctivitis (which accounted for 90% of *S. pneumoniae* conjunctivitis cases studied) fall within a deeply resolved cluster of unencapsulated strains within the *S. pneumoniae* species. These strains are typified by substantially different features including elements exclusive to strains associated with conjunctivitis (CbpAC1, CbpAC2, NanO1, NanO2) that may contribute to their ocular tropism. Additional features were shared with only closely related unencapsulated varieties (e.g. ZmpC, SspBC2), or sporadically among distantly related unencapsulated strains (e.g. SspBC1). Currently 90% of the *S. pneumoniae* strains associated with conjunctivitis are not covered by existing vaccines. Furthermore, because of the extensive variation observed, vaccines under development that target conventional *S. pneumoniae* virulence traits (e.g. CbpA) may or may not provide coverage for preventing conjunctivitis. This knowledge of conserved and variant features occurring in the ECC members is critical for vaccine design strategies.

Thus provided herein are compositions for use in eliciting an immune response against these unencapsulated *S. pneumonia*, e.g., as vaccines, and are useful in reducing risk of developing conjunctivitis. The compositions are particularly useful in subjects who are at high risk of developing conjunctivitis, e.g., children and those who work with them. The compositions include peptides derived from one, two, three, or more of the following:

SspBC1 (X231_1085) and SspBC2 (X231_1187)
PspO (X231_1186)
ZmpC2 (X231_0594)
NanO1 (X231_0534)
NanO2 (X231_0533)
CbpI1 (BM49_0273)
CbpI2 (X231_0220)
CbpAC1
CbpAC2

In some embodiments, the compositions include peptides derived from one, two, three, or all four of cbpAC1, cbpAC2, nanO1, and nanO2. In some embodiments, the compositions include peptides derived from one, two, three, or all four of cbpAC1, cbpAC2, nanO1, and nanO2, plus one or both of SspBC1 and SspBC2. As an alternative, the composition may include nucleic acids encoding the peptides.

The compositions can include peptides that include the entire sequence of each of the antigens described above, but will preferably include only extracellular sequences, and may only include portions of the extracellular sequences, e.g., antigenic fragments thereof. Preferred epitopes encompassed by the antigenic peptide are regions that are located on the surface of the proteins, e.g., hydrophilic regions, as well as regions with high antigenicity. For example, an Emini surface probability analysis of the protein sequences set forth above can be used to indicate the regions that have a particularly high probability of being localized to the surface of the protein and are thus likely to constitute surface residues useful for targeting antibody production. See, e.g., Hopp, Protein surface analysis. Methods for identifying antigenic determinants and other interaction sites. J Immunol Methods. 1986 Apr. 3; 88(1):1-18.

The compositions described herein can include an antigen delivery system, which optimizes the presentation of the antigen. In a specific embodiment, the antigen delivery system is an enzymatically inactive recombinant adenylate cyclase (CyaA) originating from *Bordetella pertussis* (the causative agent of whooping cough) (Ladant et al., 1999; and in EP1576967).

The methods can further include administration of an adjuvant, e.g., a compound that enhances the longevity, potency, and/or quality of the specific immune response to an antigen described herein, and preferably has no or minimal toxicity or long-lasting immune effects on its own. The adjuvant can be incorporated into the compositions described herein or administered separately. Suitable adjuvants are 1) receptor specific (mucosal) adjuvants such as for instance adjuvants binding to pathogen recognition receptors (PRRs) and ganglioside receptor binding toxins, 2) antigen presenting cell targeting (mucosal) adjuvants such as for instance the ones described by Gerdts et al., (2006). Further examples of adjuvants include, but are not limited to, tensoactive compounds (such as Quil A), mineral salts (such as aluminium hydroxide), micro-organism derived adjuvants (such as muramyl dipeptide), oil-in-water and water-in-oil emulsions (such as Freund's incomplete adjuvant), particulate antigen delivery systems (such as liposomes, polymeric atmospheres, nanobeads, ISCOMATRIX), polysaccharides (such as micro-particulate inulin), nucleic acid based adjuvants (such as CpG motivs), cytokines (such as interleukins and interferons), activators of Toll-like receptors and eurocine L3 en N3 adjuvantia. In a specific embodiment, the adjuvant is an ISCOM™ (ISCOTEC AB, Uppsala, Sweden). Adjuvants can include, for example, mineral salt adjuvants (e.g., alum-based); tensoactive adjuvants (e.g., saponins); polymeric microspheres (e.g., poly (DL-lactide-coglycolide) microspheres); bacteria-derived adjuvants (e.g., N-acetyl muramyl-L-alanyl-D-isoglutamine (MDP)); liposome adjuvants; adjuvant emulsions (e.g., oil in water or water in oil emulsions such as FIA, Montanide, Adjuvant 65, and Lipovant); cytokines (e.g., IFN-gamma or GM-CSF); and carbohydrate adjuvants (e.g., inulin), among others. The choice of adjuvant can be determined by the nature of the antigen (e.g., protein or nucleic acid) and the route of administration (e.g., parenteral or mucosal). See, e.g., Petrovsky and Aguilar, Immunology and Cell Biology (2004) 82, 488-496; Kenney and Edelman, Expert Rev Vaccines. 2003 April; 2(2):167-88; Coler et al., Parasite Immunol. 2009 September; 31(9):520-8; and Reed et al., Trends Immunol. 2009 January; 30(1):23-32. In some embodiments, the adjuvants include an oil in water emulsion, monophosphoryl lipid A and the saponin derivative QS21 (Stoute et al., J Infect Dis. 178 (4):1139-1144 (1998)). Adjuvants that are safe for use in the eye can be used in compositions to be administered ocularly.

The compositions described herein can be used as a medicament, and more specific against a conjunctival infection with a species of the genus *Streptococcus*, preferably wherein said species of the genus *Streptococcus* is *Streptococcus pneumoniae*. In a further embodiment, the composition is a vaccine. With the term 'vaccine' is meant a biological preparation that elicits a protective immune response in a subject to which the vaccine has been administered. Preferably, the immune response confers some beneficial, protective effect to the subject against a subsequent challenge with the infectious agent. More preferably, the immune response prevents the onset of or ameliorates at least one symptom of a disease associated with the infectious agent, or reduces the severity of at least one symptom of a disease associated with the infectious agent upon subsequent challenge.

Pharmaceutical Compositions and Methods of Administration

The methods described herein include the use of pharmaceutical compositions comprising the peptide antigens described herein.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

For administration by inhalation, the compounds are typically delivered in the form of an aerosol spray from pressured container or dispenser which contains a suitable propellant, e.g., a gas such as carbon dioxide, or a nebulizer. Such methods include those described in U.S. Pat. No. 6,468,798.

Pharmaceutical compositions comprising peptide antigen-encoding nucleic acids can be administered by any method suitable for administration of nucleic acid agents, such as DNA vaccines. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the pharmaceutical compositions include carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

Dosage, toxicity and therapeutic efficacy of the antigens can be determined by standard vaccine testing procedures in experimental animals or clinical trials, e.g., for determining the LD50 (the dose lethal to 50% of the population) and the ED50 (the dose therapeutically effective in 50% of the population). The methods generally include administering at least one dose of the antigen compositions to a subject (e.g., test animal or human clinical trial subject), optionally followed after a period of time by one or more boost doses, and then protection from challenge by an appropriate organism is measured. The organism challenge can be performed by applying organisms collected from an infected individual to the eye of a test subject.

The data obtained from the animal studies can be used in formulating a range of dosage for use in humans, which is then confirmed in clinical trials, e.g., as described above. The dosage will lie preferably within a range of concentrations that include the ED50 with little or no toxicity. The dosage may vary within this range depending upon the dosage form employed (e.g., antigen protein or nucleic acid) and the route of administration utilized. A dose may be formulated in animal models to achieve a desired level of protection without significant toxicity. Such information can be used to determine useful starting doses in humans for clinical trials.

A therapeutically effective amount of an antigen (i.e., an effective dosage) as described herein depends on the form selected, e.g., whether antigen protein or antigen-encoding nucleic acid (e.g., a DNA vaccine) is used. The skilled artisan will appreciate that certain factors may influence the dosage and timing required to effectively elicit an immune response in a subject, including but not limited to previous treatments and the general health and/or age of the subject. Moreover, treatment of a subject with a therapeutically effective amount of the antigens described herein can include a single dose or a series of treatments (i.e., a priming dose and one or more boosts).

The antigens can be included in a kit, container, pack, or dispenser, optionally with instructions for administration, for use in a method described herein.

EXAMPLES

The invention is further described in the following examples, which do not limit the scope of the invention described in the claims.

Methods

The following materials and methods were used in the Examples set forth below.

Bacterial Strains.

A large and comprehensive collection of 280 *S. pneumoniae* conjunctivitis strains were assembled from across the USA, including 271 isolates obtained from 72 different zip codes, as well as one isolate from New Delhi, India as part of a national, multicenter, passive surveillance study of bacterial conjunctivitis[5-7]. Also included were two conjunctivitis isolates (6 in total) from each large outbreak occurring at Dartmouth College[10,12], an elementary school in Maine[13, 17], and a suburb of Minnesota[9], as well as three other conjunctivitis isolates of unknown origin were obtained from the CDC *Streptococcus* Laboratory. Strains were cultured on 5% sheep blood agar plates (BD Biosciences, San Jose, Calif.) or in Todd Hewitt broth supplemented with 5% yeast extract, and incubated at 37 C in 5% CO2. Bacterial isolates were confirmed as *S. pneumoniae* based on their hemolysis phenotype on blood agar plates, bile solubility, and susceptibility to optochin when grown in a 5% CO2 atmosphere[8].

Characterization of Ocular Isolates by MLST and Capsule Typing.

Multilocus sequence typing and capsule typing were performed on the 271 strains collected from the large US multicenter trial[5-7] (FIG. 1B). Briefly, sequence types were determined based on sequences for aroE, gdh, gki, recP, spi, xpt and ddl genes[61]. The presence of capsule was determined with both OMNI serum, as well as the capsule type-specific Pneumotest-Latex serum, both obtained from the Statens Serum Institut (MiraVista Diagnostics, Indianapolis, Ind.). Initial capsule typing results for 50 selected isolates were confirmed by the Statens Serum Institut in Denmark. A preliminary report of the distribution of MLST types has been presented previously[62].

Genome Sequencing.

Strains isolated from three well-documented major US outbreaks in Maine, New Hampshire and Minnesota, as well as strains that were representative of the MLST sequence types most prevalent among the 271 strains collected from the multicenter US study, were selected for genome sequencing. Briefly, total DNA was purified from a 5 mL overnight culture using the DNeasy DNA extraction kit (Qiagen, Valencia, Calif.). Library preparation for Illumina sequencing by Illumina was carried out using the Nextera DNA Sample Preparation kit (Illumina, San Diego, Calif.), according to manufacturer's specifications. DNA quality was verified on a Bio-Tek Synergy 2 microplate reader (Winooski, Vt.) prior to quantification using a Qubit fluorometer and dsDNA High-Sensitivity assay kit (Invitrogen, Carlsbad, Calif.). A transposome was used to simultaneously fragment and append adapter sequences to 50 ng of DNA per sample, followed by addition of dual-index sequences in a limited-cycle PCR step. Quality and quantity of each sample library was measured on an Agilent Technologies 2100 Bioanalyzer (Santa Clara, Calif.), with a target fragment size ~300 bp. The genomes of strains Sp0072, Sp0083, Sp1854, Sp1910, Sp0381, and Sp0391 were sequenced at the St. Jude Children's Hospital Hartwell Center for Bioinformatics and Biotechnology, Memphis, Tenn. on an Illumina GAXII sequencer, according to manufacturer's specifications. For all other genomes, libraries were normalized to 2 nM, multiplexed and subjected to either 150, 200 or 250 bp paired end sequencing on an Illumina MiSeq Personal Sequencer at the Mass. Eye and Ear Infirmary Ocular Genomics Institute (Boston, Mass.), according to manufacturer's specifications.

Genome Assemblies and Annotation.

Sequence reads were assembled de novo utilizing CLC Genomics Workbench v4.9 (CLC Bio, Cambridge, Mass.) (Table 3). On average, 3.7 million high-quality paired-end reads were collected for each strain, representing >240-fold coverage of the ~2.1 Mb genomes. Sequence reads below a quality score of 25 at any position were excluded from further analyses. All genomes compared in this study (Table S2) were annotated using the Rapid Annotation using Subsystem Technology (RAST) server[63], and Glimmer v.3[64], with comparison to family profiles in the FIGfam (protein families generated by the Fellowship for Interpretation of Genomes (FIG)) release 63 database. Wherever possible, manual search of the PFAM[65] database was used to assign functions to genes annotated as hypothetical. Draft genome sequences have been deposited in DDBJ/EMBL/GenBank under BioProject PRJNA22902, see Table 2 for accession numbers.

TABLE 2

Conjunctivitis and Non-ocular Reference strains compared in this study

Figure 2:
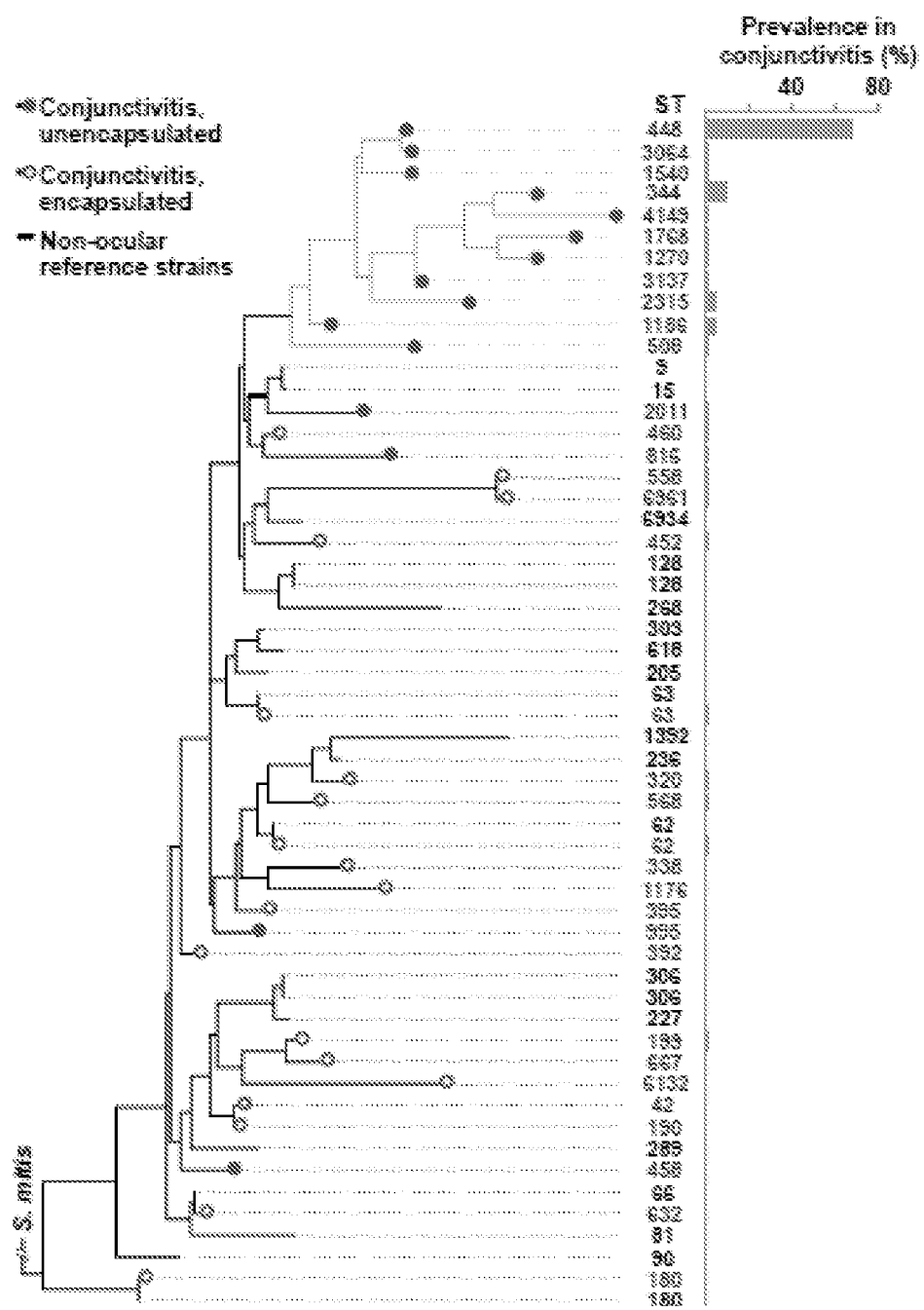
FIG. 2. MLST-based phylogenetic relationships among conjunctivitis strains. SNP-based tree based on a concatenation of MLST loci, with prevalence in conjunctivitis for each ST.

| Order on FIG. 2 tree | Strain Name | ST | Serotype | Location Isolated | Genome Length (bp) | Total Orthogroups | Accession Number |
|---|---|---|---|---|---|---|---|
| 1 | ECC_3507 | 2315 | NT | conjunctivitis | 2,133,084 | 2222 | JFJB00000000 |
| 2 | ECC_3502 | 1270 | NT | conjunctivitis | 2,151,962 | 2233 | JFIZ00000000 |

TABLE 2-continued

Conjunctivitis and Non-ocular Reference strains compared in this study

| Order on FIG. 2 tree | Strain Name | ST | Serotype | Location Isolated | Genome Length (bp) | Total Orthogroups | Accession Number |
|---|---|---|---|---|---|---|---|
| 3 | ECC_3517 | 1270 | NT | conjunctivitis | 2,133,241 | 2210 | JFJD00000000 |
| 4 | ECC_3435 | 344 | NT | conjunctivitis | 2,119,359 | 2208 | JFIX00000000 |
| 5 | ECC_3452 | 344 | NT | conjunctivitis | 2,132,262 | 2216 | JFIY00000000 |
| 6 | ECC_3431 | 1186 | NT | conjunctivitis | 2,118,601 | 2170 | JFIW00000000 |
| 7 | ECC_3504 | 1186 | NT | conjunctivitis | 2,131,110 | 2190 | JFJA00000000 |
| 8 | ECC_3540 | 448 | NT | conjunctivitis | 2,121,720 | 2189 | JFJE00000000 |
| 9 | ECC_2440 | 448 | NT | conjunctivitis | 2,126,208 | 2192 | JFIV00000000 |
| 10 | ECC_2439 | 448 | NT | conjunctivitis | 2,108,471 | 2186 | JFIU00000000 |
| 11 | ECC_3508 | 448 | NT | conjunctivitis | 2,114,550 | 2182 | JFJC00000000 |
| 12 | ECC_3510 | 448 | NT | conjunctivitis | 2,126,241 | 2210 | JDVZ00000000 |
| 13 | ECC_0072 | 448 | NT | conjunctivitis | 2,107,331 | 2148 | JFIQ00000000 |
| 14 | ECC_0083 | 448 | NT | conjunctivitis | 2,113,463 | 2158 | JFIR00000000 |
| 15 | ECC_1854 | 448 | NT | conjunctivitis | 2,113,718 | 2172 | JFIS00000000 |
| 16 | ECC_1910 | 448 | NT | conjunctivitis | 2,106,050 | 2151 | JFIT00000000 |
| 17 | Hungary19A-6 | 268 | 19A | otitis | 2,245,615 | 2358 | NC_010380 |
| 18 | TCH8431/19A | 320 | 19A | airways | 2,088,772 | 2131 | NC_014251 |
| 19 | ST556 | 1392 | 19F | otitis | 2,145,902 | 2199 | NC_017769 |
| 20 | Taiwan19F-14 | 236 | 19F | brain | 2,112,148 | 2171 | NC_012469 |
| 21 | 670_6B | 90 | 6B | disease | 2,240,045 | 2393 | NC_014498 |
| 22 | 70585 | 289 | 5 | airways | 2,184,682 | 2298 | NC_012468 |
| 23 | P1031 | 303 | 1 | airways | 2,111,882 | 2223 | NC_012467 |
| 24 | gamPNI0373 | 618 | n/k | n/k | 2,064,154 | 2154 | NC_018630 |
| 25 | INV104 | 227 | 1 | disease | 2,142,122 | 2214 | NC_017591 |
| 26 | SPN032672 | 306 | n/k | n/k | 2,131,190 | 2234 | NC_021003 |
| 27 | SPN033038 | 180 | n/k | n/k | 2,133,496 | 2263 | NC_021004 |
| 28 | INV200 | 9 | 14 | disease | 2,093,317 | 2131 | NC_017593 |
| 29 | CGSP14 | 15 | 14 | pneumonia | 2,209,198 | 2233 | NC_010582 |
| 30 | ATCC_700669 | 81 | 23F | carriage | 2,221,315 | 2299 | NC_011900 |
| 31 | JJA | 66 | 14 | pneumonia | 2,120,234 | 2198 | NC_012466 |
| 32 | SC_0391 | 632 | 9 | conjunctivitis | 2,042,451 | 2042 | JFJG00000000 |
| 33 | SC_3511 | 199 | 15B | conjunctivitis | 2,027,475 | 2081 | JFJI00000000 |
| 34 | SC_3526 | 199 | 19A | conjunctivitis | 2,028,680 | 2083 | JFJJ00000000 |
| 35 | SC_0381 | 667 | 19A | conjunctivitis | 2,037,734 | 2040 | JFJF00000000 |
| 36 | TIGR4 | 205 | 4 | blood | 2,160,842 | 2230 | NC_003028 |
| 37 | R6 | 128 | NT | Laboratory | 2,038,615 | 2097 | NC_003098 |
| 38 | D39 | 128 | 2 | disease | 2,046,115 | 2105 | NC_008533 |
| 39 | G54 | 63 | 19F | airways | 2,078,953 | 2146 | NC_011072 |
| 40 | AP200 | 62 | 11A | meningitis | 2,130,580 | 2208 | NC_014494 |
| 41 | A45 | 6934 | 3 | disease | 2,129,934 | 2291 | NC_018594 |
| 42 | SPN034156 | 180 | 3 | n/k | 2,024,476 | 2097 | NC_021006 |
| 43 | SC_2441 | 180 | 3 | conjunctivitis | 2,015,741 | 2070 | JFJH00000000 |
| 44 | OXC141 | 180 | 3 | carriage | 2,036,867 | 2133 | NC_017592 |
| 45 | SPN034183 | 180 | 3 | n/k | 2,037,254 | 2150 | NC_021028 |
| 46 | SPN994039 | 180 | 3 | n/k | 2,026,505 | 2128 | NC_021005 |
| 47 | SPN994038 | 180 | 3 | n/k | 2,026,239 | 2126 | NC_021026 |

Orthogroups and Gene Families.

Orthogroups were calculated across all of the genomes in our dataset using OrthoMC[66], with a BLAST e-value of $10^{-5}$ and an inflation index of 2.5. Orthogroups contain orthologs, which are vertically inherited genes that likely have the same function, and also possibly paralogs, which are duplicated genes that may have different function.

Phylogenic and ANI Analyses.

SNP-based phylogeny based upon MLST allele sequence and single copy core alignment was generated using PhyML and statistics were calculated for 1000 bootstrap replicates[67]. To generate a MLST-based tree, DNA sequences for the seven MLST loci were concatenated and aligned for each of the 31 sequence types represented in the conjunctivitis isolates (FIG. 2) and the 26 non-ocular reference genomes (Table 2).

A phylogenetic tree of all genomes in our dataset, including the 21 genomes newly sequenced as well as 26 reference genomes (Table 2), was generated using all 1160 single-copy core orthogroups, including *Streptococcus mitis* strain B6 as an outgroup. BRAT NextGen analysis was conducted on the 1160 single-copy core orthogroup alignment of the 47 *S. pneumoniae* genomes to identify filter out recombinogenic regions[19,68]. Percent average nucleotide identity (ANI) was calculated by dividing the number of identical nucleotide residues in shared genes by the total number of nucleotides in shared genes[21]. Shared gene content between strains in pairwise genome comparisons was generated by searching the CDS predictions from one genome annotation against the annotations of the second genome and conserved genes were identified by BLAST matching >60% overall sequence identity[21].

Identification of Antibiotic Resistance Genes.

The Resfinder database was used to identify candidate antibiotic resistance genes as described previously[69]. For a subset of the isolates, susceptibility was tested in microtiter plates and minimum inhibitory concentrations (MICs) were determined by broth microdilution according to the procedure recommended by the Clinical and Laboratory Standards Institute (CLSI).

Western Blot.

Logarithmically growing cells ($OD_{600}$=0.5) were pelleted by centrifugation and subjected to lysis in 0.1% Triton X-100. To ensure equal loading, protein concentration was determined for each lysate via absorbance at 280 nm and loaded accordingly. Duplicate gels stained with Coomasie were used to confirm equivalent loading. Lysates were run on 10% NuPAGE Bis-Tris gels (Invitrogen). Proteins were subsequently transferred to PVDF membranes by Western Blot. CbpA was detected using 3 monoclonal antibodies (1:5000) in PBS-T/5% non-fat dry milk (NFDM). Monoclonal antibodies 14A3, 3G12, and 3H11, were generated as previously described and recognize the highly conserved loop regions in the R2 domain of CbpA[34]. Pneumolysin was detected using rabbit polyclonal serum generated against recombinant pneumolysin. Secondary HRP-conjugated antibodies (Biorad, Hercules, Calif.) were used at 1:5000 in PBS-T/5% NFDM.

Aggregation Assays with gp-340.

Bacterial isolates (ST448, ECC_3540; and ST199, SC_3526) were cultured over night in Todd Hewitt broth, pelleted after centrifugation (5000×g for 10 minutes), washed twice in PBS and resuspended to an optical density at $OD_{600}=0.6$ in PBS. Bacterial suspensions (300 µl) were incubated in 5 ml culture tubes in an orbital shaker at 300 RPM for 1 h at 37° C. with 0, 0.5 and 1.0 µg/ml of purified gp-340 (DMBT-1 recombinant human protein, Life Technologies). Tubes were then rested for 1 h at 37° C. to allow bacterial aggregates to settle. Gram staining was performed for each reaction to demonstrate bacterial aggregation and representative images were acquired using an Olympus BX60 microscope.

Characterization of Genes Associated with the ECC Lineage in Nasopharyngeal Genomes.

Additional genomes of nasopharyngeal isolates were analyzed for genes found in our original dataset to be specific to ECC genomes including: (a) 29 additional representatives of strains known to be associated with ECC (23 ST448, 4 SLV448, 1 ST344, 1 ST2315), (b) 19 representatives of STs closely related to those associated with ECC, (c) 44 unencapsulated STs not closely related to ECC members were analyzed, (d) 4 encapsulated STs that were most prevalent in Chewapreecha et al.[41]. This included all unencapsulated nasopharyngeal genomes in Croucher et al.[19] (16 genomes) and 8 draft genomes of nasopharyngeal isolates currently available from either the NCBI GenBank or European Nucleotide Archive (ENA), including 5 genomes newly deposited to NCBI GenBank[70]. When available, we maximized the diversity of this set by downloading several representatives, spanning various dates of isolation, or when additional information on strain diversity was available (e.g. Bayesian Analysis of Population Structure[41]). Genomes were downloaded from the ENA read archive and assembled using CLC Genomics Workbench as described above. All together an additional 96 genomes of nasopharyngeal origin were selected to serve as a local BLAST database, which was used to search (>80% query coverage, >80% nucleotide identity) for the presence of genes identified as specific to the ECC genes in our original dataset.

Example 1. Epidemiology of Conjunctivitis

Figure 1:
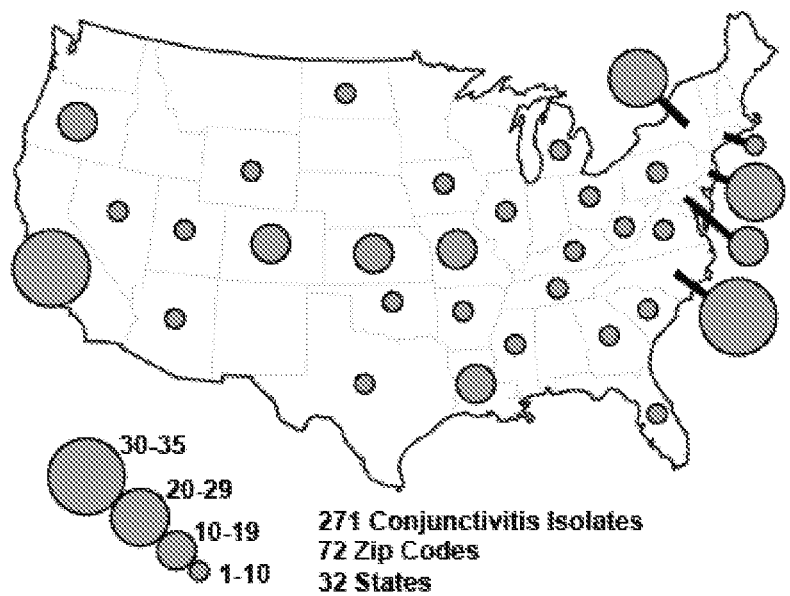
FIGS. 1A-B. Location and MLST profile of conjunctivitis isolates. 271 isolates of S. pneumoniae from diagnosed cases of conjunctivitis. (a) Number and geographic location of isolates. (b) Frequency of MLST types among conjunctivitis isolates.

To determine the diversity of S. pneumoniae causing conjunctivitis, 271 strains[-8] were characterized by MLST[16] (FIG. 1). Sequence type ST448[17,18] was found to cause the majority of infections (67.2%). The next most common types caused substantially fewer: ST344 (8.9%), ST1186 (4.8%), ST2315 (4.4%). Together, 10 different sequence types of unencapsulated S. pneumoniae accounted for 90.8% of conjunctivitis cases. A diverse set of strains of S. pneumoniae from other types of infections, for which closed genomes are available in Genbank, were included for comparison (Table 2). A distinct, deeply rooted cluster of S. pneumoniae was formed by 11 unencapsulated MLST types, encompassing 89.3% of conjunctivitis isolates (FIG. 2). Only 1 sequence type, that is encapsulated, ST199, caused more than 2 cases. This shows that although many strains of S. pneumoniae can cause conjunctivitis, this is a rare manifestation of disease caused by encapsulated strains, likely as an extension of upper respiratory infection, and instead is mainly caused by a closely related group of unencapsulated sequence types.

Example 2. Traits of the Unencapsulated Conjunctivitis Cluster

To determine whether strains of the distinct branch of S. pneumoniae associated with conjunctivitis possess novel gene content, a total of 21 genomes of representatives of the major conjunctivitis-associated sequence types were sequenced (Table 3). Diversity was maximized by selecting varying dates of isolation and sites of origin. Additionally, genomes of select encapsulated conjunctivitis strains were also sequenced, including ST199 (which caused 5 cases) and strains of sequence types ST632, ST667, ST180.

Figure 3:
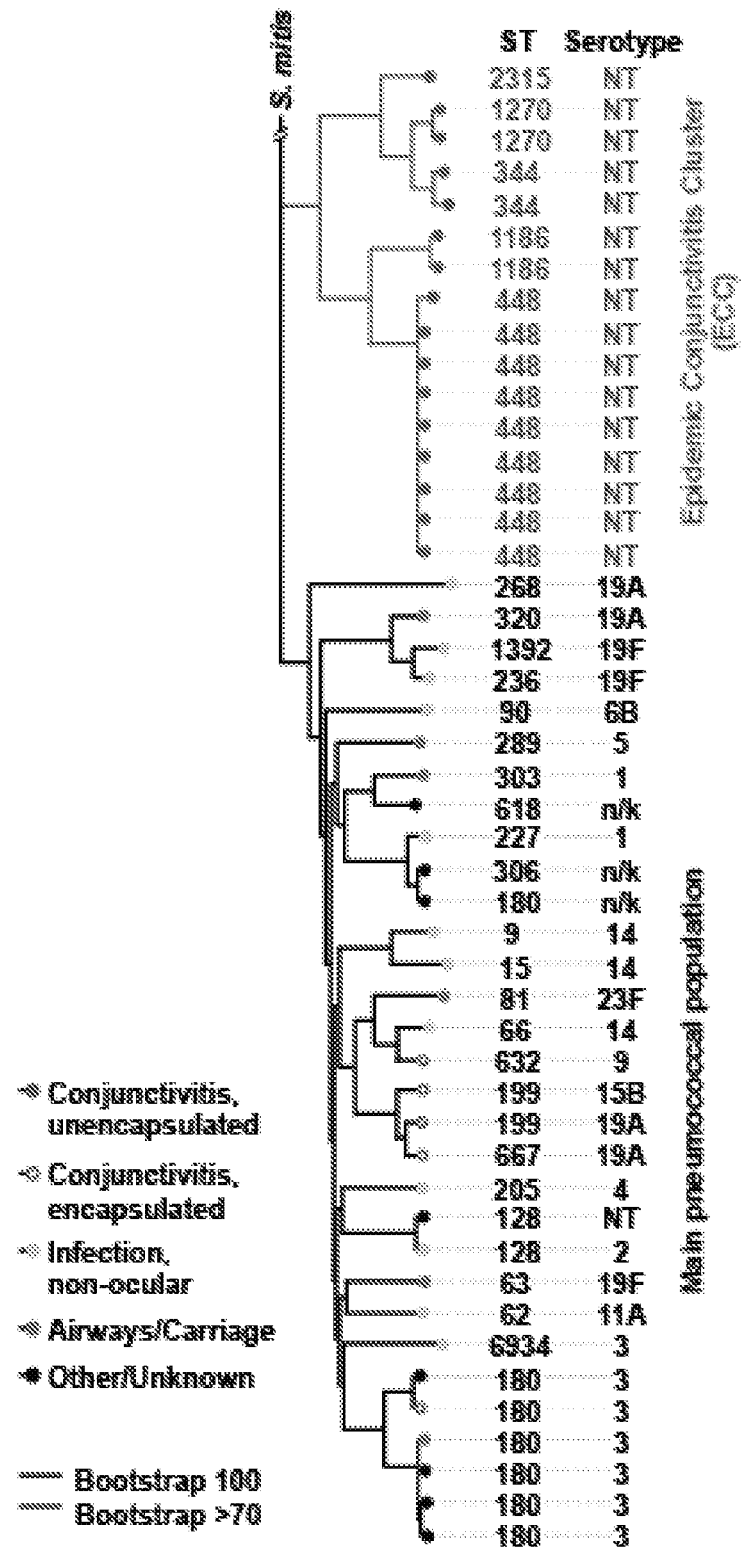
FIG. 3. Epidemic conjunctivitis clade (ECC) strains form a well resolved group of the species S. pneumoniae. A PhyML SNP-based tree based on the concatenated alignments of 1160 single copy core genes (for strain identities, see Table 2). Bootstrapping was performed with 1000 iterations.
Figure 8:
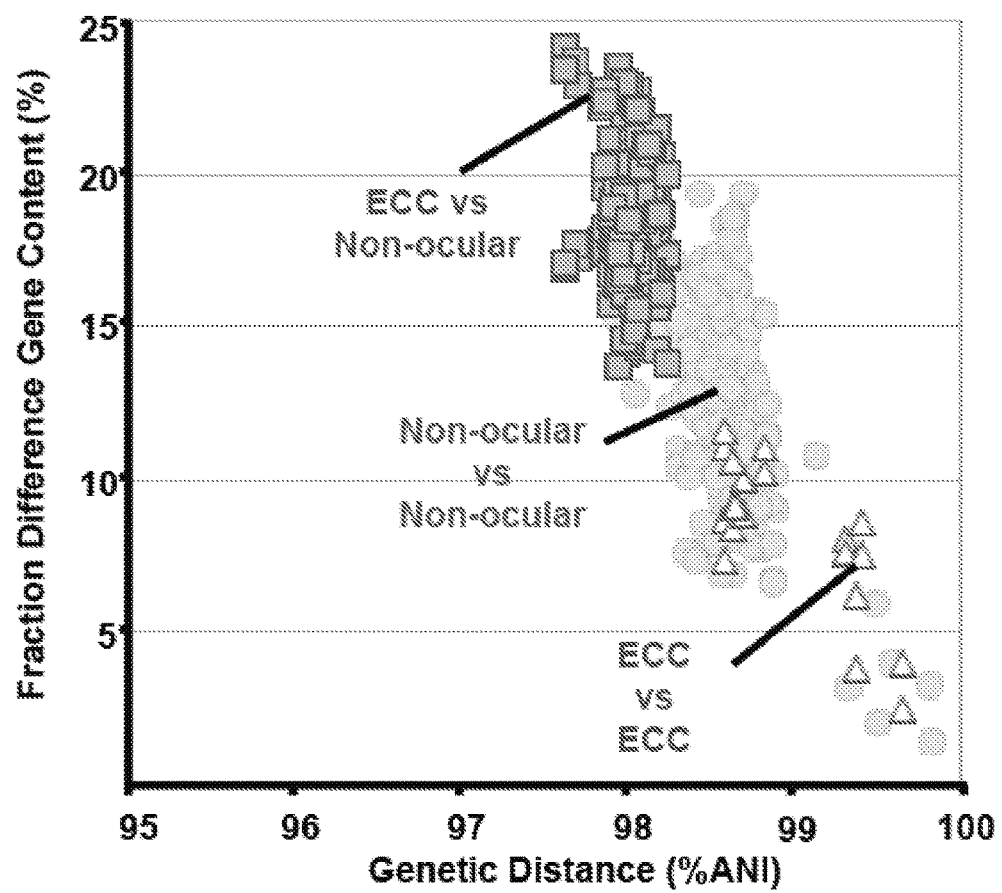
FIG. 8. Average nucleotide identity (ANI) analysis. Each point represents a pairwise comparison of two genomes.

Genes encoding a total of 4,433 protein orthogroups were identified by OrthoMCL, 1,160 of which were present in single copy in all genomes. These core orthogroup genes were used to generate a single nucleotide polymorphism (SNP) based phylogenetic tree (FIG. 3). As for MLST, the SNP based core genome tree showed that strains isolated from epidemic conjunctivitis form a distinct, deeply resolved group that includes ST448, ST1186, ST344, ST1270 and ST2315. Lineages within this group were termed the Epidemic Conjunctivitis Cluster (ECC), since their genomes are highly related and these STs (ST448, ST344, ST1186) are associated with epidemic conjunctivitis outbreaks[9,10,14,17,18]. Croucher and colleagues recently noted one group of unencapsulated strains (denoted Sequence Cluster 12 [SC12]), was the most divergent cluster from the main population in their study[19]. SC12 includes STs ST448 and ST344 associated with conjunctivitis. The phylogeny was unchanged after filtering recombinogenic regions of DNA using BRAT NextGen[20], showing that recombination was not the main driver for this population structure. Encapsulated strains that are rarer causes of conjunctivitis (ST632, ST667, ST180 and ST199) are interspersed among strains that cause infection at other sites. The extent of divergence of shared genes within ECC genomes from those of other sites of infection was quantified[21] (FIG. 8). ECC genomes compared to each other exhibit an average nucleotide identity (ANI) value of 99.0%+/−0.4, highlighting the very close relationship among ECC lineages. ECC strains are significantly more distantly related to those from other sites of infection (97.9%+/−0.11 ANI, p<0.001).

TABLE 3

Assembly statistics for S. pneumoniae conjunctivitis strains subjected to whole genome Illumina sequencing.

| Strain name | Locus tag[1] | ST | Contig Count | Reads Assembled | N50 Count | N50 Length (bp) | Longest Contig (bp) | Genome Length (bp) | % GC | Depth of Coverage | Source |
|---|---|---|---|---|---|---|---|---|---|---|---|
| ECC_0072 | | 448 | 237 | 1,489,535 | 33 | 21,024 | 97,240 | 2,107,331 | 39.69 | 71 | CDC |
| ECC_0083 | | 448 | 216 | 1,835,836 | 31 | 21,736 | 70,269 | 2,113,463 | 39.68 | 88 | CDC |
| ECC_1854 | | 448 | 242 | 2,214,325 | 31 | 22,394 | 56,945 | 2,113,718 | 39.69 | 106 | CDC |

TABLE 3-continued

Assembly statistics for *S. pneumoniae* conjunctivitis strains subjected to whole genome Illumina sequencing.

| Strain name | Locus tag[1] | ST | Contig Count | Reads Assembled | N50 Count | N50 Length (bp) | Longest Contig (bp) | Genome Length (bp) | % GC | Depth of Coverage | Source |
|---|---|---|---|---|---|---|---|---|---|---|---|
| ECC_1910 | | 448 | 308 | 1,825,838 | 41 | 14,025 | 54,596 | 2,106,050 | 39.73 | 88 | CDC |
| ECC_2439 | | 448 | 128 | 4,389,890 | 15 | 48,042 | 153,634 | 2,108,471 | 39.69 | 312 | CDC |
| ECC_2440 | | 448 | 119 | 5,021,632 | 15 | 46,929 | 153,644 | 2,126,208 | 39.69 | 319 | CDC |
| ECC_3510* | X231 | 448 | 76 | 2,777,446 | 11 | 60,698 | 140,901 | 2,126,241 | 39.64 | 328 | B&L |
| ECC_3508 | | 448 | 90 | 5,137,657 | 15 | 44,583 | 140,420 | 2,114,550 | 39.66 | 240 | B&L |
| ECC_3540 | | 448 | 88 | 3,252,701 | 15 | 44,667 | 161,742 | 2,121,720 | 39.66 | 190 | B&L |
| ECC_3435 | | 344 | 139 | 2,473,553 | 14 | 50,174 | 132,960 | 2,119,359 | 39.73 | 177 | B&L |
| ECC_3452* | BM48_ | 344 | 128 | 2,383,183 | 15 | 44,010 | 141,629 | 2,132,262 | 39.7 | 168 | B&L |
| ECC_3431 | | 1186 | 91 | 3,504,575 | 10 | 60,048 | 200,564 | 2,118,601 | 39.62 | 249 | B&L |
| ECC_3504* | BM49_ | 1186 | 73 | 3,040,540 | 9 | 74,797 | 200,562 | 2,131,110 | 39.6 | 309 | B&L |
| ECC_3502 | | 1270 | 112 | 3,296,222 | 21 | 34,782 | 121,321 | 2,151,962 | 39.65 | 319 | B&L |
| ECC_3517* | BM50_ | 1270 | 107 | 2,795,956 | 18 | 37,907 | 113,052 | 2,133,241 | 39.68 | 155 | B&L |
| ECC_3507* | BM51_ | 2315 | 96 | 4,137,247 | 18 | 40,208 | 141,463 | 2,133,084 | 39.54 | 215 | B&L |
| SC_3511 | | 199 | 53 | 7,453,201 | 9 | 84,206 | 176,218 | 2,027,475 | 39.56 | 450 | B&L |
| SC_3526 | BM52_ | 199 | 56 | 7,287,291 | 10 | 72,005 | 177,923 | 2,028,680 | 39.57 | 450 | B&L |
| SC_2441 | | 180 | 89 | 2,714,874 | 10 | 69,308 | 154,247 | 2,015,741 | 39.66 | 201 | CDC |
| SC_0381 | | 667 | 286 | 1,567,774 | 42 | 14,683 | 49,838 | 2,037,734 | 39.63 | 78 | CDC |
| SC_0391 | | 632 | 188 | 3,228,216 | 22 | 29,996 | 72,929 | 2,042,451 | 39.54 | 160 | CDC |
| | | Average | 141 ± 78 | 3,420,357 ± 1.7e6 | 19 ± 10 | 44,582 ± 20kb | 129,147 ± 47kb | 2,100,450 ± 42kb | 39.65 ± 0.06 | 223 ± 114 | |

*selected as representative genome for gene analysis
[1]NCBI gene locus_tag

Example 3. ECC Strains Possess a Distinct Gene Repertoire

Figure 9:
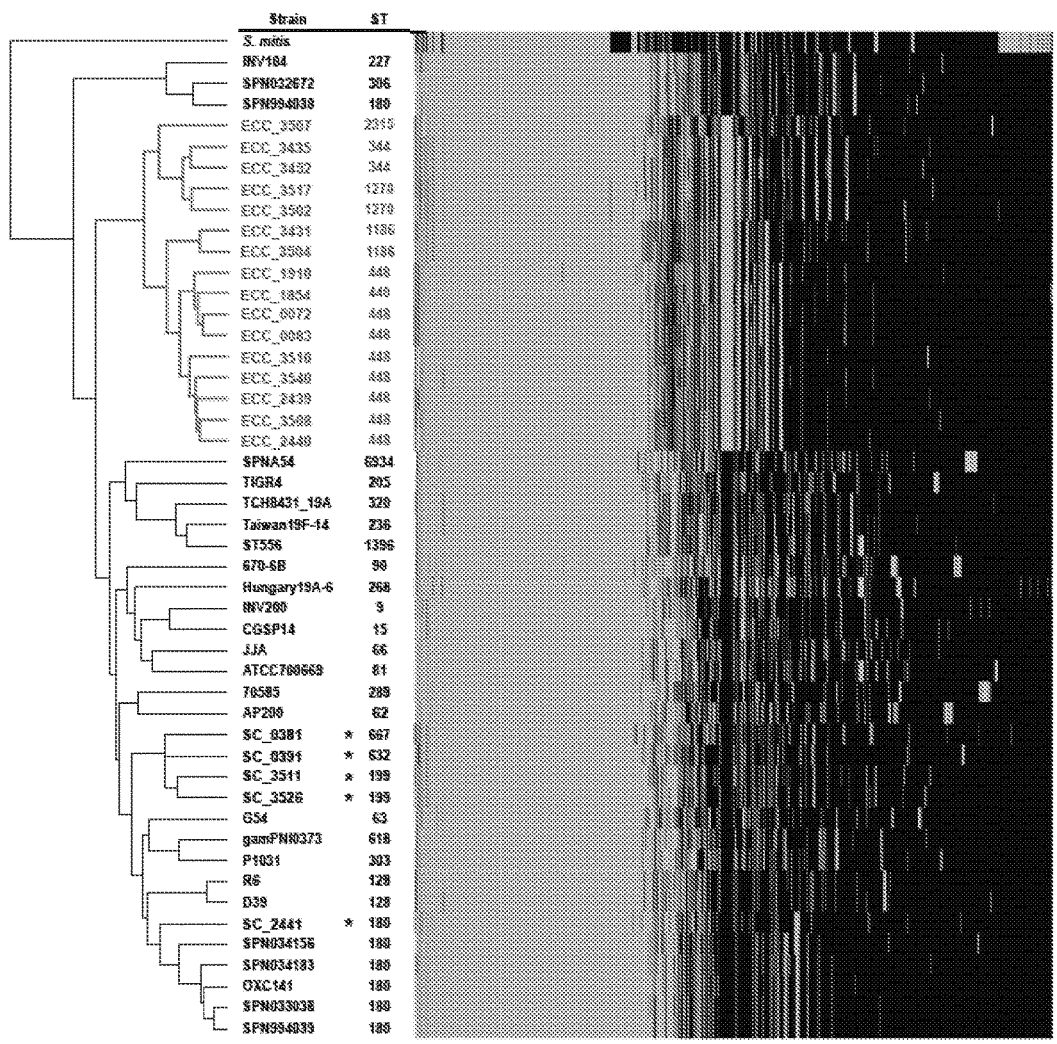
FIG. 9. Phylogenetic reconstruction based upon the pattern of gene presence and absence substantiates the divergence between ECC and non-ocular *S. pneumoniae*. Gene presence (gray line) and absence (black line) was identified across each of the genomes. Strains that are rarer causes of conjunctivitis are denoted with an asterisk.

Clustering of genomes based on similarities in gene content also places the ECC strains into a well-resolved group, independently recapitulating phylogenic structure (FIG. 9) and supporting the hypothesis that the peculiar ocular tropism of ECC strains stems at least in part from novel gene content. As in the SNP-based phylogeny, strains that are rarer causes of conjunctivitis are interspersed among non-ocular *S. pneumoniae*. To identify genes that distinguish the ECC from other strains, because horizontal gene flow can complicate the analysis, we arbitrarily set gene presence in 80% or greater of ECC genomes, and <20% of the non-ECC comparator strains (or vice versa) as the cutoff. We found 230 genes that fulfilled this enrichment criteria. Of these, 103 genes are in all ECC genomes and absent from all comparators. Conversely, 70 genes were missing from ECC that were present in 80-100% of non-ocular *S. pneumoniae* comparator genomes. Of those, 29 were found in all non-ocular genomes and no ECC strains. In patterns of gene presence and absence, encapsulated conjunctivitis strains were found to be most closely associated to those from other types of infection.

The comparatively large proportion of conjunctivitis caused by ST448 suggested that its genome may be especially refined to cause this disease (or alternatively, that among ECC lineages, ST448 was more widely distributed and abundant in nature). Seventeen orthogroups were unique to ST448, including a hypothetical mobile element with closest relative in *S. mitis*. No genes were specifically missing from ST448 that in all other ECC genomes.

Example 4. Evidence for Large Scale Surface Remodeling

Figure 4A:
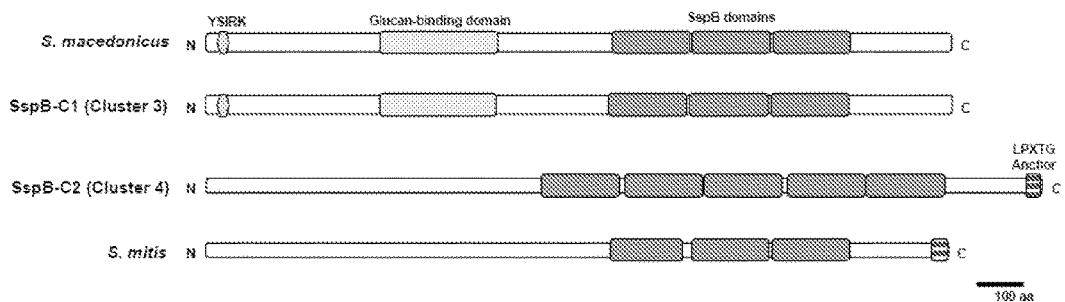
FIGS. 4A-B. Homologs of agglutinin receptors in ECC. (a) SspB-C1 and SspB-C2 agglutinins exhibit identity to glucan binding and SspB domains in orthologs from *S. macedonicus* or *S. mitis*. (b) Aggregation of ST448 (ECC_3540) and ST199 (SC_3526) isolates after addition of 0.5 µg/ml and 1.0 µg/ml of gp340 visualized by Gram staining. Scale bar represents 20 µm.
Figure 4B:
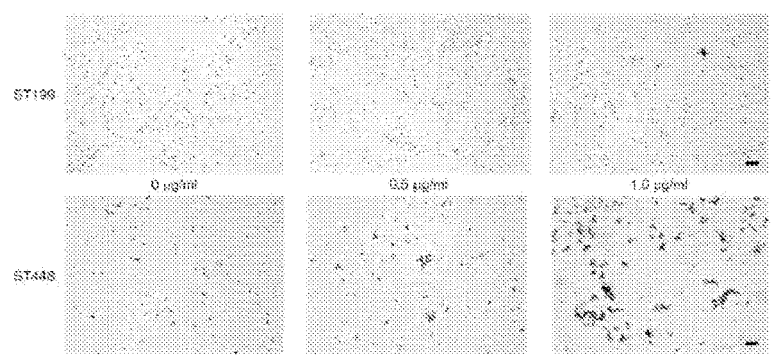

In place of a capsule operon, all ECC strains we investigated possess the atypical locus that includes aliC (X231_0947) and aliD (X231_0948), but not the often associated pspK gene[22,23]. However, in the absence of a capsule, a large number of novel surface features were found. Exclusive to ECC were two different Antigen I/II family adhesins (X231_1085 and X231_1187), that appeared to originate from *Streptococcus macedonicus* and *Streptococcus mitis* respectively (FIG. 4A). Owing to the presence of multiple SspB domains within these proteins, we termed them SspBC1 (X231_1085) and SspBC2 (X231_1187). SspB domain containing proteins have been shown to bind the human scavenger protein gp-340, which contributes to bacterial aggregation[24]. To test for this functionality, a representative ECC strain (ST448), and a non-ECC encapsulated conjunctivitis strain that lacks SspBC1 and SspBC2 (ST199), were incubated with graded concentrations gp-340. As shown in FIG. 4B, the ST448 strain exhibited gp-340 concentration dependent aggregations. We also identified a unique gene inferred to encode a surface protein (X231_1186) termed here PspO. This surface protein gene is directly adjacent to that encoding SspBC2, suggesting a potential virulence island. PspO includes a C terminal glucan-binding domain and a surface exclusion domain.

Figures 10A, 10B:
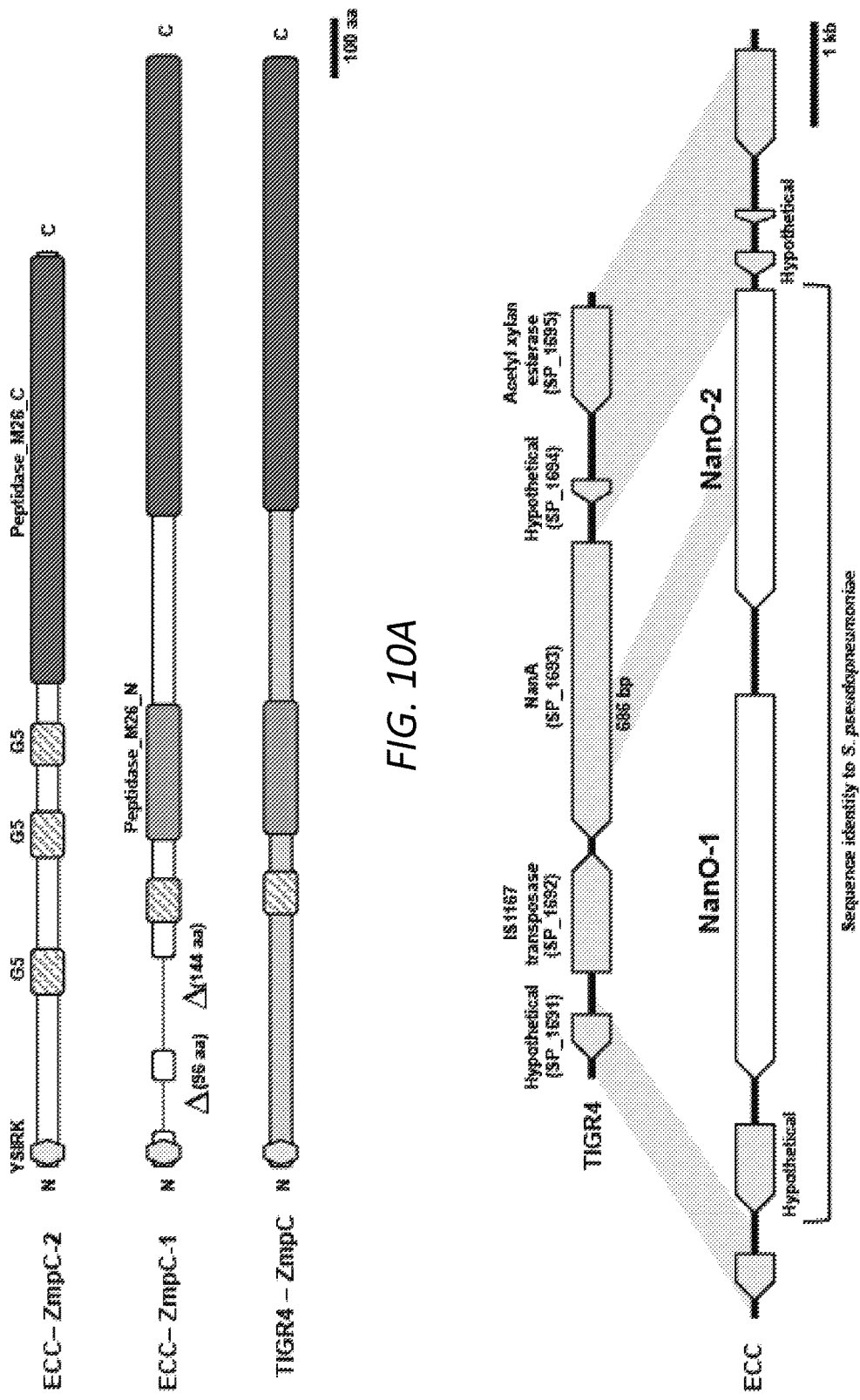
FIGS. 10A-C. ECC genomes encode unique virulence factors. Illustration of proteins unique to ECC genomes. Regions of shared identity between protein or gene sequences are shown with red highlight. (a) Domains predicted within the ZmpC1 and ZmpC2 proteins of ECC strains and ZmpC of TIGR4. Two deletions in ECC ZmpC1 compared to ZmpC of TIGR4 are shown (Δ). ZmpC comparison between conjunctivitis isolate and TIGR4 adapted from Menon et al., Microb Pathog 56, 40-46 (2013). (b) Nucleotide synteny at the nanA locus in the non-ocular reference TIGR4 and the NanO1/NanO2 sialidases encoded only within ECC strains, likely acquired by recombination with *S. pseudopneumoniae*. (c) Predicted domains encoded within the ECC sialidases NanO1 and NanO2.

Another gene predicted to affect the host/pathogen interface, that occurs exclusively in ECC strains, encodes a new divergent putative zinc metalloprotease (X231_0594), ZmpC2 (FIG. 10A). The closest ortholog is in *S. pseudopneumoniae* IS7493, and it shares 31% amino acid sequence identity with the known ZmpC of *S. pneumoniae*, mainly in the Peptidase_M26_C domain (FIG. 10A). Recently, a different, structurally related, atypical zinc metalloprotease C (zmpC, now termed ZmpC1) was identified in a *S. pneumoniae* conjunctivitis isolate, and was shown to cleave mucins from corneal epithelial cells[25,26]. ZmpC1 (X231_0222) also occurs in 100% of ECC and 0% of comparators.

Figure 10C:
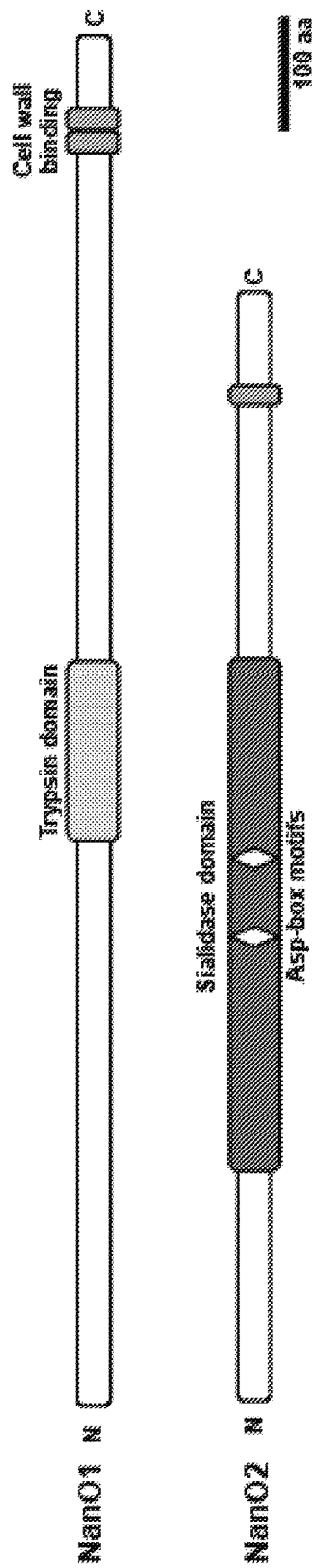

Additional surface related functions of potential relevance to conjunctivitis, include a putative sialidase (X231_0534), now termed NanO1. It shares 88% amino acid sequence identity with sialidase A (neuraminidase A) of *S. pseudopneumoniae*. The typical NanA of *S. pneumoniae*, which is carried by all non-ocular reference strains, has been displaced by NanO1 in ECC (FIG. 10B). Closer examination of the sequence surrounding nanO1 identifies a second gene, also annotated as encoding a sialidase (referred to as NanO2, X231_0533), suggesting NanO1 and NanO2 from *S. pseudopneumoniae* recombinationally displaced wild type NanA (FIG. 10C). Additionally, the neuraminidase allele NanC, found in approximately 51% of *S. pneumoniae* isolates from non-ocular sites[27], was not found within any ECC genome.

Choline binding proteins (Cbp) are important virulence factors that contribute to *S. pneumoniae* adhesion and transcytosis[28]. All ECC genomes encode a novel, divergent Cbp (BM49_0273), CbpI1, that is most closely related to a variant in *S. pseudopneumoniae*. All ECC strains also encode a second Cbp variant (X231_0220, CbpI2) that is rare outside this cluster, occurring in 3 non-ocular comparator strains (AP200, G54, TIGR4)[28]. CbpI1 and CbpI2 share a structurally related cysteine-rich secretory domain and a C-terminal choline-binding domain, and 48.3% overall amino acid sequence identity. Interestingly, CbpI2 and ZmpC1 are adjacent to one another within the ECC genomes.

Figure 5:
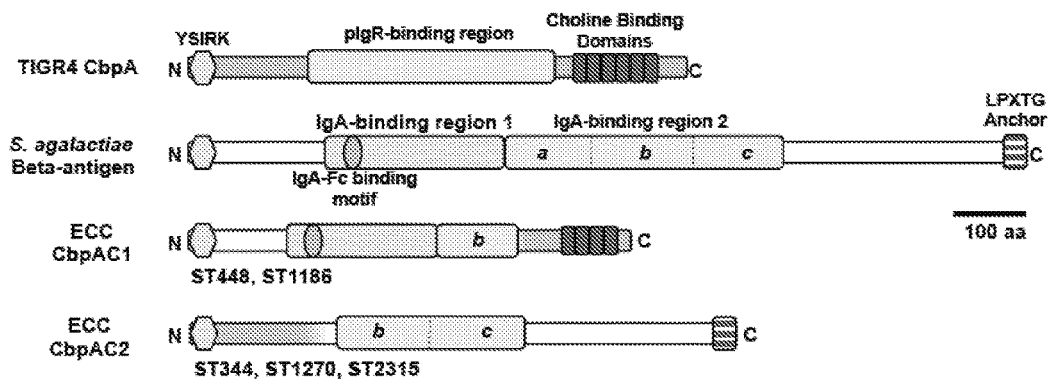
FIG. 5. ECC genomes encode an atypical CbpA. Canonical CbpA of TIGR4 compared to those in ECC genomes, and the inferred donor, *S. agalactiae* C beta-antigen. Sequence most likely deriving from *S. pneumoniae* (grey) and *S. agalactiae* (white). Domains relevant to pIgR or IgA-binding are highlighted. The IgA-binding domain of *S. agalactiae* C beta-antigen is duplicated, and domain 2 has been divided into portions (a, b, c) for purposes of illustrating the likely origins of fragments that share amino acid sequence identity in ECC variants.
Figure 11A:
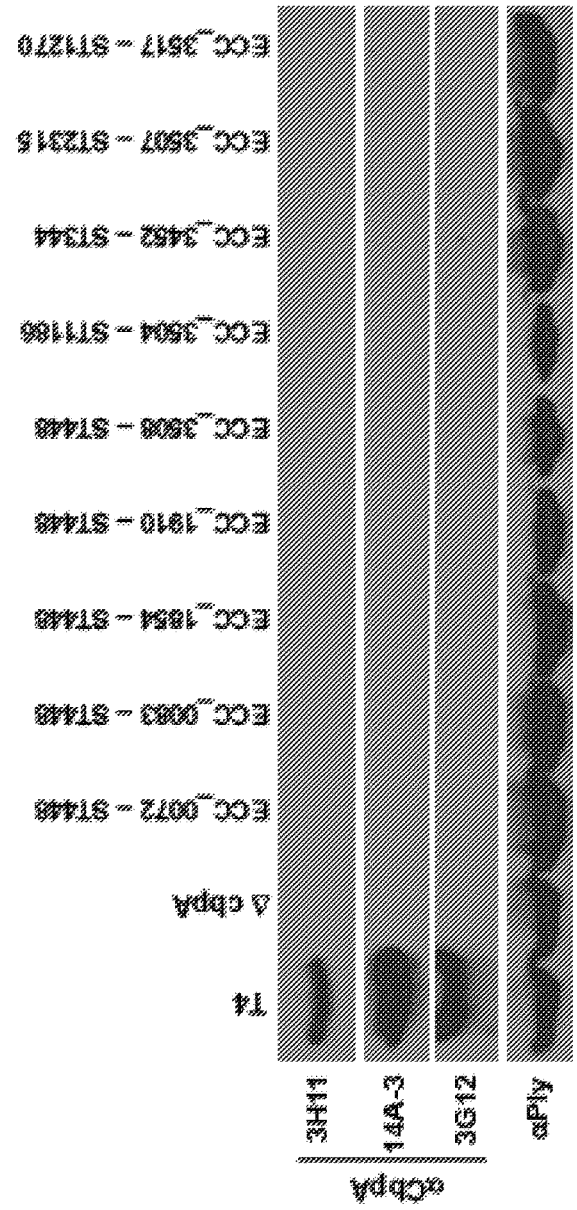
Figure 11D:
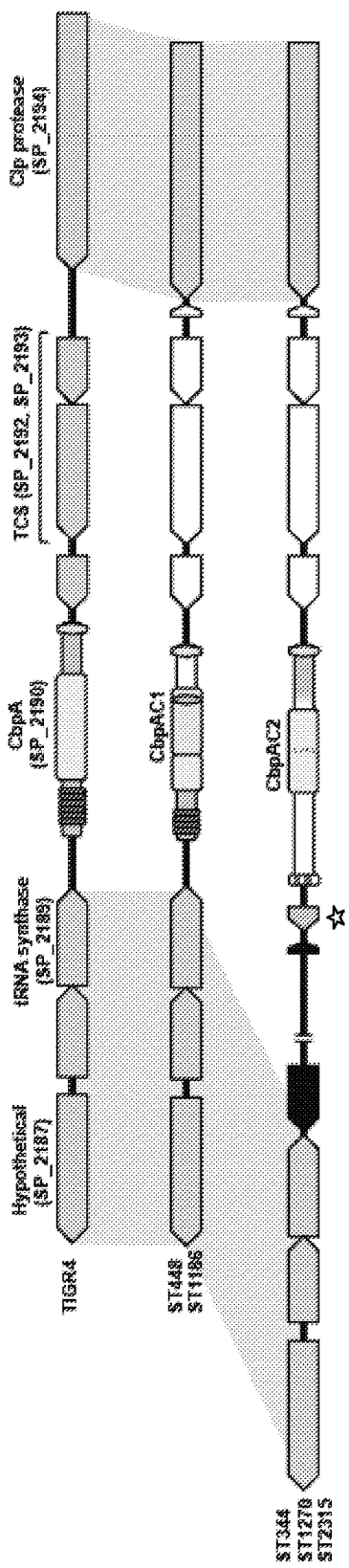

*S. pneumoniae* genes with known roles in colonization and virulence include cbpA, nanB, bgaA, strH, ply, hyl, plpA (aliA), psaABC, prtA, choP, pdgA, adr, spxB, amiA-amiF, msrA/B2, and the two Pilus Islets[29-31]. Choline binding protein A (CbpA), a main adhesin in respiratory infections and otherwise highly conserved in non-ocular strains[31,32], is substantially divergent in all ECC genomes. Two polymorphic forms of CbpA were found, CbpAC1 in ST448 and ST1186 genomes, and CbpAC2 in ST344, ST1270, and ST2315 (FIG. 5). Portions of CbpAC1 and CbpAC2 show little resemblance to CbpA, instead being closely related to the beta-antigen of *S. agalactiae*[33]. The absence of CbpA from ECC strains was verified by Western blot using three different CbpA-specific monoclonal antibodies[34], indicating that the variant CbpA possesses a substantially different structure in the otherwise conserved key epitopes probed (FIG. 11). The region of canonical CbpA that mediates binding to the eukaryotic polymeric Ig receptor (pIgR)[35], has been replaced by *S. agalactiae* domains that bind the Fc portion of IgA directly[33,36]. The different variations in the divergence of CbpAC1 and CbpAC2 from CbpA suggest that variations of the hybrid CbpA locus evolved independently. Interestingly, in ECC the two-component system that regulates CbpA expression[37], also exhibits greater nucleotide sequence identity to its counterpart in *S. agalacticae* (FIG. 11D). Differences in nucleotide sequence on either side of the two variant CbpAC loci support separate evolution of these determinants within ECC strains.

Two Pilus Islets have been described that contributing to *S. pneumoniae* epithelial cell adhesion[29,30]. Neither pilus islet occurred in any ECC strain. Exoglycosidase BgaA is absent from all ECC isolates, as is a three gene PTS system (SP_0645-SP_647) that occurs immediately adjacent bgaA in TIGR4, displaced by approximately 1 kb of sequence with high identity (>91%) to sequences in *S. mitis* and *S. pseudopneumoniae*. Otherwise, all other virulence-associated genes, including nanB, strH, ply, hyl, plpA (aliA), psaABC, prtA, choP, pdgA, adr, spxB, amiA-amiF, msrA/B2 are present in all ECC strains, and are highly conserved (99.6%+/-0.3 inferred amino acid sequence identity to TIGR4).

Example 5. Metabolic Differences

All ECC strains encode a putative phosphoenolpyruvate-dihydroxyacetone phosphotransferase system (X231_1297-X231_1300). Uniformly absent from ECC strains are operons for arginine metabolism (SP_2148-SP_2151), and a fucose binding, uptake, and catabolic pathway (SP_2158-SP_2170). This block of metabolic functions has been displaced in ECC genomes with a 12.7 kb sequence that encodes, among other things, ZmpC2. Some ECC (ST448, ST344, ST1270) lack the pia operon mediating iron uptake, which in other strains has been linked to virulence in mouse models of pulmonary and systemic infection[38]. Five other genes with putative annotations as amino acid transporters (SP_0111, SP_0112, SP_0709-SP_0711) are present in 100% of comparators, but uniformly absent in ECC, suggesting a substantially altered nutrient profile in the conjunctival mucosa.

Example 6. Recombination and HGT

The occurrence of multigene blocks of difference suggests that movement of pathogenicity islands or other mobile elements were involved in the evolution of ECC. Of the 230 orthogroups enriched in ECC, 180 genes occur in 15 clusters (Table 1). The average G+C content (36.8%+/-3.8) is lower than the rest of the genome (39.7%, $p<0.01$), which is common for mobile elements[39]. Two clusters exclusive to ECC, an 18 kb predicted phage (cluster 9) and 13 kb encoding core genes (VirD/VirB/TrsE) of a Type IV secretion system (cluster 11), are adjacent. Interestingly, the cluster 9/cluster 11 element occurs at different locations within ECC STs, suggesting either independent acquisition, or internal movement. That it is mobile and presumably could be lost if not for selection, yet is retained, suggests that it may have a role in mediating the peculiar ocular tropism of ECC.

Figure 12:
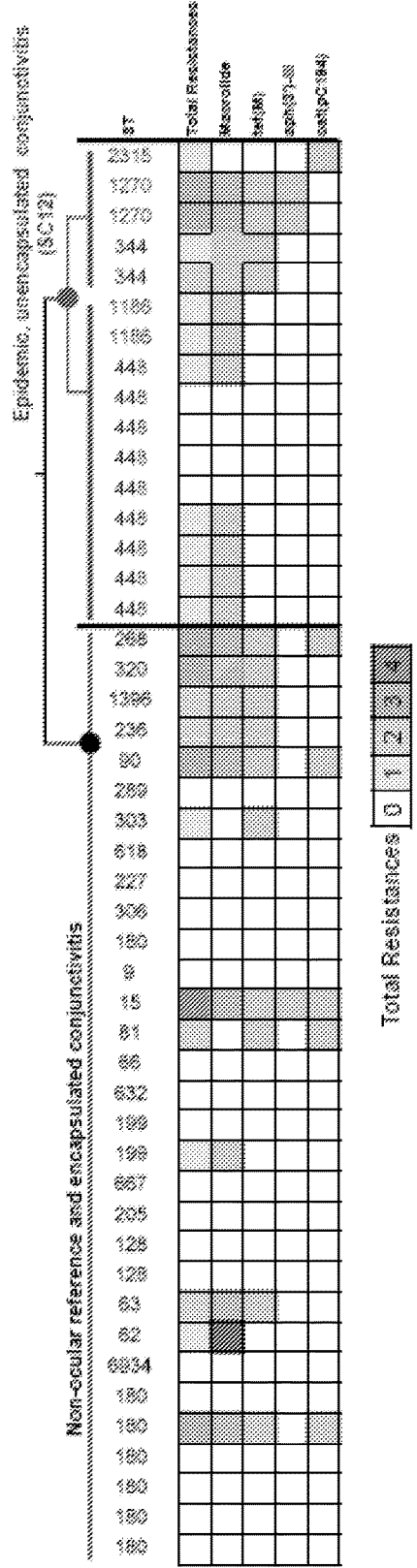
FIG. 12. Summary of resistance genes. Each box represents a strain. Specific organization of the strains within the tree can be found in FIG. 3 and Table 2. Macrolide resistances: mef/mel (gray), ermB (green), and ermA (blue).
Figure 13D:
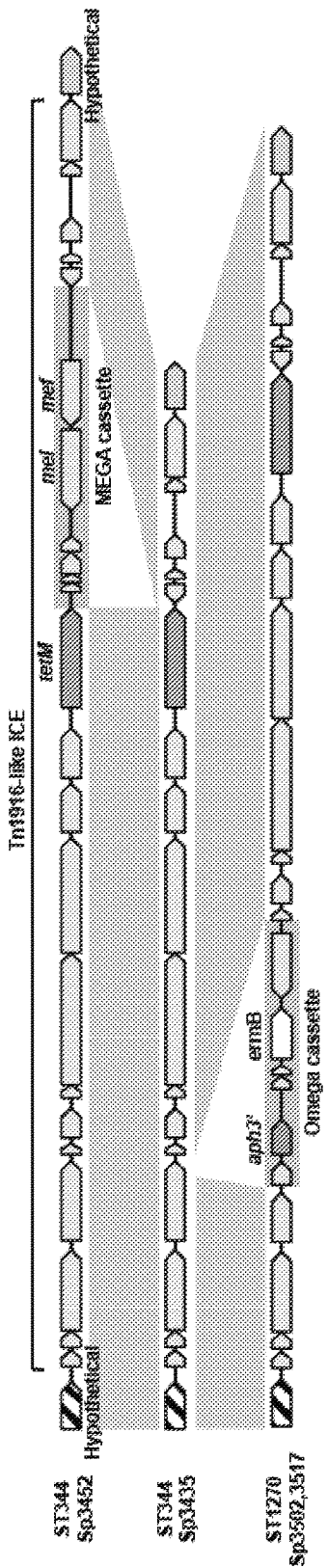
Figure 13E:
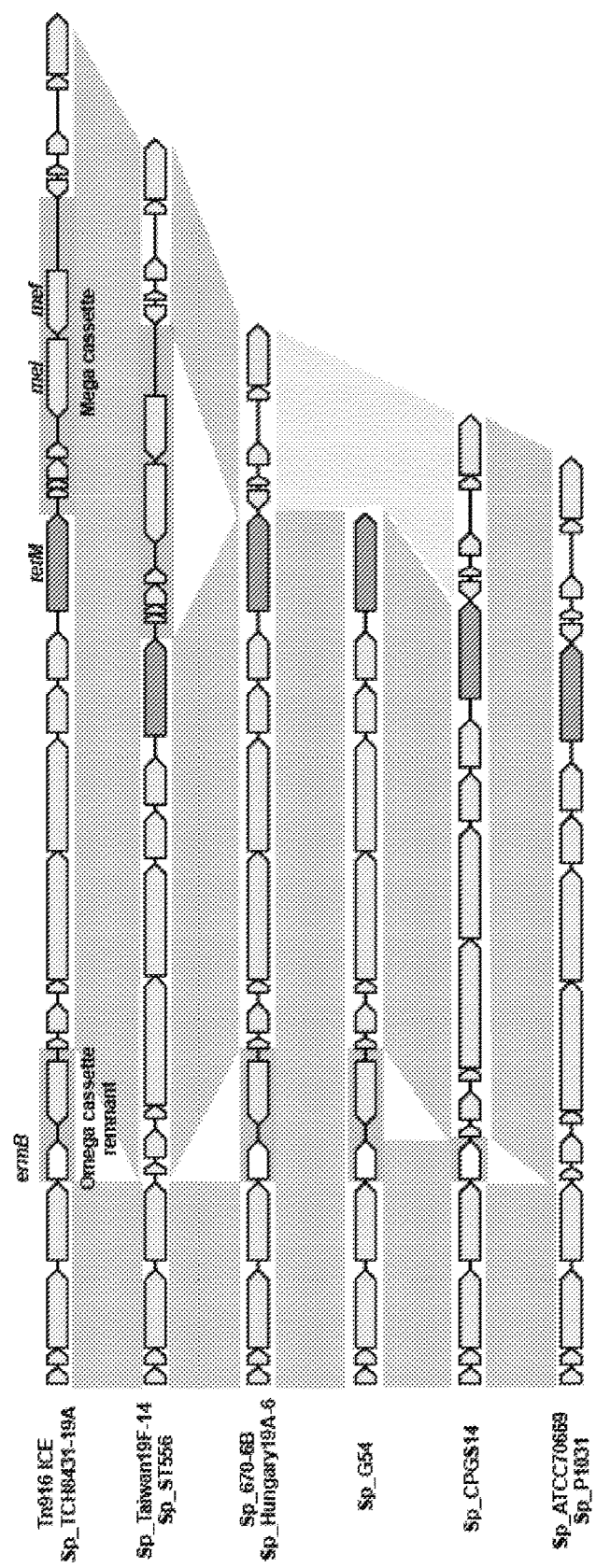

The majority (75%) of ECC carry resistance elements (FIG. 12) consistent with antibiotic susceptibility[40]. Macrolide resistance is the most common, and conferred by the Macrolide Efflux Genetic Assembly (MEGA) cassette in ST448 and ST1186, and by a Tn916-like integrative conjugative element (ICE) in ST344 and ST1270 (FIG. 13). ST2315 was the only ECC isolate resistant to phenicols, which was conferred by an Spn11930-like ICE element.

TABLE 1

Gene clusters enriched in ECC genomes.

| Cluster[1] | Putative Function[2] | Putative Origin[3] | Size (kb) | % GC |
|---|---|---|---|---|
| 2 | Atypical capsule locus of NT pneumococci | *S. pneumoniae* | 6.1 | 37.9 |
| 5 | ZmpC1 specific to conjunctivitis genomes, CbpI2 | *S. pneumoniae* | 11.4 | 38.3 |
| 14 | ZmpC2 | *S. pseudopneumoniae* | 10.2 | 40.1 |
| 3 | SspBC1 Agglutinin receptor | *S. macedonicus* | 15.4 | 40.8 |
| 4 | SspBC2 Agglutinin receptor from *S. mitis*, Unknowns from *S. oligofermentans*[a] | *S. mitis*, *S. oligofermentans* | 17.7 | 36.4 |

TABLE 1-continued

Gene clusters enriched in ECC genomes.

| Cluster[1] | Putative Function[2] | Putative Origin[3] | Size (kb) | % GC |
|---|---|---|---|---|
| 10 | Mobile Genetic Element[a] | S. oligofermentans | 16.8 | 35.9 |
| 9 | Phage[b] | non-S. pneumoniae, Streptococcus sp. | 18.7 | 37.0 |
| 11 | Mobile Genetic Element containing putative Type IV secretory system genes[b] | S. macedonicus | 13.2 | 42.6 |
| 8 | Metabolic cassette, triose metabolism | S. pneumoniae | 4.4 | 38.3 |
| 1 | Phage element, intact, containing toxin/antitoxin in ST448/ST1186 | S. pneumoniae | 33.4 | 39.4 |
| 6 | Lanthionine biosynthesis genes and unknowns from S. oralis | S. oralis, 5', 4.6 kb/ S. pneumoniae, 3' | 16.2 | 29.9 |
| 7 | ABC-type transport system | S. pneumoniae | 4.5 | 38.0 |
| 15 | Phage element | S. pneumoniae | 10.1 | 36.6 |
| 12 | Unknown | S. pneumoniae | 4.7 | 29.2 |
| 13 | Unknown | S. parasanguinis | 1.7 | 32.2 |

[1]The very high quality ST448 strain ECC_3510 genome was arbitrarily selected to identify patterns of clustering among the genes of difference in ECC strains. A cluster is defined as 2 or more contiguous genes.
[2]Refer to Table S4 for full list of genes associated with each cluster.
[3]Based on highest BLAST result on nucleotide sequence.
[a,b]Clusters that are not found on a single contig, but could be linked together by synteny analysis versus a closed reference genome.

Example 7. Comparison to Strains Identified in Asymptomatic Carriage

Asymptomatic nasopharyngeal carriage generally precedes disease. To determine whether ECC strains were represented in large data sets from asymptomatic carriage, we looked for their occurrence in two recently reported studies[19,41]. This expanded analysis substantiates the deeply rooted and well-clustered grouping of the ECC strains, but importantly, shows that ECC STs are distributed among additional closely related, unencapsulated strains isolated from the nasopharynges that have not yet been associated with conjunctivitis (FIG. 6). It was thus of interest to compare the traits of ECC strains isolated from conjunctivitis to those isolated from the nasopharynx by investigating the presence or absence of a selection of newly identified ECC genes with a putative contribution to conjunctivitis pathogenesis. From the asymptomatic carriage data sets, we selected genome sequences of 96 strains that were of sequence types closely related to those that constituted the ECC group; and also diverse strains spread across the phylogenetic tree representing the most prevalent STs associated with nasopharyngeal carriage regardless of their encapsulation status (FIG. 6, FIG. 4). All genes found to be enriched in ECC strains isolated from conjunctivitis were also found to be present within nasopharyngeal isolates of ST448, ST2315, ST344 genomes, indicating these strains are highly similar to those isolated from conjunctivitis, and supporting an infection model where asymptomatic carriage in the nasopharynx precedes ocular infection. Of the cumulative 3,701 nasopharyngeal isolates represented in the two nasopharyngeal surveys, no representatives of ST1186 or ST1270 were observed, in contrast to their occurrence at rates of 13/271 (4.8%) and 3/271 (1.1%) respectively in conjunctivitis cases, indicating their rarity among the circulating population despite their enrichment in cases of conjunctivitis.

Genes we identified as enriched in ECC strains isolated from conjunctivitis, cbpAC1, cbpAC2, and nanO1/nanO2 were only found to occur among asymptomatic carriage strains of the same sequence types. Other genes we found enriched in ECC (sspBC1, sspBC2, zmpC1, zmpC2) occurred also in unencapsulated lineages that have not yet been observed in conjunctivitis, and the majority of these lineages are closely related phylogenetically to ECC strains (FIG. 6). Interestingly, some sequence types phylogenetically closely related to ECC strains (ST5126, ST4142, ST4139) were found to lack all ECC genes that were investigated. As these STs were not identified among conjunctivitis strains, their ability to cause this disease remains unknown.

REFERENCES

1 Tuomanen, E. I., Austrian, R. & Masure, H. R. Pathogenesis of pneumococcal infection. *N Engl J Med* 332, 1280-1284 (1995).
2 Vernatter, J. & Pirofski, L. A. Current concepts in host-microbe interaction leading to pneumococcal pneumonia. *Curr Opin Infect Dis* 26, 277-283 (2013).
3 Farrell, D. J., Klugman, K. P. & Pichichero, M. Increased antimicrobial resistance among nonvaccine serotypes of *Streptococcus pneumoniae* in the pediatric population after the introduction of 7-valent pneumococcal vaccine in the United States. *Pediatr Infect Dis J* 26, 123-128 (2007).
4 Buznach, N., Dagan, R. & Greenberg, D. Clinical and bacterial characteristics of acute bacterial conjunctivitis in children in the antibiotic resistance era. *Pediatr Infect Dis J* 24, 823-828 (2005).
5 Karpecki, P. et al. Besifloxacin ophthalmic suspension 0.6% in patients with bacterial conjunctivitis: A multicenter, prospective, randomized, double-masked, vehicle-controlled, 5-day efficacy and safety study. *Clin Ther* 31, 514-526 (2009).
6 McDonald, M. B. et al. Efficacy and safety of besifloxacin ophthalmic suspension 0.6% compared with moxifloxacin ophthalmic solution 0.5% for treating bacterial conjunctivitis. *Ophthalmology* 116, 1615-1623 e1611 (2009).
7 Tepedino, M. E. et al. Phase III efficacy and safety study of besifloxacin ophthalmic suspension 0.6% in the treatment of bacterial conjunctivitis. *Curr Med Res Opin* 25, 1159-1169 (2009).
8 Haas, W., Hesje, C. K., Sanfilippo, C. M. & Morris, T. W. High proportion of nontypeable *Streptococcus pneumo-*

9 niae isolates among sporadic, nonoutbreak cases of bacterial conjunctivitis. *Curr Eye Res* 36, 1078-1085 (2011).
9 Buck, J. M. et al. A community outbreak of conjunctivitis caused by nontypeable *Streptococcus pneumoniae* in Minnesota. *Pediatr Infect Dis J* 25, 906-911 (2006).
10 Martin, M. et al. An outbreak of conjunctivitis due to atypical *Streptococcus pneumoniae*. *N Engl J Med* 348, 1112-1121 (2003).
11 Shayegani, M., Parsons, L. M., Gibbons, W. E., Jr. & Campbell, D. Characterization of nontypable *Streptococcus pneumoniae*-like organisms isolated from outbreaks of conjunctivitis. *J Clin Microbiol* 16, 8-14 (1982).
12 (CDC), C. f. D. C. a. P. Outbreak of bacterial conjunctivitis at a college—New Hampshire, January-March, 2002. *MMWR Morb Mortal Wkly Rep* 51, 205-207 (2002).
13 (CDC), C. f. D. C. a. P. Pneumococcal conjunctivitis at an elementary school—Maine, Sep. 20-Dec. 6, 2002. *MMWR Morb Mortal Wkly Rep* 52, 64-66 (2003).
14 Crum, N. F., Barrozo, C. P., Chapman, F. A., Ryan, M. A. & Russell, K. L. An outbreak of conjunctivitis due to a novel unencapsulated *Streptococcus pneumoniae* among military trainees. *Clin Infect Dis* 39, 1148-1154 (2004).
15 Hanage, W. P., Kaijalainen, T., Saukkoriipi, A., Rickcord, J. L. & Spratt, B. G. A successful, diverse disease-associated lineage of nontypeable pneumococci that has lost the capsular biosynthesis locus. *J Clin Microbiol* 44, 743-749 (2006).
16 Enright, M. C. & Spratt, B. G. A multilocus sequence typing scheme for *Streptococcus pneumoniae*: identification of clones associated with serious invasive disease. *Microbiology* 144 (Pt 11), 3049-3060 (1998).
17 Zegans, M. E. et al. Clinical features, outcomes, and costs of a conjunctivitis outbreak caused by the ST448 strain of *Streptococcus pneumoniae*. *Cornea* 28, 503-509 (2009).
18 Marimon, J. M., Ercibengoa, M., Garcia-Arenzana, J. M., Alonso, M. & Perez-Trallero, E. *Streptococcus pneumoniae* ocular infections, prominent role of unencapsulated isolates in conjunctivitis. *Clin Microbiol Infect* 19, E298-305 (2013).
19 Croucher, N. J. et al. Population genomics of post-vaccine changes in pneumococcal epidemiology. *Nat Genet* 45, 656-663 (2013).
20 Marttinen, P. et al. Detection of recombination events in bacterial genomes from large population samples. *Nucleic Acids Res* 40, e6 (2012).
21 Konstantinidis, K. T. & Tiedje, J. M. Genomic insights that advance the species definition for prokaryotes. *Proc Natl Acad Sci USA* 102, 2567-2572 (2005).
22 Keller, L. E. et al. PspK of *Streptococcus pneumoniae* increases adherence to epithelial cells and enhances nasopharyngeal colonization. *Infect Immun* 81, 173-181 (2013).
23 Park, I. H. et al. Nontypeable pneumococci can be divided into multiple cps types, including one type expressing the novel gene pspK. *MBio* 3 (2012).
24 Jakubovics, N. S., Stromberg, N., van Dolleweerd, C. J., Kelly, C. G. & Jenkinson, H. F. Differential binding specificities of oral streptococcal antigen I/II family adhesins for human or bacterial ligands. *Mol Microbiol* 55, 1591-1605 (2005).
25 Govindarajan, B. et al. A metalloproteinase secreted by *Streptococcus pneumoniae* removes membrane mucin MUC16 from the epithelial glycocalyx barrier. *PLoS One* 7, e32418 (2012).
26 Menon, B. B. & Govindarajan, B. Identification of an atypical zinc metalloproteinase, ZmpC, from an epidemic conjunctivitis-causing strain of *Streptococcus pneumoniae*. *Microb Pathog* 56, 40-46 (2013).
27 Pettigrew, M. M., Fennie, K. P., York, M. P., Daniels, J. & Ghaffar, F. Variation in the presence of neuraminidase genes among *Streptococcus pneumoniae* isolates with identical sequence types. *Infect Immun* 74, 3360-3365 (2006).
28 Gosink, K. K., Mann, E. R., Guglielmo, C., Tuomanen, E. I. & Masure, H. R. Role of novel choline binding proteins in virulence of *Streptococcus pneumoniae*. *Infect Immun* 68, 5690-5695 (2000).
29 Bagnoli, F. et al. A second pilus type in *Streptococcus pneumoniae* is prevalent in emerging serotypes and mediates adhesion to host cells. *J Bacteriol* 190, 5480-5492 (2008).
30 Hilleringmann, M. et al. Molecular architecture of *Streptococcus pneumoniae* TIGR4 pili. *Embo J* 28, 3921-3930 (2009).
31 Mook-Kanamori, B. B., Geldhoff, M., van der Poll, T. & van de Beek, D. Pathogenesis and pathophysiology of pneumococcal meningitis. *Clin Microbiol Rev* 24, 557-591 (2011).
32 Luo, R. et al. Solution structure of choline binding protein A, the major adhesin of *Streptococcus pneumoniae*. *Embo J* 24, 34-43 (2005).
33 Jerlstrom, P. G., Chhatwal, G. S. & Timmis, K. N. The IgA-binding beta antigen of the c protein complex of Group B streptococci: sequence determination of its gene and detection of two binding regions. *Mol Microbiol* 5, 843-849 (1991).
34 Mann, B. et al. Broadly Protective Protein-Based Pneumococcal Vaccine Composed of Pneumolysin Toxoid-CbpA Peptide Recombinant Fusion Protein. *J Infect Dis* 209(7):1116-25 (2014).
35 Zhang, J. R. et al. The polymeric immunoglobulin receptor translocates pneumococci across human nasopharyngeal epithelial cells. *Cell* 102, 827-837 (2000).
36 Jerlstrom, P. G., Talay, S. R., Valentin-Weigand, P., Timmis, K. N. & Chhatwal, G. S. Identification of an immunoglobulin A binding motif located in the beta-antigen of the c protein complex of group B streptococci. *Infect Immun* 64, 2787-2793 (1996).
37 Rosch, J. W., Mann, B., Thornton, J., Sublett, J. & Tuomanen, E. Convergence of regulatory networks on the pilus locus of *Streptococcus pneumoniae*. *Infect Immun* 76, 3187-3196 (2008).
38 Brown, J. S., Gilliland, S. M., Spratt, B. G. & Holden, D. W. A locus contained within a variable region of pneumococcal pathogenicity island 1 contributes to virulence in mice. *Infect Immun* 72, 1587-1593 (2004).
39 Frost, L. S., Leplae, R., Summers, A. O. & Toussaint, A. Mobile genetic elements: the agents of open source evolution. *Nat Rev Microbiol* 3, 722-732 (2005).
40 Haas, W., Gearinger, L. S., Hesje, C. K., Sanfilippo, C. M. & Morris, T. W. Microbiological etiology and susceptibility of bacterial conjunctivitis isolates from clinical trials with ophthalmic, twice-daily besifloxacin. *Adv Ther* 29, 442-455 (2012).
41 Chewapreecha, C. et al. Dense genomic sampling identifies highways of pneumococcal recombination. *Nat Genet* (2014).
42 Konstantinidis, K. T., Ramette, A. & Tiedje, J. M. The bacterial species definition in the genomic era. *Philos Trans R Soc Lond B Biol Sci* 361, 1929-1940 (2006).
43 Michel, J. L., Madoff, L. C., Kling, D. E., Kasper, D. L. & Ausubel, F. M. Cloned alpha and beta C-protein antigens of group B streptococci elicit protective immunity. *Infect Immun* 59, 2023-2028 (1991).
44 Kim, H. K., Thammavongsa, V., Schneewind, O. & Missiakas, D. Recurrent infections and immune evasion strategies of *Staphylococcus aureus*. *Curr Opin Microbiol* 15, 92-99 (2012).
45 Fagan, P. K., Reinscheid, D., Gottschalk, B. & Chhatwal, G. S. Identification and characterization of a novel secreted immunoglobulin binding protein from group A streptococcus. *Infect Immun* 69, 4851-4857 (2001).
46 Lofling, J., Vimberg, V., Battig, P. & Henriques-Normark, B. Cellular interactions by LPxTG-anchored pneumococcal adhesins and their streptococcal homologues. *Cell Microbiol* 13, 186-197 (2011).
47 Wells, P. A. & Hazlett, L. D. Complex carbohydrates at the ocular surface of the mouse: an ultrastructural and cytochemical analysis. *Exp Eye Res* 39, 19-35 (1984).
48 Hazlett, L. D., Moon, M. & Berk, R. S. In vivo identification of sialic acid as the ocular receptor for *Pseudomonas aeruginosa*. *Infect Immun* 51, 687-689 (1986).
49 Royle, L. et al. Glycan structures of ocular surface mucins in man, rabbit and dog display species differences. *Glycoconj J* 25, 763-773 (2008).
50 Donati, C. et al. Structure and dynamics of the pan-genome of *Streptococcus pneumoniae* and closely related species. *Genome Biol* 11, R107 (2010).
51 Brady, L. J. et al. The changing faces of *Streptococcus* antigen I/II polypeptide family adhesins. *Mol Microbiol* 77, 276-286 (2010).
52 Jumblatt, M. M. et al. Glycoprotein 340 in normal human ocular surface tissues and tear film. *Infect Immun* 74, 4058-4063 (2006).
53 Carrolo, M., Frias, M. J., Pinto, F. R., Melo-Cristino, J. & Ramirez, M. Prophage spontaneous activation promotes DNA release enhancing biofilm formation in *Streptococcus pneumoniae*. *PLoS One* 5, e15678 (2010).
54 Sachedina, S., Greiner, J. V. & Glonek, T. Phosphatic intermediate metabolites of the porcine ocular tunica fibrosa. *Exp Eye Res* 52, 253-260 (1991).
55 Pacheco, A. R. et al. Fucose sensing regulates bacterial intestinal colonization. *Nature* 492, 113-117 (2012).
56 Stahl, M. et al. L-fucose utilization provides *Campylobacter jejuni* with a competitive advantage. *Proc Natl Acad Sci USA* 108, 7194-7199 (2011).
57 Isnard, N., Bourles-Dagonet, F., Robert, L. & Renard, G. Studies on corneal wound healing. Effect of fucose on iodine vapor-burnt rabbit corneas. *Ophthalmologica* 219, 324-333 (2005).
58 Croucher, N. J. et al. Rapid pneumococcal evolution in response to clinical interventions. *Science* 331, 430-434 (2011).
59 Lebreton, F. et al. Emergence of epidemic multidrug-resistant *Enterococcus faecium* from animal and commensal strains. *MBio* 4 (2013).
60 Weinert, L. A. et al. Molecular dating of human-to-bovid host jumps by *Staphylococcus aureus* reveals an association with the spread of domestication. *Biol Lett* 8, 829-832 (2012).
61 Maiden, M. C. et al. Multilocus sequence typing: a portable approach to the identification of clones within populations of pathogenic microorganisms. *Proc Natl Acad Sci USA* 95, 3140-3145 (1998).
62 Sanfilippo, C. M., Haas, W., Hesje, C. K. & Morris, T. W. in *Association for Research in Vision and Ophthalmology* (*ARVO*) (Fort Lauderdale, Fla., 2012).
63 Aziz, R. K. et al. The RAST Server: rapid annotations using subsystems technology. *BMC Genomics* 9, 75 (2008).
64 Delcher, A. L., Harmon, D., Kasif, S., White, O. & Salzberg, S. L. Improved microbial gene identification with GLIMMER. *Nucleic Acids Res* 27, 4636-4641 (1999).
65 Finn, R. D. et al. The Pfam protein families database. *Nucleic Acids Res* 36, D281-288 (2008).
66 Li, L., Stoeckert, C. J., Jr. & Roos, D. S. OrthoMCL: identification of ortholog groups for eukaryotic genomes. *Genome Res* 13, 2178-2189 (2003).
67 Guindon, S. et al. New algorithms and methods to estimate maximum-likelihood phylogenies: assessing the performance of PhyML 3.0. *Syst Biol* 59, 307-321 (2010).
68 Corander, J., Waldmann, P., Marttinen, P. & Sillanpaa, M. J. BAPS 2: enhanced possibilities for the analysis of genetic population structure. *Bioinformatics* 20, 2363-2369 (2004).
69 Zankari, E. et al. Identification of acquired antimicrobial resistance genes. *J Antimicrob Chemother* 67, 2640-2644 (2012).
70 Keller, L. E. et al. Draft Genome Sequences of Five Multilocus Sequence Types of Nonencapsulated *Streptococcus pneumoniae*. *Genome Announc* 1 (2013).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

```
>SspBC1 (X231_1085)
                                                                    (SEQ ID NO: 1)
MLLLIKRKEGLFMTKQCHHHFLVNQEQAEKHVFRKSKKYRTLCSVALGTMVTAVVAWGGQVAQADEVTMPPLDKTVQLTENNAT

NLPEAQPAPVAEQTDSLFSTGQSDGTITVTVPHDTVTNAINQATAEGLTTIQDKPMDLGNTTSASETSKQLDTAEADAAKQAED

ITRVTNTYKADKVAYEQDKTRVEKGNAALVASHKEATQAGKALNSSVDTTASEVKTQDKSANVTITTQTVPSGEGSTVSGYQDY

TSAVAAIDKQNKASLADYITKKQAADAITAKNLAVQKENEAGLANAKAENEAITKRNQAGQKAIDDENKAGQAAVDTYNKNQQK

LVTDREDEIAAIIKRNKEKEEAAKKENEAIDAYNAKEMNRYKRDLADISKGEEGYISQALAQALNLNNGEPQARHSADTRNPNR

IIAKGDAMLGGYSKILDSTGFFVYDTFKTGETLSFTYQNLQNASFDGKKITKVAYDITNLVSPTGTDSVQLVVPNDPTEGFIAY

RNDGTGNWRTDKMEFRVKAKYFLEDGSQVSFTKEKPGVFTHSSLNHNDIGLEYVKDTSGKFVPINGSTIQVTDEDLARSLSSNR
```

-continued

ASDLNLPEEWDTSFSKYAYKGAIVSTVTSGNTYTVTFGQGDMPQNAGLTYWFALNTLPVARTVKPYSPKPHVTPKLDPVPEPIK

VVPKTFTPKTFTPEPPVIFKEKPLEKVTQPRLTLTKVTFAKEPRSEPLPKAPQVPTVHYHDYRLTTTPEIMKKVVNTDQDNLHD

KTIAKDSTVIYPLTVDVFSSNRAKTTTLTFEDYLPAGYAFDKEKTQAENENYTLTFDEAKNFVTLTAKEALLQEVNQDLTKSYQ

LVAPKLYGSLQNDGATYSNSYKLLINKGTSNAYTVTSNVVTVRTPGDGKITSRITPQKRNENEDGVVINDTVVALGTTNHYRLT

WDLDQYKGDTSSKETIARGFFFVDDYPEEVLDLVDKGTSITTLDGKAVSGITVKAYVSLSEAPKDLQDKLAHAKISPKGAFQIF

QPNDNQAFYDQYVKTGTSLNLLTKMTVKDSLYGQTKTYRNKAYQVDFGNGYKTNEVTNTLVSPTPKKQNLNKDKVDINGKPMVV

GSQNYYTLSWDLDQYRGIKADKAQIAKGFYFVDDYPEEAVLPDDTAIQLTTSNGKAVIGVTVKNYTSLSEVPKPLQAAFEKRKI

APKGAFQVFMAEDPQAFYDSYVTKGQNITIVTPMTVREEMLNSGKSYDNVAYQVDFGQVYETNTVTNHVPKVNPHKTNTNKEGV

SIDGKTVLPNTVNYYKIVLDYSQYKDLVVTEDTLAKGFYMVDDYPEEALTLNADGVQVMDKAGNLVKGISVKAYASLSEAPQVV

QEAMAKRQLTPKGAIQVLSADDPKVFYETYVKTGQTLVVTLPMTIKNELTKTGGKYENTAYQIDFGLAYVTETVVNNVPKLDPQ

KDVVIDLSQKENSLDGKEVALNQVFNYRLVGVLIPGNRATPLIEYRFDDDYDESHDDYNGVYTAYTVVDVTLKDGTVLLKGTEV

TKYTLQHVDTSKGTVTISFDKEFLEKLAEESEFQADVYLQMKRIASGEVENTVLHTVNGYTISSNTVKTTTPEPEPPTPNQPTP

PQPPIPTQEPPVPASVLPNTGESQSLLALVGGGLLLGLAYVLAKRKMEDN

>SspBC2 (X231_1187)
(SEQ ID NO: 2)

MHKARETKTYGSIRKSKIYGTCGVILGLAALSMISPVIADERTENKATNAPYAQTSPSSISTENQGKSEEKTGTLEVSISHSSL

DETIRKAQEAGLKVEFDSVVDKGTASTASELEKKQKEVESDYCTQADSIEKATEKYREDQRQNQTNRKKIQDENTAKKEQYQKD

LTSYQAEVNRINQKNASIRAENEKNQRENQAEIDRINQENAEIRKRNEAKRGAYESSLTDYTKKLATIKAERDAIQTSKPLFGS

ETGFKVYGGYNSAGRGSLDYYNDFTVVPDDNLPVESMRGFLGYHADTYVTGGAGTRVSKDSTETYDIIKSPTFGDTFYIHNIGT

LTDGRKIMAKVMVSDLGDYQGEVRNGVPVTDSDIYLKGGDGGSFYFVYNNHTRLEMVFDFYIEGTTTPVSLLIGTVITDVDWGQ

GSNLSYGSSGRGMVLNPSGSGLDFDGRVMKGVENGVNDTSDIPKASFASVGYGSSLTYLHTSSPGSTEGRTPAEWDAENLSGNA

QNVVFTILGEGAELKSIPPVNPPRKPTYEVETTPPNSPTGKPEEVLPPKPEEIKEKEIPSLVSPPTVRVRYARLQAMPDLEKFV

KNSSGESIDKSYVPKLSTVQWELTTKPLPANREAITDFEIVDALPSGFVLDVEASKKISSDFELTYDESSHVVRMKGLESLKSK

LNQDLSKEVQVPAPILVGKVTNDGATYKNNFQLKINNKYESYSNIVQISTPGKPNDPDNPNNNFIQPLKHNYNKDKVIIDGKSV

LVGSTNYYHITLDYDQYKGMKADSSTILKGFGAIDDYPEEAVTINQSDIRYIDSEGKEVAGISVYQYDSIDAVDNDKVKAFLAS

SEIKPKGAFQVFLVDDPEAYFNQYIKSGKSVTIIDPMVTKEELRNTGKSFENTAYQVDFGNGYQTDTVVNNVPTVKPTKKNLNK

AGVNIDGKQVLAGFVNYYKVTADYSQYKGIEADKDRIGKGFYIVDDYPEEAVTINQDGVQVTDSKGQVVKGLKMALYDSLDKAP

SGVQESLESSHFTPKGAIQVFEAENPEEFYKTYVQAGEVLTITNPMTVKKELGQTGGKYENTAYQLDFGSGYQTDKVENNVPTA

KPTKKNLNKAGVNIDGKQVLAGSVNYYKVTADYSQYRGIEADKDRIGKGFYIVDDYPEEAVTINQDGVQVTDSKGQVVKGLKMA

LYDSLDKAPSGVQKALKSSNFTPKGAIQVFEAENPEEFYKTYVQAGEILTITNPMTVKKELGQTGGKYENTAYQVDFGNGYQTD

TVVNNVPTVKPTKKNLNKAGVNIDGKQVLAGSVNYYKVTADYSQYRGIEADKDRIGKGFYIVDDYPEEAVTINQDGVQVTDSKG

QVVKGLKMALYDSLDKAPSGVQKALKSSNFTPKGAIQVFEAENPEEFYKTYVQAGEILTITNPMTVKKELGQTGGKYENTAYQI

DFGSAYITETVVNNVPTAKPTKKNLNKAGVNIDGKQVLAGSINYYKVTADYSQYKGIEADKDRIGKGFYIVDDYPEEAVTINQD

GVQVTDSKGQVVKGLKMALYDSLDKAPSGVQESLKSSHFTPKGAIQVFEAENPEEFYKTYVQAGEVLTITNPMTVKKELGQTGG

KYENTAYQVDFGMAYVTETAVNNVPKIEPKKDVVIDHLSKESLDGKEVKMNQTFNYKLVGSLVPKDRSEQLFEYKFSDDYDETH

DEYQGVYQVFATVDFETSDGQKFKAGDELTKFTSQVVDKAKGKVDISFDGAFLKSILETSEFQAEVYLQMTRIQSGAVENTYYH

TVNGVEVVSNTVVTQTPEEPKTPEEHPQQPERSLPSTGEQASAELLLAGLTMGSLATGLLYSKRKKKEA

>PspO (X231_1186)
(SEQ ID NO: 3)

MKLRTTILATTASVTLLGLGNSQPVYANSTTSSQVESLKSEFIKAKREYEQAKSIYDNALSSSPSNTIILSDKYIKALKTAFSD

FNISQTERDSAKSILQSESLRLKNQNSFHKDVADEGERLDVNNLPLAVRQELSFFAQDLINQVRSQVGTPRVSVSISALDFADK

VAKAYVQDNWGWHKMSVSGTLGHDATGINHVAREYGLPTTNSEEEKKGEQNYENLASRLPGFKTANKAQLKEAIYIGMIEFMFN

DTEWMHAQSIAGLNWGNVNSKDYFGLSFSSRSSVSSAHFITVSQEDIKRASKSSFSTAAVSDPTSVNRRQAIKKLEEDYKAKEK

-continued

IYQDFQKQADSKGSQGQSNQGSATVTEPSKPSAGSAEPTKSIENTSDLRDQWKQEGSYWYYFDRAGKALVNSWKGNYYLKSNGV

MARNEWVYDTNYKAWYYLKSDGSYAQNSWQGSYYLKSDGKMAQSEWLYDSSYKAWYYLKSDGSYAQNSWQGSYYLKSDGKMAQS

EWLYDSSYKAWYYLKSDGSYAQNSWQGSYYLKSDGKMAQSEWLYDSSYKAWYYLKSDGSYAQNSWQGSYYLKSDGKMAQSEWLY

DSSYKAWYYLKSDGSYLRDQWFKDGSAWYYLKADGKMAQNETIGAYYLDYSGKWIS

>ZmpC2 (X231_0594)
(SEQ ID NO: 4)
MKEFQFERKQRFSLRKYAIGACSVLLGTSLFFAGMDAQPVQATETSSTLISSHYLDEQDLSEKLKSELQWFEENKIEVKEGKEY

YFVYRKLATRLPETGLFSNDGTFILGAGLLLLSFTLIKRKRGASYFLVTVFAVGGWGASISAFENLVELQPALVKRVEGQFLPS

PERVQGYEFTGYYLVRDSGNKELSVDKVESPALSQKEDSSEPQSKKIVPQTASYFSSTEDLVQSPQPSYAVEKIVEAPDEMVPI

GTKEEVAGNPQVEQPKAKDNSDHKTSPEEGVLNVTVEKPELLITTEEVAFQTIEQEDATLAKGQTKVVQKGVVGERTIYTEVTV

VNGEKSSKVIENIITKEPVNKVIAVGTKEEVAPKPTQPVTPEPEEVKPVQPEKTPIVENETETKPVDGIGQPTPGAEETPGTEA

TSGEKQTPDKPEAEPKQPEREEDQSPVGQKVEENQLENSVEGAKDAGETAPQEPQKQPEQTAPSPEVNPSQGNEPAPAVQPDPL

APQEQSDSQVQPTVPSPVTKEKVLDYKTIYTASPALNYQEQQVEVAGENGKEVITTSYSFDESTGKIVENTSTKIEKQPVDRIV

KVGNVEETRSTVKRREQFVADESLDKGVKEVRNQGQDEETTTIRVYKVNEQTGSISEETTIENTPAKDKVIKVGNVEKLVSPIE

ITELKKEDSTLPKGKEKVEDAGEQGETTVTKTYEVNPETGELTNPVEKTETTKAMRQKVILVGTKEEKPHLLPVNSELENAVNV

TEATAEMRNVDLLTNEKLKAQLAPSDIEINRDLFLKRKELQKTNPQIRDDEVREILRKEYLEKLSIKETLDATKTDLEVSLKKV

AAHTLSILGDNQQNREKVKGDIEANKEKILLGLSYINRFYNIDFGDANIRDILAYNPSSFGKKDLTSLDWLTHLGSMSYDELRL

TNSPKTFEKYFSKITNKTTLLDFLDYNRMTFTNMDGDTWLKKATKAIVVEKASKEKTDEKVELYTKLTTDPEKYGAEGLQINNR

KQQNIATLLGLVNIKEPSVYAITNIATVTYGNIGTYMDTSLEKTNKAKYTGELNKVKELIELTATRQAAYVDTLYRITKEENRS

KLVTNRVIVDTMKKYTTDTSAGIGTTWSKESGPTADKGVKDFMTPLGLYSPSQNVGAEANGVGVRYFIDRVLDDRGSATYSHEM

THLLDRTVLFNNHGRRDGTGAEFYARGIFENSYNPEKDTYFNLNFVCDESDKNGFYNRTPDRFKTAEDLKSYMKGSFDVLYTLD

YLEAEASRGLSTEDKMSYFKKIAPITSSGPRTWVDYRNTAVKPTHKSEEIQSLTLEDAKKLTDIDSLIDNHILVNRYIIAGFSD

KGKITANGYYTVDMFDTIYGVSQNDSGMSGDITFRKQAFELMAALGYYEGFVPYVSNQYKQAAEAENKPLSDTYIFNKILNGKS

YAEFKKAQFKERVAKIDQLKPLTIQYEGQQISLTSQKLKELMQKAVQEELKQIKAGKTTARTYTFIETPVQKLKKAIYKAYLKD

SDDFRQSIYNS

>NanO1 (X231_0534)
(SEQ ID NO: 5)
MIGLAAPDLPVIGGGVVAADVIQGGNDIKDVNVHSKSAEGVAMTYTTYDSGTSGKQTASGSGVFVAPNVMVTVAHNYYDKNQED

KSAVLRGGASARSYVVMNSETEKHNKVPTSGVSETLEKDSIHLYDEKNFGKDYINDLAVVVTKKTVEAMTGGEDSPRELSHKEV

STGDKISMVGYPNDFSTPNLSAENKARLKDGKAYSVTTTVSSVNKESGTVTYHSSALGGFSGAPLFNDKGEVVGIHQHGTNTPN

AQESERIGGGTLFTEKHRAWIRSMIDKYGIKGWYIDGANRYYYDENHRALKDVESEIDGALYRFDEKGRATLLEGEEKGRVLLR

VEDTKGTPLISDKVVQEGSVGSGLNFHLRQNPNFKQLIATSPTAKVVSYNGVPINKLASDTSWSDEYVSKLALGDTIIRAVVDS

VTPPSTSSSDFARTEVGKVDLSGKSNLPVPSKEVLQAPNGSENFYATTHIQTPDGSGSGTLIAPNLVLTVAHNFLTVKGSEVVT

KSGRTNTVYKATLPSGQPVNFSDDDIVYWNKKDSVFGFKNDLALVRLKEKLTAVSPVEVVSESTSITKGDKVSVYGFPDGRLSP

VLDSEVVATTDFGSGIEGISYGGTKPGASGGGLYNDKGSLIGVHQNGVVGSRSGGLVLSKEQLDWVRSYIEGKPKAPVYVTDNI

LVDEKDKDKLPSTSKEEKPTTPKVESDKDKPNTPLKPQEKPKTEVITSYEGDSTLEVGKERTEETEGEKEGVSLIYRTVYKGTK

SKTEMSPIAFDTVYQGDETKELGFRSVLEGKEGLVTRTTSYQVDKYTGAVSSKISEEKIAPQSQVITLGIKKNSSTKEVPITER

FEDSAELEKGKTEVISEGSVGKEVTTVTYKVLPDGKVIENSRTVDVTPMREVVRKGVKEVVSPDKVESLVPKDAPIREEQPAL

SEGFSESDALVSGEKIQGDLGILIVSSEELVPERVEVPDFVTKVTGGEKLTVEGHRNESKIKTPSKQERSSRPETTAQFTTNGT

GSSSLTAVFGGKTDKILLSTVEHSVIKHNQQRGWHKINNQWYFRNSDGKERTGWMKENDAWYYFDTNGTMQTGWLEDTDGNWYY

LNDNGRMEIGWFQDSSGAWYYLGSSGRMESNTWIYYKGKWYYIDALGKLLFNSVTPDGYRVNEYGEWIN

-continued

>NanO2 (X231_0533)
(SEQ ID NO: 6)
MEKVKGLQNATVHVEFKPAADGPSFYNLFSASSTTKVNEYFTMAINNGTALIEGRGADGSQFYGSYTDAPLKIRPGKYNSVTFT

VERPRKDSPNGQVRLYVNGVLSRTNKKSGKFLADMPDVDKLQLGATNRAGELKWGSDLSIRNLTVYNRALTPEEVKKRSQLFDV

IDIEPLLAEGAVLTEKQELFMSGVNGKPNSEGIKSYRIPPLLRTDKGTLLAGADQRRLHHSDWGDIAMVVRRSEDGGTTWQPTL

TLTNLRDNPEAKDPQASSSLNIDMVLVQDPTTKRIFSIYDMFPEGRAVFGMPNKPQKAYQQVGDKHYQLLYKQGENQAYTVREN

GEVYDANNQKTDYRVVVDPKEEAYRDKGDLYKREELLGNIYFAQSAKTPFRVAYTSYLWLSYSDDDGKTWSQPRDITPSIRQDW

MKFLGTGPGTGIVLRTGEHKGRILVPTYTTNAISHLSGSQSSRLIYSDDHGETWQAGAAVNDDRTVGRRKIHSSTMNNRNTQNT

ESVAVQLNNGDVKLFMRGLTGDLQVATSKDDGQTWDKEIKRYNQVKDVYVQMAAIHTMHEGKEYIILTNSGGLKRTNGMAHLAR

VEDNGDLTWLHHRPIQKGEFAYNSLQELGNGEYGILYEHTEKGQNDYTLSFRKFNWDFLTKDPVYPTSVTIRDVRKLETEEEDA

EQGILAMQFDSEVLVNAIPTLTLANGHKATFLTQADQKTLLFTFNKEDAGQEITGLMAGRIDSMHDLPVTLAGSRIPEDAKENP

VETMNTVRENVSEEMTERKSEKDKLSLESSDRMVANSHLTSFAPRYLQSYVGDVIKTETKVPITTGWKQENGAWYFYTSAGEVV

KGWHQEADKWYYLSSTGAMATGWVRDGNQWYYLSESGAMSTGWVESSGVWYYLHSNGSMATGWIKDGDHWYYQESSGAMRVNQW

FQVGDKWYYVNESGRLAVNTIVDGYQVNSNGEWVNY

>CbpI1 (BM49_0273)
(SEQ ID NO: 7)
MKQFLERASILALSLVLITSFSISSALPAMFDYYQGYSKEQIELLVSLPSFGIMMMLLLNGFLEKIFFERLQISLGLLILSLSG

TAPFWYQAYPFVFGTRLLFGLGLGMINAKAISIISERYQGKRRIQMLGLRASAEVVGASLITLAVGQLLAFGWTAIFLAYSAGF

LVLPLYLLFVPYGKSKKEVKKRAKEASRLTREMKGLIFTLAIEAAVVVCTNTAITIRIPSLMVERGLGDAQLSSFVLSIMQLIG

IVAGVSFSFLISIFKEKLLLWSGITFGLGQIVIALSSSLWVVVAGSVLAGFAYSVVLTTVFQLVSERIPAKLLNQATSFAVLGC

SFGAFTTPFVLGAIGLLTHNGMLVFSILGGWLIVISIFVMYLLQKRA

>CbpI2 (X231_0220)
(SEQ ID NO: 8)
MKKIVFASALALTLAGAVLTNDVFANDRLVATQSTDGNVLTSEVLKPSSGNVLVGIKGEFLPPHQQSILDAINKIRKEAADEGL

VDKYVPVKWSVDHEKTAFVRAAEVSVTLKAERLSSKNNWTAFFSGNSLSGEVLDLNPDGFLKAIENWHAEKANYVAKKKDKTSK

EFSFYYENLINPKFTYVGLAAFKNAASPQKAATVALALGTTTSSEELAGGYGSAVQYTEVTASNLSTVKSKAMVVETPLKDFRK

STSDQSGWVQSNGKWYFYESGDVKTGWLKTGGKWYYLNDLGVMQTGFVEVDGSVYYLSNSGAMFTGWGTDGSRWFYCDGSVAMK

TGWYKENGTWYYLDEEGIMKTGWFKVGQHWYYANGSGALAVSTTTPDGYRVNANGEWVS

>CbpAC1 (X231_0613, representative of ST448, ST1186)
(SEQ ID NO: 9)
MSKSNHERRMRYSIRKFSVGVASVLVASFFMGSVAHASGLVKDDSVKTTEIAATNREKENDAKSGWGGIIDGSGKLLGGFSEIK EKLEKEIDESSLTSEQKKSYKEKIVKVKQNDVDGLFGVHREYLNQLDFQYLELSKVEEEFKYQEEQIQRMFEQKGITNEDKDAM LKKIAEIHQEAEKDIKASGGYRDKLNGTKVKFLQNLDKLFTSTKSKFEKEMQELYRKKEAEIVKEKHLEKDKIYDDADVQKLRE LEKDALKKLDEAKTNDEALRVKLEFARNVEKNSQQVQKIDDKLQELIKEAKRELEKLNQGIAEVDKLPELPANDSDYMVQKKYI WDEDKETIPKKIAKFKENLGNKTYTKESLQKFIDDCIYYQTHAKIEVMTRKVAGYRKAYPNNPEIEKEFVSHIKQTSSLTYASL ENDSLKRYFEKDFAPAFERIKQIVEGLEKPHTPAQPGIENQKPSAPKTEKSAEQPKAGWKQENGMWYFYNTDGSMATGWLQNNG SWYYLNANGAMATGWLQNNGSWYYLNANGSMATGWLQNNGSWYYLNANGSMATDWVKDGNTWYYLEASGAMKASQWFKVSDKWY

YVNGLGALVVNTTVDGYRVNANGEWVS

>CbpAC2 (BM51_0858 representative of ST1270, ST344, ST2315)
(SEQ ID NO: 10)
MSKSNHERRMRYSIRKFSVGVASVAVASLFMGSVVHATENVSANPPIPQIVSPGDKKEYEDAVQRVNKEISDYVTSRLDSLDRS VSGFSEIVTKVQVVVDKYRDKIDRVSTKSMVEELGREVKKKVDEEIKLFQNRSGSKSTPKGLSLNDGLQGGGDPSVGQGPGVVP QPGGQAGGSMVVPPVTQTPPSTSPSPGQKATEAEKKKLQDLIRQGQEELKKLEDYLREVNNYPELPDNDPDYKVQKKDIWDNSK DTAPKKIQVFKEQLEKQTYTEKTLKDAVAEFIYYQFHAQIETMTRKIATYRKKHPNVAEVERLFSEKLKQTANSTYATLEGEAL KTYFERDFLPVFNKIHSIIEELEKKSSQGELKKQDKVAEAQKKVEEAEKKAKAQKEEDRRNYPTNTSKTIELEIAEAQVEVAKA ELELAQAQAQTPQDTDKINTAKAKVETAKSKVKTLEKIKSDSGRAQAGDQKPSMPAPDTKPDLQPQPEVPSTSPEPKPIPQPDG -continued KQPSTPKEPENKKPSVPTQEKPIPQPEKPKPEVKPQPETPKTSKIITASDGKTKVTVVFDKAVDADKVNIKEVTTKELAEKIAR QTGGGTVRIFDLSLSKGGKETHVNGERTVRLALGQTASDVHVYHVKENGDLERIPSKVENGQVVFKTNHFSLFAIKTLSKNQNV TTPKQIKPSVQHGQTQIGENQTGKFQNKEVNHKPLATGNETMAKENPTSATEKNLPSTGAATNLVLEIIGLLGLAGTSLIAMKR

RK

>SspBC1 (X231_1085)

(SEQ ID NO: 11)

TTGTTGCTACTTATCAAAAGAAAAGAAGGACTTTTTATGACCAAACAATGTCATCATCACTTTTTAGTCAATCAGGAACAAGCA

GAAAAGCATGTCTTCCGTAAAAGTAAGAAGTATCGTACGCTGTGTTCGGTAGCACTTGGAACTATGGTGACAGCTGTTGTCGCT

TGGGGTGGCCAAGTAGCACAAGCTGACGAAGTGACAATGCCACCACTAGATAAGACTGTTCAGTTAACGGAAAATAATGCGACC

AATTTACCAGAAGCTCAGCCAGCACCAGTTGCTGAACAGACTGATAGCCTTTTCTCAACTGGCCAATCAGATGGGACTATCACA

GTAACGGTTCCTCATGATACGGTAACCAATGCCATCAATCAAGCAACCGCTGAAGGGCTTACTACCATTCAGGATAAACCTATG

GATTTAGGCAACACGACTTCTGCTAGTGAGACCAGTAAGCAATTGGATACCGCTGAAGCGGATGCTGCCAAACAAGCTGAGGAC

ATCACTCGGGTGACAAATACCTATAAAGCTGACAAAGTCGCTTATGAACAAGATAAAACTCGTGTCGAAAAAGGAAATGCTGCG

TTGGTTGCTAGTCATAAAGAAGCTACTCAAGCAGGAAAGGCCTTGAATAGTTCAGTAGATACCACGGCTTCAGAAGTGAAGACT

CAGGACAAGTCTGCGAACGTGACTATTACAACTCAAACCGTTCCGTCAGGAGAGGGATCAACTGTTTCAGGTTATCAGGACTAC

ACATCTGCGGTAGCTGCTATTGATAAACAAAACAAGGCTAGTCTTGCGGACTATATCACGAAAAAACAAGCCGCAGATGCCATT

ACCGCAAAGAACCTAGCTGTTCAAAAGGAAATGAAGCAGGTCTTGCGAATGCAAAGGCAGAGAATGAAGCGATTACTAAACGC

AATCAAGCAGGACAAAAAGCGATTGATGATGAAAATAAAGCAGGTCAAGCTGCTGTGGATACCTACAATAAGAACCAACAAAA

TTGGTGACAGACCGTGAAGATGAGATTGCTGCTATTATAAAACGCAATAAGGAGAAAGAAGAAGCTGCTAAGAAAGAAAATGAA

GCCATTGATGCCTACAATGCCAAAGAAATGAACCGATACAAACGTGACTTAGCTGACATCTCAAAAGGAGAGGAAGGTTACATC

TCACAAGCTCTTGCTCAGGCTCTCAACTTGAACAATGGGGAACCGCAAGCCCGACATTCAGCTGACACGAGAAATCCTAATCGC

ATCATTGCTAAGGGTGACGCCATGCTTGGTGGGTATTCTAAAATCCTAGATTCTACTGGTTTCTTCGTCTATGATACCTTTAAA

ACTGGAGAAACCCTTTCATTCACTTATCAAAACCTTCAAAATGCGAGTTTTGATGGTAAAAAGATTACCAAAGTTGCTTATGAC

ATCACAAACCTAGTGTCTCCAACTGGGACGGATTCTGTACAATTAGTTGTGCCTAATGACCCAACAGAAGGCTTTATTGCCTAT

CGTAATGATGGGACAGGGAATTGGCGAACCGATAAAATGGAGTTTCGTGTCAAAGCCAAGTATTTCTTAGAGGATGGCTCGCAA

GTCAGCTTTACCAAGGAAAAACCAGGTGTCTTTACCCATTCCTCACTTAATCATAATGACATTGGCTTAGAGTATGTCAAAGAC

ACATCAGGCAAGTTTGTCCCTATCAATGGCTCAACCATTCAAGTGACAGATGAAGACCTAGCACGTTCACTTTCTTCAAACCGT

GCTAGTGATTTGAACCTCCCAGAAGAATGGGATACCTCTTTTAGCAAGTATGCTTACAAGGGAGCGATTGTCTCAACCGTCACA

TCAGGCAATACCTACACCGTGACTTTTGGACAAGGCGATATGCCCCAAAATGCAGGACTGACCTATTGGTTTGCCTTAAACACC

TTACCTGTTGCACGAACCGTCAAACCTTATAGTCCGAAACCACATGTGACCCCAAAACTAGACCCAGTCCCAGAGCCGATTAAA

GTCGTGCCAAAAACCTTTACCCCAAAGACCTTTACCCCAGAGCCACCTGTGATCTTTAAGGAAAAACCACTGGAGAAAGTGACT

CAACCTCGCTTGACTTTGACAAAGGTGACCTTTGCTAAAGAACCTAGGTCTGAACCTTTGCCTAAAGCACCACAAGTACCAACG

GTTCATTATCACGACTATCGTCTGACAACGACCCCTGAAATCATGAAAAAAGTGGTCAATACCGACCAAGACAATCTTCATGAC

AAAACTATTGCCAAGGATTCGACAGTTATTTATCCTTTAACAGTTGACGTTTTTTCTTCAAATCGTGCCAAAACAACTACCCTT

ACGTTTGAAGATTACCTTCCAGCAGGCTATGCCTTTGATAAAGAAAAAACACAAGCAGAAATGAGAATTATACGCTTACCTTT

GATGAAGCTAAGAACTTTGTGACCCTGACTGCCAAAGAAGCCTTGCTTCAAGAGGTCAATCAAGACCTCACTAAGTCTTATCAA

CTGGTGGCTCCTAAACTTTATGGTAGCCTTCAAAATGATGGGGCTACCTATTCCAATAGTTATAAGCTCCTCATCAATAAGGGA

ACGTCAAATGCCTATACAGTGACCTCTAACGTGGTGACCGTTCGTACACCTGGTGATGGGAAAATCACTAGCCGTATTACTCCT

CAAAAACGCAATGAGAATGAAGACGGTGTGGTCATTAACGATACGGTGGTGGCTTTAGGAACGACTAACCATTACCGTTTGACG

TGGGATTTAGATCAATATAAAGGTGATACCTCTTCTAAAGAAACGATTGCTCGTGGTTTCTTCTTTGTGGATGATTACCCAGAA

GAAGTCTTGGATTTGGTGGATAAAGGAACAAGTATCACCACTCTTGATGGTAAAGCTGTATCAGGGATTACTGTTAAGGCCTAT

GTGTCGCTGTCAGAAGCTCCTAAAGACCTTCAAGATAAACTCGCTCATGCCAAGATTTCTCCTAAAGGAGCTTTCCAAATCTTC

```
CAGCCTAACGACAATCAGGCTTTCTATGACCAGTACGTTAAAACAGGAACCTCTTTGAACCTTCTCACCAAAATGACCGTCAAA

GACAGCCTTTATGGTCAAACTAAGACTTATCGAAACAAAGCCTACCAAGTTGATTTTGGGAATGGCTATAAAACAAATGAGGTG

ACCAATACCCTTGTCAGCCCCACACCTAAGAAACAAAACCTTAATAAGGATAAAGTGGACATCAATGGAAAACCGATGGTAGTG

GGTTCACAAAACTACTATACCTTGTCATGGGATTTAGACCAATACCGTGGCATTAAAGCTGATAAAGCTCAAATCGCAAAAGGC

TTCTACTTTGTGGATGACTATCCTGAAGAAGCTGTGCTACCAGATGACACAGCTATTCAACTAACGACATCTAACGGCAAGGCT

GTCATAGGTGTTACGGTAAAAAACTACACGAGTTTATCAGAAGTCCCTAAACCCCTACAAGCAGCCTTTGAGAAACGCAAGATT

GCGCCTAAAGGAGCTTTCCAAGTCTTTATGGCAGAAGATCCACAAGCCTTTTATGATTCTTATGTGACCAAAGGCCAAAACATT

ACCATCGTTACACCGATGACAGTTCGTGAGGAGATGCTTAATTCAGGGAAGTCTTATGATAACGTGGCTTACCAAGTAGACTTT

GGGCAAGTCTATGAAACCAATACGGTGACCAATCACGTGCCAAAGGTAAATCCTCATAAGACCAATACCAATAAAGAGGGAGTG

TCTATTGATGGCAAAACCGTTCTTCCTAATACCGTAAATTACTATAAGATTGTTCTGGATTATAGTCAGTACAAGGACTTGGTA

GTGACGGAGGATACCCTTGCCAAAGGTTTTTACATGGTAGATGACTATCCAGAAGAAGCTCTAACACTAAATGCAGACGGTGTT

CAAGTGATGGATAAGGCGGGAAATCTTGTCAAAGGGATTTCTGTCAAAGCCTATGCTTCGTTATCAGAAGCGCCTCAAGTGGTA

CAAGAAGCTATGGCCAAACGCCAACTTACACCAAAAGGAGCCATTCAAGTTTTAAGTGCTGATGATCCAAAAGTTTTTTACGAG

ACCTATGTTAAGACAGGTCAAACCTTGGTGGTGACGCTTCCGATGACCATTAAGAATGAGTTGACAAAGACTGGTGGCAAGTAT

GAAAACACGGCTTATCAGATTGACTTTGGTTTGGCTTATGTGACAGAAACAGTGGTCAATAATGTGCCAAAACTAGACCCACAA

AAAGATGTGGTGATTGATTTGTCACAAAAGGAGAACAGTCTTGATGGAAAAGAGGTTGCCTTGAATCAGGTCTTTAACTACCGC

TTGGTGGGAGTACTTATTCCTGGTAATCGTGCGACACCACTCATCGAATACCGCTTTGACGATGATTACGATGAAAGCCATGAC

GACTATAATGGTGTTTACACGGCTTATACTGTGGTAGATGTCACTCTAAAAGATGGGACGGTTTTACTAAAAGGGACAGAAGTG

ACTAAGTACACGCTACAACATGTCGACACGTCAAAAGGAACGGTTACCATCAGTTTTGACAAGGAATTCCTAGAAAAACTAGCA

GAAGAATCCGAGTTTCAGGCAGATGTTTACTTGCAGATGAAACGAATCGCTTCAGGTGAAGTAGAAAATACGGTACTACATACC

GTCAATGGCTACACCATCAGTTCAAACACGGTTAAAACAACTACTCCTGAACCAGAGCCACCAACTCCGAATCAACCAACACCA

CCCCAACCACCTATTCCAACACAAGAACCACCAGTTCCAGCAAGTGTCTTACCAAATACAGGAGAGAGTCAATCTCTTTTGGCG

CTTGTCGGTGGAGGCCTTCTTTTAGGCTTAGCCTATGTCCTTGCTAAACGCAAAATGGAGGACAATTAA

>SspBC2 (X231_1187)
                                                                 (SEQ ID NO: 12)
ATGCACAAAGCAAGAAACAAAAACATATGGATCTATTCGGAAATCAAAAATTTATGGAACTTGTGGAGTGATACTAGGTTTA

GCAGCTTTAAGCATGATAAGCCCAGTTATAGCAGATGAACGAACTGAAAATAAGGCTACAAATGCGCCTTATGCCCAGACGAGT

CCAAGCAGTATTTCTACTGAAAATCAAGGAAAGAGTGAAGAAAAAACAGGAACGTTAGAAGTTTCTATTTCCCATTCCAGTTTA

GATGAAACTATTCGAAAGGCACAAGAAGCTGGATTGAAGGTGGAATTTGATTCTGTAGTAGATAAAGGAACTGCAAGTACAGCC

TCTGAGTTGGAAAAAAAGCAAAAGGAAGTCGAGAGTGATTATTGCACACAAGCAGATAGTATTGAGAAAGCTACTGAAAAATAT

CGTGAAGATCAAAGACAAAATCAAACGAACCGAAAGAAAATCCAAGATGAAAATACTGCGAAGAAGGAACAATATCAAAAGGAT

TTAACTTCTTATCAAGCTGAAGTGAATCGAATTAATCAGAAGAATGCTAGTATTCGTGCAGAGAATGAAAAAAATCAACGAGAG

AATCAGGCAGAAATAGATCGTATCAATCAAGAGAATGCAGAAATCCGAAAACGAAATGAAGCTAAGAGAGGAGCTTATGAAAGC

TCTTTGACAGACTATACAAAGAAGCTAGCAACTATTAAAGCTGAGCGAGATGCAATTCAAACAAGTAAGCCTTTATTTGGATCT

GAAACAGGTTTCAAAGTTTATGGAGGATATAATTCAGCTGGTCGGGGAAGCTTAGACTATTATAATGATTTTACAGTAGTACCA

GATGATAATCTACCAGTAGAGAGTATGCGTGGTTTTTAGGTTATCATGCAGATACTTATGTAACAGGAGGCGCAGGAACTCGA

GTTAGTAAGGATAGTACGGAAACTTATGATATCATTAAATCTCCAACATTTGGAGATACATTTTATATTCATAACATTGGAACG

TTGACAGATGGTAGAAAGATCATGGCAAAGTCATGGTTTCGGATTTAGGAGACTATCAGGGAGAAGTTCGAAATGGTGTTCCT

GTGACAGATTCAGATATCTACCTCAAGGGTGGAGATGGTGGAAGTTTCTACTTTGTCTATAATAATCATACCCGTTTGGAAATG

GTTTTTGATTTTATATTGAAGGTACGACAACTCCTGTTTCCCTCTTAATTGGAACAGTTATTACCGATGTAGATTGGGGTCAA

GGTTCAAATTTGAGTTATGGCTCATCTGGTCGTGGAATGGTTCTTAATCCAAGTGGTTCAGGTTTGGATTTTGATGGTCGCGTT

ATGAAGGGAGTAGAAAATGGAGTTAATGATACCTCAGATATTCCTAAGGCTTCCTTTGCTTCAGTAGGGTATGGTTCTAGTTTA
```

-continued

```
ACGTACCTTCACACATCATCTCCTGGTTCGACAGAGGGAAGAACTCCCGCTGAATGGGATGCAGAGAATTTGAGTGGAAATGCT
CAAAACGTTGTCTTCACAATTCTTGGGGAGGGGGCGGAGTTGAAAAGCATTCCACCAGTAAATCCACCTCGCAAACCAACTTAT
GAAGTTGAAACTACTCCACCCAATTCTCCAACTGGAAAACCTGAAGAGGTACTCCCACCCAAACCTGAGGAGATAAAGGAAAAA
GAGATCCCCTCTTTAGTATCCCCTCCAACAGTAAGGGTTAGATATGCACGCTTACAGGCAATGCCTGACCTAGAAAAGTTTGTA
AAAAATTCTTCTGGTGAATCTATTGATAAAAGCTATGTACCTAAACTTTCAACAGTACAGTGGGAACTAACAACTAAGCCTCTT
CCAGCTAATCGTGAAGCTATTACAGACTTTGAAATTGTGGATGCCTTGCCTTCAGGTTTTGTGTTAGATGTTGAAGCTTCCAAA
AAAATTAGCTCAGATTTTGAATTAACTTATGACGAGTCGAGCCATGTTGTTCGGATGAAAGGCTTAGAAAGTTTAAAATCTAAG
CTTAATCAAGATTTAAGTAAGGAAGTACAAGTACCAGCTCCAATTTTAGTTGGTAAAGTAACGAATGATGGAGCGACCTACAAG
AATAACTTCCAATTAAAGATTAACAATAAGTACGAAAGTTATTCAAACATTGTTCAGATTTCAACACCTGGTAAACCGAATGAT
CCGGACAATCCGAATAATAATTTCATTCAACCTCTTAAACATAATTACAATAAGGATAAAGTTATCATTGATGGTAAATCAGTT
CTAGTTGGTTCGACAAATTACTACCATATTACCTTGGATTATGATCAATATAAGGGGATGAAGGCAGATTCATCTACTATTTTA
AAAGGATTCGGAGCAATTGATGATTACCCAGAAGAGGCTGTTACGATTAATCAATCGGACATTCGTTATATTGACAGCGAAGGA
AAAGAAGTTGCTGGTATCTCGGTGTATCAGTATGATTCTATAGATGCCGTTGATAATGATAAGGTTAAAGCTTTTCTTGCTAGT
TCTGAAATTAAGCCCAAGGGTGCTTTCCAAGTATTTTTAGTGGATGATCCAGAAGCTTATTTTAACCAGTATATTAAATCAGGA
AAATCGGTTACAATTATTGATCCAATGGTAACTAAGGAAGAACTGCGAAATACAGGAAAATCATTTGAGAATACGGCTTACCAA
GTTGATTTTGGTAACGGATATCAAACTGATACAGTTGTCAATAATGTTCCTACTGTTAAACCAACCAAAAAGAATTTGAACAAA
GCAGGTGTGAACATCGATGGGAAACAGGTCTTGGCAGGCTTTGTCAACTACTACAAGGTAACGGCAGATTATAGTCAATACAAG
GGCATTGAAGCGGATAAAGACCGTATTGGCAAAGGGTTCTATATCGTTGATGATTATCCAGAAGAAGCTGTTACCATCAATCAA
GACGGTGTTCAAGTGACGGATTCTAAAGGGCAAGTGGTCAAAGGTTTGAAAATGGCTCTTTATGATAGTCTGGATAAGGCACCA
TCAGGTGTACAAGAATCCTTGGAGTCTAGCCATTTCACTCCGAAAGGAGCGATTCAAGTATTCGAGGCAGAGAATCCAGAGGAG
TTCTACAAGACTTATGTGCAAGCTGGAGAAGTTCTGACCATTACCAATCCAATGACTGTTAAGAAGGAATTGGGTCAAACAGGT
GGTAAGTATGAGAATACAGCTTATCAATTAGACTTTGGTAGTGGCTACCAGACGGATAAGGTAGAGAACAATGTTCCTACTGCG
AAACCTACCAAGAAAAATCTGAATAAAGCAGGCGTGAACATCGATGGGAAACAAGTCTTGGCAGGCTCTGTCAACTACTACAAG
GTAACGGCAGATTATAGCCAATACAGGGGCATTGAAGCGGATAAAGACCGTATTGGCAAAGGGTTCTATATCGTTGACGATTAC
CCAGAAGAAGCTGTTACCATCAATCAAGATGGTGTTCAAGTAACGGATTCTAAAGGTCAAGTAGTTAAAGGTTTGAAAATGGCT
CTTTATGATAGTCTGGATAAGGCACCATCAGGTGTCCAAAAAGCCCTGAAGTCTAGTAATTTCACTCCGAAAGGAGCGATTCAA
GTATTCGAGGCAGAGAATCCAGAGGAGTTCTACAAGACCTACGTGCAAGCTGGAGAAATTCTGACCATTACCAACCCAATGACT
GTTAAGAAGGAATTGGGTCAAACAGGTGGTAAGTATGAGAATACAGCTTACCAAGTTGATTTCGGTAACGGTTATCAAACTGAT
ACAGTTGTAAATAACGTTCCTACTGTTAAACCAACCAAGAAGAATTTGAACAAGGCAGGCGTGAACATCGATGGGAAACAAGTC
TTGGCAGGCTCTGTCAACTACTACAAGGTAACGGCAGATTATAGCCAATACAGGGGCATTGAAGCGGATAAAGACCGTATTGGC
AAAGGGTTCTATATCGTTGATGATTACCCAGAAGAAGCTGTTACCATCAATCAAGATGGTGTTCAAGTGACGGATTCTAAAGGG
CAAGTGGTCAAAGGTTTGAAAATGGCTCTTTATGATAGTCTGGATAAGGCACCATCAGGTGTCCAAAAAGCCCTGAAGTCTAGT
AATTTCACTCCGAAAGGAGCGATTCAAGTATTCGAGGCAGAGAATCCAGAGGAGTTCTACAAGACTTATGTGCAAGCTGGAGAA
ATTCTGACCATTACCAACCCAATGACTGTTAAGAAGGAATTGGGTCAAACAGGTGGTAAGTATGAGAATACAGCTTACCAAATT
GATTTTGGTTCAGCTTATATCACGGAAACAGTCGTAAACAATGTTCCTACTGCGAAACCAACTAAGAAGAATCTGAACAAAGCA
GGTGTGAACATCGATGGGAAACAAGTCTTGGCAGGCTCTATCAACTACTACAAGGTAACGGCAGATTATAGTCAATACAAGGGC
ATTGAAGCGGATAAAGACCGTATTGGCAAAGGGTTCTATATCGTTGATGATTACCCAGAAGAAGCTGTTACCATCAATCAAGAT
GGTGTTCAAGTGACGGATTCTAAAGGGCAAGTGGTCAAAGGTTTGAAAATGGCTCTTTATGATAGTCTGGATAAGGCACCATCA
GGTGTACAAGAATCCTTGAAGTCTAGCCATTTCACTCCGAAAGGAGCGATTCAAGTATTCGAGGCAGAGAATCCAGAGGAGTTC
TACAAGACTTATGTGCAAGCTGGAGAAGTTCTGACCATTACCAACCCAATGACTGTTAAGAAGGAATTGGGTCAAACAGGTGGT
AAGTATGAGAATACAGCTTATCAAGTTGATTTTGGGATGGCCTATGTAACTGAAACAGCAGTCAATAATGTTCCAAAGATTGAA
```

```
CCGAAGAAAGATGTAGTGATCGACCATCTAAGTAAAGAAAGTTTGGATGGAAAAGAGGTCAAGATGAATCAAACATTTAATTAC

AAATTAGTTGGTTCCTTAGTGCCAAAAGATCGCTCAGAACAGTTGTTTGAGTATAAATTTAGCGATGATTACGATGAAACACAT

GATGAGTATCAAGGTGTATATCAAGTGTTTGCGACTGTAGATTTTGAAACAAGTGATGGTCAAAAATTCAAAGCTGGTGATGAA

TTAACTAAGTTCACAAGTCAAGTAGTAGACAAGGCTAAAGGTAAAGTAGATATTAGCTTTGATGGTGCTTTCTTAAAGTCGATT

TTAGAAACATCAGAGTTTCAAGCAGAAGTATATCTACAAATGACACGCATTCAGTCAGGAGCAGTAGAAAACACTTACTATCAT

ACAGTTAACGGTGTGGAAGTTGTTTCCAATACGGTTGTGACTCAGACTCCAGAAGAGCCAAAAACTCCTGAAGAACATCCGCAA

CAACCAGAACGAAGCCTGCCATCTACAGGTGAGCAGGCTTCTGCAGAATTGCTGTTAGCTGGTCTGACAATGGGAAGCCTTGCT

ACAGGATTGCTCTACAGCAAGCGCAAGAAAAAGAGGCTTAG

>PspO (X231_1186)                                                          (SEQ ID NO: 13)
ATGAAATTGAGAACAACCATCTTGGCAACAACTGCTAGCGTAACGTTGCTTGGGTTAGGAAATAGTCAACCTGTGTATGCAAAT

AGTACAACGAGTAGTCAAGTAGAGAGCTTAAAAAGTGAATTTATTAAAGCAAAGAGAGAATATGAACAAGCTAAAAGTATCTAT

GACAATGCTTTATCATCTTCACCTAGCAATACGATTATACTGAGTGATAAGTATATAAAGGCTTTGAAGACGGCTTTTTCTGAT

TTTAATATTAGCCAGACTGAACGTGACAGTGCGAAATCTATTTTGCAGTCAGAAAGTTTGAGATTAAAGAATCAAAATAGTTTC

CACAAAGATGTTGCTGATGAGGGAGAACGTCTGGATGTCAACAATCTACCGCTAGCTGTTCGTCAGGAGTTGTCATTTTTTGCC

CAAGATTTAATTAACCAAGTTCGTTCTCAGGTTGGGACACCTAGAGTCAGTGTTTCAATTTCGGCACTTGACTTTGCAGATAAG

GTGGCGAAAGCATATGTTCAAGATAACTGGGGTTGGCATAAAATGAGCGTATCTGGTACACTTGGTCATGATGCGACTGGAATC

AATCATGTGGCGAGAGAATATGGACTGCCTACAACCAATTCTGAAGAAGAGAAAAAAGGGGAGCAAAACTATGAAATCTAGCT

TCTCGTCTACCTGGTTTCAAAACAGCTAACAAGGCTCAGTTAAAAGAGGCTATCTATATTGGGATGATAGAGTTTATGTTCAAT

GATACTGAGTGGATGCATGCTCAGAGTATTGCTGGCTTGAACTGGGGAAATGTGAACTCAAAAGATTATTTTGGGCTTTCATTC

TCTAGTCGTTCTTCTGTTAGTTCAGCCCATTTTATCACGGTTTCCCAAGAAGATATCAAGCGTGCAAGCAAATCAAGCTTTAGC

ACGGCTGCTGTGAGTGATCCAACTAGTGTCAATCGCCGTCAAGCAATCAAAAAGCTAGAGGAAGACTACAAAGCCAAGGAAAAA

ATTTATCAAGATTTTCAAAAACAAGCAGATAGTAAAGGATCTCAAGGGCAGTCTAACCAAGGTTCAGCTACTGTGACAGAACCA

AGTAAACCAAGCGCTGGCTCAGCTGAGCCTACTAAATCGATTGAAAACACATCTGATTTGCGTGACCAATGGAAACAAGAGGGA

AGTTATTGGTATTATTTTGATCGTGCAGGGAAAGCTCTTGTTAATAGTTGGAAGGGAAACTATTATCTCAAATCAAATGGTGTG

ATGGCACGTAATGAATGGGTTTATGATACAAACTATAAAGCTTGGTATTATCTCAAATCAGATGGAAGCTATGCACAAAATAGT

TGGCAAGGAAGTTACTACCTTAAGTCAGATGGAAAAATGGCACAAAGTGAGTGGCTATACGATTCCAGCTATAAAGCTTGGTAT

TATCTCAAGTCAGATGGAAGCTATGCACAAAATAGCTGGCAAGGAAGCTACTACCTTAAGTCAGATGGGAAAATGGCACAAAGT

GAGTGGCTATACGATTCCAGCTATAAAGCTTGGTATTATCTCAAGTCAGATGGAAGCTATGCACAAAATAGCTGGCAAGGAAGT

TACTACCTTAAGTCAGATGGAAAAATGGCACAAAGTGAGTGGCTATACGATTCCAGCTATAAAGCTTGGTACTATCTCAAATCA

GATGGAAGCTATGCACAAAATAGTTGGCAAGGAAGTTACTACCTTAAGTCAGATGGAAAAATGGCACAAAGTGAGTGGCTATAT

GATTCCAGTTATAAAGCTTGGTACTATCTCAAATCAGATGGAAGTTATCTGAGAGATCAATGGTTCAAGGACGGAAGTGCTTGG

TATTATTTGAAAGCAGATGGTAAGATGGCACAAAATGAGACGATTGGTGCTTATTATTTAGATTATTCTGGTAAGTGGATTTCT

TAA

>ZmpC2 (X231_0594)                                                         (SEQ ID NO: 14)
ATGAAAGAATTTCAATTTGAGCGAAAGCAGCGTTTTCTTTGAGGAAATATGCAATAGGAGCTTGTTCGGTCTTGCTAGGAACG

AGTTTATTTTTTGCTGGTATGGATGCTCAGCCTGTACAGGCTACCGAAACGAGTTCAACACTAATTTCAAGTCATTATTTGGAT

GAGCAGGATTTATCTGAAAAGCTGAAATCTGAGTTGCAATGGTTTGAAGAAAATAAGATTGAGGTAAAAGAGGGAAAAGAATAC

TACTTTGTCTATCGAAAATTGGCTACAAGATTACCAGAAACAGGTCTTTTTTCTAATGATGGGACGTTTATCCTGGGAGCAGGA

TTATTATTGCTTTCCTTCACTTTAATCAAGAGAAAAAGGGGAGCGTCTTACTTCCTTGTGACAGTCTTTGCTGTTGGTGGATGG

GGAGCATCCATCTCTGCTTTCGAAAATCTGGTAGAATTGCAACCAGCCCTTGTTAAGAGAGTAGAAGGTCAGTTTTTACCAAGT

CCTGAAAGAGTTCAAGGATATGAATTTACGGGATATTATTTGGTAAGAGATAGTGGTAACAAGGAACTTTCTGTCGATAAGGTA
```

```
GAGTCGCCAGCATTATCTCAAAAGGAGGACAGTTCAGAGCCTCAATCTAAGAAGATTGTACCACAGACTGCATCTTATTTCAGC
TCGACTGAAGACCTTGTGCAATCTCCTCAACCATCTTACGCAGTTGAGAAAATTGTTGAAGCTCCTGATGAAATGGTGCCTATA
GGGACTAAGGAAGAAGTTGCAGGAAATCCCCAAGTAGAACAACCGAAAGCAAAAGATAATAGTGATCATAAAACAAGTCCTGAG
GAAGGTGTGTTAAATGTCACAGTAGAGAAACCAGAATTGTTAATCACTACAGAGGAGGTTGCTTTCCAAACGATAGAACAAGAA
GATGCAACCTTAGCTAAAGGGCAAACTAAAGTTGTTCAAAAAGGTGTTGTTGGTGAACGCACCATCTATACGGAAGTCACTGTC
GTTAATGGGAAAAGTCTAGCAAAGTTATAGAAAATATAATCACAAAAGAACCAGTGAACAAGGTGATTGCAGTTGGGACTAAG
GAAGAAGTTGCACCAAAACCAACACAACCTGTAACTCCAGAGCCAGAGGAAGTTAAACCAGTTCAACCTGAAAAAACTCCAATA
GTAGAGAATGAAACAGAGACAAAACCAGTTGATGGAATAGGACAACCAACACCAGGAGCAGAAGAAACGCCGGGTACAGAAGCG
ACATCGGGCGAGAAACAAACACCTGATAAACCCGAAGCCGAGCCGAAGCAACCAGAACGAGAAGAAGATCAATCCCCTGTGGGA
CAAAAGGTTGAGGAGAACCAGCTGGAGAACTCAGTTGAGGGGGCAAAAGATGCTGGTGAAACTGCCCCACAAGAACCCCAAAAA
CAACCAGAACAAACGGCTCCATCTCCAGAGGTCAACCCAAGTCAAGGAAATGAACCAGCTCCAGCTGTTCAGCCTGACCCCTTA
GCTCCCCAAGAGCAGTCAGATTCACAAGTGCAACCAACTGTCCCGAGTCCAGTAACTAAAGAAAAAGTACTGGACTATAAAACA
ATCTATACAGCATCGCCAGCTTTAAATTACCAAGAGCAACAAGTAGAAGTAGCAGGCGAAAATGGTAAGGAAGTGATAACTACT
TCTTACAGTTTTGATGAAAGTACTGGGAAAATAGTAGAAAACACTTCGACAAAAATAGAGAAACAACCGGTGGATAGAATTGTT
AAGGTTGGGAATGTAGAAGAAACAAGATCAACAGTCAAAAGACGTGAACAGTTTGTCGCGGATGAGTCACTTGATAAAGGTGTC
AAAGAAGTCAGAAATCAAGGTCAGGACGAAGAAACAACCACTATTCGTGTTTATAAAGTAAATGAACAAACAGGATCTATCTCA
GAAGAAACTACAATAGAAAACACTCCAGCTAAAGATAAAGTAATAAAAGTAGGAAACGTAGAAAAGCTAGTGTCACCTATAGAA
ATCACTGAATTGAAGAAGAAGATTCAACACTTCCAAAAGGTAAAGAAAAAGTTGAAGATGCAGGTGAGCAAGGGGAAACAACC
GTCACTAAAACTTATGAAGTTAATCCGGAGACAGGAGAGTTAACAAATCCAGTAGAGAAAACTGAAACAACTAAAGCTATGCGC
CAAAAAGTAATCTTGGTTGGTACTAAAGAAGAGAAACCTCATTTACTCCCAGTTAATAGCGAATTAGAAAATGCAGTAAACGTA
ACGGAAGCTACTGCGGAGATGAGAAATGTAGACTTGTTGACAAATGAAAAGTTAAAAGCGCAGTTAGCTCCATCAGATATAGAA
ATAAATCGAGATTTATTCTTAAAACGAAAAGAATTACAAAAAACTAATCCGCAGATAAGGGATGATGAAGTAAGAGAAATTCTA
CGAAAAGAGTATCTTGAAAAATTATCGATTAAAGAAACACTCGATGCGACTAAAACCGATTTAGAAGTTAGTTTGAAAAAAGTT
GCGGCGCATACCTTGAGTATTTTAGGTGACAATCAACAAAATAGAGAAAAAGTAAAAGGTGATATTGAAGCTAATAAAGAAAA
ATATTATTAGGTCTATCCTATATCAATCGTTTTTATAATATTGATTTTGGAGATGCCAACATCCGTGATATTCTAGCTTATAAT
CCAAGCTCGTTCGGTAAAAAAGACCTTACTTCTTTAGATTGGTTAACACACCTTGGATCTATGAGTTATGATGAATTAAGATTA
ACGAATAGTCCAAAAACATTTGAGAAATACTTTAGTAAAATAACGAATAAGACTACACTATTAGATTTCCTAGACTACAATAGA
ATGACATTCACTAATATGGATGGCGATACGTGGTTGAAGAAAGCGACTAAAGCTATCGTAGTTGAAAAAGCTTCGAAAGAAAA
ACCGATGAAAAAGTAGAATTATATACTAAATTAACTACTGATCCTGAAAAATATGGAGCTGAAGGACTTCAAATAAATAATAGA
AAACAACAAAACATTGCTACATTGTTAGGTTTGGTGAACATTAAAGAACCAAGCGTGTATGCTATAACTAACATAGCGACGGTA
ACCTACGGAAACATCGGAACGTATATGGATACTTCTTTAGAGAAAACAAATAAAGCTAAGTATACCGGAGAGCTTAATAAGGTT
AAAGAATTGATAGAATTAACTGCGACAAGACAGGCTGCATACGTTGATACTTTATACAGAATTACAAAAGAAGAAATCGTTCT
AAATTAGTTACAAATAGAGTGATTGTAGACACGATGAAAAAATACACGACGGATACGTCTGCTGGAATAGGGACAACATGGTCT
AAAGAATCAGGACCAACAGCAGATAAAGGGGTTAAAGACTTTATGACACCTCTAGGACTGTATTCACCATCGCAAAATGTAGGT
GCAGAAGCGAATGGAGTGGGTGTCCGTTACTTCATAGATAGAGTTCTGGATGATAGAGGTTCAGCGACTTACTCTCACGAAATG
ACGCACTTACTAGATAGAACGGTCTTGTTTAATAATCATGGTCGTCGAGATGGTACAGGAGCAGAGTTTTATGCGCGTGGTATT
TTTGAAAACTCCTATAATCCAGAAAAGGATACTTATTTCAATCTCAACTTTGTATGTGATGAGAGTGATAAGAATGGATTTTAC
AATAGAACACCTGATCGATTTAAAACAGCAGAAGATTTGAAATCTTATATGAAGGGAAGTTTCGATGTCCTTTATACTCTAGAT
TATCTAGAAGCTGAGGCAAGTAGAGGCTTATCTACAGAAGACAAAATGAGTTATTTCAAAAAAATAGCGCCAATCACTTCATCA
GGTCCTAGAACTTGGGTAGATTACCGTAATACAGCGGTTAAACCGACTCATAAAAGTGAGGAAATTCAATCTCTGACCTTAGAA
GATGCCAAAAAATTGACAGATATTGATAGTTTGATTGACAATCATATCCTGGTCAATCGTTATATCATTGCTGGTTTTTCAGAT
```

-continued

AAAGGAAAAATTACAGCAAATGGTTATTATACCGTTGATATGTTTGATACCATTTATGGTGTTAGTCAAAATGACTCTGGTATG
AGTGGGGACATCACCTTTAGAAAACAAGCCTTTGAATTGATGGCTGCTTTGGGCTATTATGAAGGATTTGTTCCTTATGTGTCA
AATCAATACAAACAAGCAGCAGAGGCTGAGAACAAGCCTCTATCTGATACTTACATTTTCAATAAAATTTTGAATGGTAAGAGC
TATGCTGAGTTCAAAAAAGCACAGTTCAAGGAAAGAGTAGCTAAGATTGATCAATTGAAACCTTTGACAATCCAATATGAAGGT
CAGCAAATAAGTCTGACAAGTCAGAAGTTAAAAGAATTGATGCAGAAAGCTGTTCAAGAGGAGTTGAAACAGATTAAGGCAGGC
AAAACAACTGCGCGCACCTATACCTTTATTGAAACTCCAGTTCAAAAACTCAAAAAAGCGATTTATAAAGCTTATCTCAAAGAT
TCAGATGACTTTAGACAGTCGATTTACAATAGTTAA

>Nan01 (X231_0534)

(SEQ ID NO: 15)

ATGATTGGATTAGCTGCACCAGACTTACCAGTTATTGGTGGTGGAGTCGTTGCTGCTGATGTTATTCAGGGTGGTAACGATATA
AAAGATGTGAACGTTCATAGTAAATCGCGGAAGGTGTTGCTATGACCTATACCACTTATGATAGCGGAACAAGTGGAAAACAA
ACCGCATCAGGTAGCGGTGTCTTTGTAGCGCCGAATGTGATGGTAACAGTAGCTCATAACTACTATGATAAAAACCAAGAGGAT
AAGTCTGCGGTCTTGCGTGGTGGGGCGTCTGCTCGTAGTTATGTTGTGATGAACTCAGAGACGGAAAAGCACAATAAAGTACCT
ACTTCTGGTGTATCAGAAACTCTTGAAAAAGACTCTATTCATTTGTATGATGAGAAAAATTTTGGGAAAGACTATATCAACGAC
TTAGCAGTAGTGGTAACTAAAAAGACTGTAGAAGCTATGACAGGTGGTGAAGATTCACCAAGAGAATTGAGCCATAAAGAGGTT
TCTACTGGTGATAAAATCTCTATGGTCGGCTATCCTAATGACTTTTCAACTCCGAATTTAAGTGCAGAAAACAAAGCACGATTG
AAAGACGGTAAGGCTTATTCAGTTACAACAACTGTAAGTAGTGTCAATAAAGAGAGTGGTACAGTCACTTATCATTCCTCAGCT
TTAGGAGGTTTTTCAGGTGCTCCTTTGTTTAATGATAAGGGAGAGGTAGTCGGTATCCACCAACATGGGACAAATACTCCAAAC
GCTCAAGAAAGTGAGCGTATTGGTGGTGGTACCCTCTTTACGGAAAAGCACAGAGCTTGGATTCGTTCTATGATTGATAAATAT
GGTATAAAGGGTTGGTATATAGATGGTGCAAACCGTTACTACTATGATGAAAATCACAGAGCCTTAAAAGATGTAGAGTCTGAG
ATTGACGGTGCTTTGTATCGTTTTGATGAAAAAGGCCGAGCTACTTTACTAGAGGGTGAAGAAAAAGGTCGCGTTCTACTTCGA
GTGGAAGATACTAAAGGAACTCCTTTGATTTCAGATAAGGTTGTTCAAGAAGGTTCTGTTGGAAGTGGTTTGAATTTTCATTTA
AGACAAAATCCAAACTTCAAACAGTTAATAGCAACTTCTCCAACAGCTAAAGTGGTATCCTATAACGGAGTGCCAATTAACAAA
TTAGCAAGTGATACAAGTTGGTCTGATGAATATGTCAGTAAGTTAGCTTTGGGTGATACAATTATAAGAGCGGTAGTAGATTCG
GTAACTCCTCCATCTACGTCTTCTTCGGATTTTGCAAGAACTGAAGTTGGTAAGGTTGATTTGAGTGGTAAATCGAACTTACCT
GTGCCTAGTAAAGAGGTATTACAAGCTCCGAATGGTTCAGAAAACTTCTATGCTACAACGCATATTCAAACGCCAGATGGGTCG
GGGTCAGGTACTTTAATTGCACCAAATTTGGTGTTAACAGTCGCTCATAATTTCTTAACAGTTAAAGGTTCTGAGGTAGTTACG
AAGTCTGGTCGCACCAATACAGTGTATAAAGCTACTTTGCCAAGTGGTCAGCCTGTGAATTTTTCCGATGATGATATTGTTTAT
TGGAACAAGAAAGACTCAGTATTTGGATTTAAAAATGACTTAGCTTTGGTTCGTTTGAAAGAAAAGCTTACAGCGGTATCTCCT
GTAGAGGTGGTATCTGAGTCAACTTCGATTACTAAAGGTGACAAAGTTTCCGTTTATGGTTTTCCTGATGGTCGTTTGTCTCCA
GTTTTGGATAGTGAAGTAGTAGCTACTACTGACTTTGGTTCAGGTATTGAAGGGATTAGCTATGGTGGTACAAAACCCGGAGCT
TCTGGTGGTGGTCTTTATAATGACAAAGGTTCTTTAATTGGAGTTCACCAAAATGGTGTTGTAGGAAGCCGCAGTGGTGGGTTA
GTCTTATCAAAAGAACAATTAGATTGGGTTCGTTCCTATATTGAGGGTAAACCCAAAGCCCCTGTTTATGTAACAGATAATATT
TTGGTGGATGAAAAAGACAAGGATAAACTTCCATCAACTTCAAAAGAAGAAAAACCGACCACACCAAAAGTAGAGTCGGATAAA
GATAAACCAAATACACCTCTAAAACCGCAAGAAAAGCCGAAAACAGAGGTTATAACGAGTTATGAGGGTGATAGTACCCTTGAA
GTTGGGAAAGAGCGTACAGAGGAAACTGAGGGCGAAAAGAAGGTGTTTCCCTTATTTATCGAACGGTGTATAAAGGTACTAAA
TCGAAAACAGAAATGTCACCTATTGCCTTTGACACGGTTTACCAAGGAGATGAAACTAAAGAGCTTGGTTTCCGTTCAGTTTTA
GAGGGTAAAGAGGGTCTAGTTACTCGCACTACAAGTTACCAAGTAGATAAGTACACAGGAGCGGTATCCTCCAAGATTTCTGAA
GAGAAAATAGCACCTCAATCTCAAGTCATCACATTAGGTATTAAGAAAAATAGCAGCACAAAAGAAGTTCCAATTACAGAACGT
TTTGAAGATTCCGCAGAACTAGAGAAAGGTAAAACTGAGGTTATTTCTGAAGGTTCTGTAGGTAAAGAGGTTACTACGGTTACT
TATAAGGTTTTACCTGATGAAAGGTTATTGAAAATTCTCGTACAGTTGACGTTACACCCATGAGAGAGCGTGTAGTTCGTAAG
GGTGTGAAGGAAGTGGTATCTCCAGATAAAGTAGAGTCTCTAGTTCCAAAAGATGCGCCGATTAGAGAAGAGCAGCCTGCGCTT

-continued

AGTGAGGGATTTTCAGAGTCAGATGCTTTAGTATCAGGAGAAAAAATACAAGGAGATCTTGGGATACTTATAGTATCTTCAGAA

GAACTAGTCCCTGAAAGAGTAGAAGTTCCAGATTTTGTGACTAAAGTTACAGGTGGAGAAAAATTGACAGTAGAAGGGCACCGA

AATGAGAGTAAAATAAAGACTCCATCAAAACAGGAAAGATCATCTCGCCCAGAAACCACTGCTCAATTCACAACGAACGGGACA

GGTTCGTCATCGTTAACAGCTGTTTTTGGCGGTAAAACGGATAAAATATTACTTTCTACTGTTGAACATTCTGTTATTAAACAT

AATCAACAAAGAGGATGGCATAAGATAAATAATCAGTGGTATTTTAGAAATTCTGATGGGAAAGAACGGACAGGTTGGATGAAA

GAAAATGATGCATGGTATTATTTTGATACGAATGGAACCATGCAAACTGGTTGGCTAGAGGATACAGACGGTAATTGGTATTAT

CTCAATGATAATGGTAGGATGGAGATAGGCTGGTTCCAAGATTCAAGTGGCGCGTGGTACTACTTAGGATCATCTGGTCGCATG

GAATCCAATACATGGATTTATTATAAAGGAAAGTGGTACTATATTGATGCTTTGGGTAAACTACTTTTCAATTCGGTAACACCA

GACGGCTATAGAGTGAACGAGTATGGGAATGGATCAACTGA

>Nan02 (X231_0533)

(SEQ ID NO: 16)
TTGGAGAAAGTAAAGGGACTCCAAAATGCAACTGTTCATGTGGAGTTCAAACCGGCTGCTGATGGTCCTAGTTTTTACAATCTC

TTTTCTGCTTCCAGTACAACTAAAGTAAATGAATACTTTACAATGGCAATCAATAATGGGACAGCTTTGATAGAGGGACGTGGA

GCTGATGGTAGCCAATTTTATGGAAGTTATACAGATGCGCCTTTGAAGATTAGACCAGGCAAGTATAATTCGGTTACTTTTACT

GTTGAAAGACCAAGAAAGGATAGTCCAAATGGTCAGGTTCGTCTTTATGTGAATGGTGTATTATCTCGTACGAATAAAAAGTCA

GGGAAATTCCTGGCAGATATGCCAGATGTAGATAAACTCCAGTTAGGTGCAACTAATAGAGCAGGAGAACTGAAGTGGGGCTCA

GATCTTTCTATTCGTAATCTGACTGTATACAATCGTGCTCTAACTCCAGAGGAAGTCAAAAAACGTAGCCAGTTGTTTGATGTG

ATAGATATTGAGCCTTTACTTGCTGAAGGGGCAGTCTTGACAGAGAAGCAAGAGTTGTTTATGAGTGGTGTCAATGGTAAGCCA

AATAGTGAGGGAATTAAGAGTTATCGGATTCCACCTTTGCTACGTACGGATAAAGGAACATTACTGGCAGGGGCAGATCAGCGT

CGTCTCCACCATTCTGACTGGGGAGATATTGCTATGGTTGTTAGGAGAAGTGAGGATGGGGGAACTACTTGGCAGCCAACCTTA

ACCTTGACCAACCTGCGAGACAATCCAGAAGCAAAAGATCCGCAGGCATCATCTTCACTTAATATCGATATGGTCTTGGTTCAA

GATCCTACCACAAAGAGAATTTTTTCAATCTACGATATGTTTCCAGAGGGTCGAGCTGTCTTTGGAATGCCAAACAAACCTCAA

AAAGCTTATCAACAAGTTGGAGACAAGCACTATCAATTACTATATAAACAAGGGGAAAATCAAGCATATACTGTTCGAGAAAAC

GGGAGAAGTATATGATGCAAATAATCAAAAAACAGATTATCGCGTTGTAGTGGATCCAAAAGAAGAAGCCTATAGAGATAAGGGC

GACCTCTATAAAAGAGAAGAGCTTCTTGGGAATATCTACTTTGCTCAATCTGCTAAAACTCCATTTCGTGTAGCCTATACGAGC

TATTTGTGGCTTTCCTATAGTGATGATGATGGGAAAACTTGGTCGCAACCAAGAGATATTACACCATCAATTCGCCAAGATTGG

ATGAAATTTTTAGGAACAGGTCCAGGTACAGGAATTGTGCTTAGAACAGGAGAGCACAAGGGACGTATCCTAGTTCCCACTTAT

ACCACCAATGCTATCTCCCATCTAAGCGGCTCCCAGTCTTCACGTTTGATTTATTCAGATGATCATGGAGAAACATGGCAGGCT

GGAGCTGCTGTTAATGATGATAGGACGGTAGGCAGAAGGAAAATTCATTCCTCAACTATGAATAATAGGAATACCCAAAATACT

GAGTCAGTTGCTGTGCAGTTAAATAATGGTGATGTGAAACTCTTTATGAGAGGGTTAACGGGTGATTTACAGGTTGCCACAAGT

AAAGATGATGGGCAAACTTGGGACAAGGAAATCAAGAGATATAATCAGGTTAAAGATGTTTATGTCCAAATGGCTGCTATTCAC

ACCATGCACGAAGGAAAAGAATATATCATTTTAACCAATTCAGGAGGACTTAAACGGACGAATGGAATGGCTCATTTGGCTCGT

GTAGAGGACAACGGAGACTTGACTTGGTTACATCATAGACCAATTCAAAAAGGAGAGTTTGCCTATAATTCGCTTCAAGAATTA

GGAAATGGGAGTATGGTATCTTGTATGAACATACTGAAAAAGGACAAAATGACTATACCCTATCATTTAGAAAATTTAATTGG

GACTTTTTAACAAAGGATCCGGTATATCCAACGAGTGTAACTATCAGGGACGTTCGTAAATTGGAAACAGAAGAAGAGGATGCA

GAACAAGGCATCTTAGCTATGCAATTTGATTCTGAGGTACTAGTGAATGCTATTCCGACTTTGACTTTAGCGAATGGACACAAA

GCTACCTTCTTGACCCAAGCAGATCAAAAAACTCTACTTTTCACCTTTAATAAAGAAGATGCAGGTCAAGAAATTACAGGTCTA

ATGGCCGGTAGAATTGACAGTATGCATGATTTACCAGTTACACTAGCTGGTAGTAGAATTCCTGAAGATGCGAAAGAAAATCCT

GTCGAGACCATGAATACAGTAAGAGAAAATGTATCTGAGGAGATGACAGAAAGGAAGTCAGAGAAGGATAAATTATCTTTGGAG

TCTTCAGATAGAATGGTAGCAAACTCTCATCTTACTTCTTTTGCTCCTCGTTACCTCCAATCTTATGTAGGAGATGTTATTAAA

ACTGAGACTAAAGTTCCAATAACGACTGGTTGGAAGCAAGAAAATGGTGCGTGGTATTTTTATACATCTGCTGGTGAAGTGGTG

AAAGGCTGGCATCAGGAAGCGGATAAATGGTACTACTTGAGTTCTACTGGTGCGATGGCAACTGGTTGGGTCAGAGATGGTAAT

-continued

CAATGGTATTATTTGAGTGAGAGTGGAGCAATGTCTACTGGCTGGGTTGAATCCAGTGGTGTGTGGTACTATCTCCATTCTAAC

GGTTCAATGGCGACTGGTTGGATAAAAGATGGAGACCATTGGTACTATCAGGAATCATCTGGTGCAATGAGGGTAAATCAATGG

TTCCAAGTTGGAGACAAATGGTACTATGTCAATGAAAGCGGAAGATTAGCTGTTAATACCATAGTGGATGGTTATCAAGTTAAC

TCCAATGGAGAGTGGGTCAACTACTAG

>CbpI1 (BM49_0273)

(SEQ ID NO: 17)

ATGAAACAATTTTTAGAACGGGCCAGCATTTTGGCTCTCTCCCTCGTTTTGATTACCTCCTTTTCCATTTCGAGTGCCCTACCA

GCCATGTTTGACTATTATCAGGGTTATTCTAAGGAACAAATTGAGCTCTTGGTGAGCTTGCCTTCCTTTGGAATCATGATGATG

TTACTGCTAAATGGTTTCTTAGAAAAAATATTTCCTGAGCGCTTACAGATTAGTTTGGGCTTGCTGATTTTATCATTGAGCGGT

ACAGCTCCCTTCTGGTACCAAGCCTATCCCTTTGTCTTTGGAACACGGCTTCTCTTTGGTTTGGGTCTTGGGATGATCAATGCC

AAGGCCATTTCTATTATCAGTGAACGCTACCAAGGAAAAAGGCGAATTCAGATGTTAGGGCTACGCGCTTCTGCAGAGGTCGTT

GGAGCTTCTCTCATAACCTTGGCCGTCGGTCAGTTGTTGGCCTTTGGTTGGACAGCTATCTTTCTAGCCTATAGTGCTGGATTT

TTGGTGCTGCCCCTTTATCTGCTCTTTGTCCCTTATGGAAAATCAAAGAAAGAAGTCAAGAAAAGAGCGAAGGAAGCAAGTCGT

TTAACTCGAGAAATGAAAGGCTTGATTTTTACCTTAGCTATCGAAGCGGCAGTTGTAGTTTGTACCAATACAGCTATTACCATC

CGTATTCCAAGTTTGATGGTGGAAAGAGGATTGGGGGATGCCCAGTTATCTAGTTTTGTTCTTAGTATCATGCAGTTGATCGGG

ATTGTGGCTGGGGTGAGTTTTTCTTTCTTGATTTCTATCTTTAAAGAGAAACTGCTCCTCTGGTCTGGTATTACCTTTGGCTTG

GGGCAAATCGTGATTGCCTTGTCTTCATCCTTGTGGGTGGTAGTAGCAGGAAGTGTTCTGGCTGGATTTGCCTATAGTGTAGTC

TTGACGACGGTCTTTCAACTTGTCTCTGAACGAATTCCAGCTAAACTCCTCAATCAAGCAACTTCATTTGCTGTATTAGGCTGT

AGTTTCGGAGCCTTTACGACCCCATTTGTTCTAGGTGCAATTGGCTTACTAACTCACAATGGGATGTTGGTCTTTAGTATCTTA

GGAGGTTGGTTGATTGTAATCTCTATCTTTGTCATGTACCTACTTCAGAAGAGAGCTTAG

>CbpI2 (X231_0220)

(SEQ ID NO: 18)

ATGAAGAAAATTGTATTTGCTAGCGCCTTGGCCTTGACCTTGGCAGGAGCAGTTTTGACAAATGATGTTTTTGCGAATGACAGA

CTGGTTGCAACACAATCTACTGATGGTAATGTATTGACCTCAGAGGTGCTAAAACCTTCTAGTGGCAATGTTTTGGTTGGAATC

AAAGGAGAATTTTTGCCTCCTCATCAACAATCTATTTTAGATGCCATTAATAAAATTCGTAAAGAAGCAGCTGACGAAGGTTTG

GTAGATAAGTATGTTCCTGTCAAATGGTCAGTTGACCATGAGAAAACGGCTTTTGTACGCGCTGCTGAGGTATCCGTTACGTTG

AAGGCTGAACGTCTTTCCAGTAAAAACAACTGGACTGCATTTCCATCTGGTAATAGCCTAAGTGGAGAAGTCCTAGATTTGAAT

CCTGATGGATTTCTAAAAGCCATTGAGAATTGGCATGCTGAAAAGGCGAACTATGTGGCGAAAAAGAAAGATAAACATCAAAA

GAATTTTCATTTTATTATGAGAACTTGATTAACCCTAAATTTACCTATGTGGGTCTTGCTGCTTTTAAAAATGCAGCTAGTCCT

CAGAAGGCAGCAACCGTTGCTTTGGCTCTAGGAACTACGACTTCTTCAGAGGAATTGGCTGGTGGATATGGTTCTGCTGTTCAG

TACACAGAAGTGACTGCCTCAAACCTTTCAACAGTTAAAAGTAAAGCAATGGTTGTAGAAACACCGTTGAAAGATTTCAGAAAA

TCTACGTCTGATCAGTCTGGCTGGGTGCAGTCTAATGGCAAGTGGTATTTTTATGAGTCTGGTGATGTGAAGACAGGCTGGTTG

AAAACAGGTGGTAAATGGTACTACTTGAATGACCTAGGTGTTATGCAGACTGGATTTGTAGAAGTTGATGGATCGGTGTATTAT

CTAAGTAACTCAGGCGCTATGTTTACAGGCTGGGGAACAGATGGTAGCAGATGGTTCTACTGTGATGGCTCAGTAGCTATGAAA

ACAGGCTGGTACAAGGAAAATGGTACATGGTATTACCTTGATGAAGAAGGGATCATGAAGACGGGTTGGTTTAAAGTAGGTCAA

CACTGGTACTATGCAAATGGTTCAGGCGCTTTGGCTGTTAGCACAACAACACCAGATGGTTACCGTGTAAATGCTAATGGTGAA

TGGGTAAGCTAG

>CbpAC1 (X231_0613, representative of ST448, ST1186)

(SEQ ID NO: 19)

ATGTCTAAATCAAATCATGAAAGAAGAATGCGTTATTCTATTCGCAAATTTAGTGTAGGAGTGGCTAGTGTACTAGTAGCTAGC

TTCTTTATGGGGAGTGTTGCTCATGCAAGTGGGCTTGTAAAGGATGATAGTGTTAAGACTACGGAGATTGCAGCTACTAATAGA

GAAAAGAAAATGATGCGAAGTCTGGCTGGGGAGGTATCATTGATGGTAGTGGAAAACTATTGGGTGGATTTTCTGAAATAAAA

GAAAAGTTGAAAAAGAGATAGACGAATCCAGTCTCACGTCAGAGCAAAAGAAATCCTATAAGGAAAAAATTGTTAAGGTAAAA

CAAAATGATGTAGACGGGTTGTTTGGTGTTCACAGAGAATACTTAAACCAACTAGACTTTCAATATCTTGAACTATCCAAAGTT

-continued

```
GAGGAAGAGTTTAAATACCAAGAGGAACAGATCCAAAGGATGTTCGAGCAAAAAGGCATTACGAATGAAGATAAGGATGCTATG

CTGAAAAAATAGCAGAAATCCATCAAGAGGCCGAAAAAGATATTAAGGCTTCAGGAGGCTATCGTGATAAGCTAAATGGAACA

AAAGTTAAGTTTCTTCAGAACTTGGACAAGCTTTTCACCTCGACAAAATCAAAATTTGAAAAGGAAATGCAAGAGCTCTATCGC

AAGAAAGAGGCAGAAATTGTTAAGGAAAAGCATTTAGAAAAAGATAAGATTTATGACGATGCTGACGTTCAAAAACTTCGTGAG

CTAGAAAAGATGCACTGAAAAAATTGGACGAGGCAAAAACAAATGATGAAGCGCTCAGAGTGAAGTTGGAATTTGCTCGAAAC

GTTGAGAAAAATAGCCAACAAGTGCAAAAATAGATGATAAGTTGCAAGAGTTGATTAAAGAAGCCAAACGTGAACTGGAAAAA

TTAAATCAAGGAATTGCAGAAGTTGATAAGTTACCAGAATTACCAGCTAATGATTCTGATTATATGGTACAGAAAAAATATATC

TGGGACGAAGACAAAGAAACTATACCTAAAAAAATTGCAAAATTTAAAGAGAATTTGGGAAATAAAACGTATACTAAGGAATCG

TTACAGAAGTTTATAGATGATTGTATTTATTACCAAACTCATGCGAAAATCGAAGTCATGACTAGAAAGGTAGCTGGTTATAGA

AAAGCATATCCTAATAATCCAGAAATTGAAAAGGAATTTGTAAGCCATATCAAACAAACAAGTAGCTTAACATATGCTAGTTTA

GAAAATGATAGCTTAAAACGTTATTTTGAAAAAGATTTCGCTCCGGCTTTTGAGCGAATCAAGCAGATTGTAGAAGGACTGGAG

AAACCACACACCCCGGCGCAACCCGGTATTGAAAATCAGAAGCCATCTGCTCCAAAAACAGAGAAGTCAGCTGAACAACCAAAA

GCAGGCTGGAAACAAGAAAACGGTATGTGGTACTTCTACAATACTGATGGTTCAATGGCGACAGGATGGCTCCAAAACAACGGT

TCATGGTACTATCTAAACGCTAATGGTGCTATGGCGACAGGATGGCTCCAAAACAATGGTTCATGGTACTACCTCAACGCTAAC

GGTTCAATGGCAACAGGATGGCTCCAAAACAATGGCTCATGGTACTACCTCAACGCTAACGGTTCAATGGCAACAGATTGGGTG

AAAGATGGAAATACCTGGTACTATCTTGAAGCATCAGGTGCTATGAAAGCAAGCCAATGGTTCAAAGTATCAGATAAATGGTAC

TATGTCAATGGCTTAGGTGCCCTTGTAGTCAACACAACTGTAGATGGCTATAGAGTCAATGCCAATGGTGAATGGGTAAGCTAA

>CbpAC2 (BM51_0858 representative of ST1270, ST344, ST2315)
                                                                    (SEQ ID NO: 20)
TTATTTTCTTCTTTTCATCGCGATTAATGAAGTTCCAGCCAAACCAAGGAGACCAATGATTTCAAGAACTAAATTAGTTGCTGC CCCTGTGGATGGCAAATTCTTCTCAGTTGCTGATGTAGGATTTTCTTTTGCCATTGTTTCATTTCCAGTAGCCAGTGGTTTATG ATTAACTTCTTTATTCTGGAATTTTCCAGTTTGGTTTTCTCCTATCTGTGTTTGACCATGTTGGACAGAAGGTTTAATCTGCTT AGGTGTGGTGACATTTTGATTCTTAGAAAGTGTCTTAATCGCAAACAAACTGAAGTGGTTGGTTTTAAAGACAACTTGCCCATT TTCAACTTTAGAAGGAATACGCTCAAGGTCACCATTTTCCTTTACGTGATAGACGTGAACATCTGATGCAGTCTGCCCAAGCGC CAGCCTAACAGTTCGTTCTCCATTGACATGAGTTTCCTTGCCTCCTTTAGATAAAGAAAGATCAAAGATGCGAACAGTTCCTCC ACCAGTTTGGCGAGCGATTTTTTCAGCCAACTCCTTCGTCGTCACTTCCTTTATATTTACCTTATCAGCATCAACAGCCTTATC AAATACAACCGTAACCTTAGTTTTCCCGTCAGAAGCTGTAATGATTTTTGAAGTTTTTGGGGTTTCTGGTTGTGGTTTAACCTC TGGTTTTGGTTTTTCTGGTTGTGGAATCGGCTTTTCCTGTGTTGGAACAGACGGTTTTTGTTCTCCGGTTCTTTCGGTGTACT TGGTTGCTTACCGTCTGGCTGTGGGATTGGTTTAGGTTCCGGACTTGTACTCGGAACTTCTGGCTGAGGTTGAAGGTCTGGTTT GGTATCCGGGGCTGGCATTGAAGGTTTTTGATCACCTGCTTGCGCTCTTCCACTGTCTGATTTAATTTTTTCTAGGGTTTTAAC CTTGCTCTTAGCTGTTTCTACCTTGGCTTTAGCAGTATTAATTTTGTCAGTATCTTGAGGTGTTTGGGCTTGAGCTTGTGCAAG CTCGAGCTCTGCCTTTGCGACTTCTACTTGTGCTTCCGCAATTTCCAGTTCGATTGTTTTACTAGTATTGGTTGGGTAGTTACG GCGATCTTCTTCTTTTTGAGCCTTGGCTTTTTTCTCAGCCTCTTCAACCTTCTTCTGAGCTTCTGCTACCTTGTCCTGTTTCTT GAGCTCTCCCTGACTTGATTTCTTTTCTAGTTCCTCGATAATACTGTGGATTTTGTTAAAGACCGGTAAAAAGTCTCTTTCAAA ATACGTTTTCAAGGCTTCCCCCTCTAAGGTAGCATAAGTACTGTTAGCCGTTTGTTTTAGCTTTTCAGAAAATAGTCTTTCAAC TTCAGCCACATTAGGATGTTTTTTCTATATGTGGCTATCTTTCTAGTCATCGTCTCAATTTGTGCATGAAATTGATAATAGAT AAATTCAGCAACAGCATCTTTTAAAGTTTTTTCTGTATAGGTCTGTTTTTCAAGCTGTTCTTTGAATACCTGGATTTTCTTAGG CGCAGTATCCTTACTATTATCCCAAATATCTTTTTTCTGCACTTTGTAATCTGGATCATTATCCGGTAGCTCTGGATAGTTATT GACTTCTCTGAGATAGTCCTCTAGCTTTTTCAATTCTTCTTGGCCTTGACGAATCAAGTCTTGTAACTTTTTCTTTTCAGCTTC GGTCGCCTTTTGTCCTGGACTTGGGGAAGTTGATGGAGGTGTTTGCGTCACCGGTGGTACAACCATTGAACCGCCTGCTTGTCC TCCTGGTTGGGGTACGACTCCAGGTCCTTGTCCTACTGAAGGGTCACCCCCCCCCTGTAAACCATCATTTAGAGAGAGCCCTTT AGGAGTACTTTTACTACCTGAACGATTTTGAAATAACTTTATTTCTTCATCTACTTTTTTCTTAACTTCCCTTCCCAGCTCCTC
```

```
TACCATGCTTTTAGTAGAAACTCTATCAATCTTATCTCTGTATTTATCTACAACCACCTGAACCTTTGTGACAATTTCTGAAAA

TCCAGAAACAGATCGATCCAGTGAGTCTAAACGACTAGTCACATAGTCCGAAATTTCTTTGTTAACTCTTTGTACAGCATCCTC

ATATTCTTTTTTATCACCTGGAGATACTATTTGTGGAATAGGGGATTAGCAGAAACATTCTCTGTCGCATGAACCACACTTCC

CATAAAAAGACTGGCAACAGCTACACTAGCCACTCCTACACTAAATTTGCGAATAGAATAACGCATTCTTCTTTCATGATTTGA

TTTAGACAT
```

---

What is claimed is:

1. A composition comprising:
    two or more isolated peptide antigens, comprising (i) peptide antigens comprising one or more antigenic epitopes from SspBC1 (SEQ ID NO: 1) and (ii) peptide antigens comprising one or more antigenic epitopes from one or more of
    SspBC2 (SEQ ID NO: 2), PspO (SEQ ID NO: 3), ZmpC2 (SE ID NO: 4), NanO1 (SEQ ID NO: 5), NanO2 (SEQ ID NO: 6), CbpI1 (SEQ ID NO: 7), CbpI2 (SEQ ID NO: 8), CbpAC1 (SEQ ID NO: 9) or CbpAC2 (SEQ ID NO: 10); and
    an amount of adjuvant effective to enhance an immune response.

2. The composition according to claim 1, comprising peptide antigens comprising one or more antigenic epitopes from SspBC1 and peptide antigens comprising one or more antigenic epitopes from one, two, three, or all four of cbpAC1, cbpAC2, nanO1, and nanO2.

3. The composition according to claim 1, comprising peptide antigens comprising one or more antigenic epitopes derived from SspBC1 and peptide antigens comprising one or more antigenic epitopes from one, two, three, or all four of cbpAC1, cbpAC2, nanO1, nanO2, and SspBC2.

4. A composition according to claim 1, further comprising an antigen delivery system.

5. A composition according to claim 1, further comprising a pharmaceutically acceptable excipient.

6. A composition according to claim 1, wherein said composition is a vaccine.

7. A method for inducing an immunoprotective response in a subject against an infection with *Streptococcus pneumoniae* comprising administering a composition according to claim 1.

8. A method of treating or reducing risk of an infection of *Streptococcus pneumoniae* comprising administering a composition according to claim 1.

9. The method of claim 7, wherein the infection is an ocular infection.

10. The method of claim 9, wherein the infection is conjunctivitis.

11. The composition of claim 1, comprising peptide antigens comprising one or more antigenic epitopes from SspBC1 and peptide antigens comprising one or more antigenic epitopes from SspBC2.

12. The composition of claim 1, comprising peptide antigens comprising one or more antigenic epitopes from SspBC1 and peptide antigens comprising one or more antigenic epitopes from one or both of NanO1 and NanO2.

13. The composition of claim 1, comprising peptide antigens comprising one or more antigenic epitopes from SspBC1 and peptide antigens comprising one or more antigenic epitopes from one or both of CbpI1 and CbpI2.

14. The composition of claim 1, comprising peptide antigens comprising one or more antigenic epitopes from SspBC1 and peptide antigens comprising one or more antigenic epitopes from one or both of CbpAC1 and CbpAC2.

* * * * *

SEQUENCE LISTING

<160> NUMBER OF SEQ ID NOS: 28

<210> SEQ ID NO 1
<211> LENGTH: 1646
<212> TYPE: PRT
<213> ORGANISM: Streptococcus pneumonia

<400> SEQUENCE: 1

```
Met Leu Leu Leu Ile Lys Arg Lys Glu Gly Leu Phe Met Thr Lys Gln
 1               5                  10                  15

Cys His His Phe Leu Val Asn Gln Glu Gln Ala Glu Lys His Val
            20                  25                  30

Phe Arg Lys Ser Lys Lys Tyr Arg Thr Leu Cys Ser Val Ala Leu Gly
         35                  40                  45

Thr Met Val Thr Ala Val Ala Trp Gly Gly Gln Val Ala Gln Ala
     50                  55                  60

Asp Glu Val Thr Met Pro Pro Leu Asp Lys Thr Val Gln Leu Thr Glu
65                  70                  75                  80

Asn Asn Ala Thr Asn Leu Pro Glu Ala Gln Pro Ala Pro Val Ala Glu
                85                  90                  95

Gln Thr Asp Ser Leu Phe Ser Thr Gly Gln Ser Asp Gly Thr Ile Thr
            100                 105                 110

Val Thr Val Pro His Asp Thr Val Thr Asn Ala Ile Asn Gln Ala Thr
         115                 120                 125

Ala Glu Gly Leu Thr Thr Ile Gln Asp Lys Pro Met Asp Leu Gly Asn
     130                 135                 140

Thr Thr Ser Ala Ser Glu Thr Ser Lys Gln Leu Asp Thr Ala Glu Ala
145                 150                 155                 160

Asp Ala Ala Lys Gln Ala Glu Asp Ile Thr Arg Val Thr Asn Thr Tyr
                165                 170                 175

Lys Ala Asp Lys Val Ala Tyr Glu Gln Asp Lys Thr Arg Val Glu Lys
            180                 185                 190

Gly Asn Ala Ala Leu Val Ala Ser His Lys Glu Ala Thr Gln Ala Gly
         195                 200                 205

Lys Ala Leu Asn Ser Ser Val Asp Thr Thr Ala Ser Glu Val Lys Thr
     210                 215                 220

Gln Asp Lys Ser Ala Asn Val Thr Ile Thr Gln Thr Val Pro Ser
225                 230                 235                 240

Gly Glu Gly Ser Thr Val Ser Gly Tyr Gln Asp Tyr Thr Ser Ala Val
                245                 250                 255

Ala Ala Ile Asp Lys Gln Asn Lys Ala Ser Leu Ala Asp Tyr Ile Thr
            260                 265                 270

Lys Lys Gln Ala Ala Asp Ala Ile Thr Ala Lys Asn Leu Ala Val Gln
         275                 280                 285

Lys Glu Asn Glu Ala Gly Leu Ala Asn Ala Lys Ala Glu Asn Glu Ala
     290                 295                 300
```

-continued

Ile Thr Lys Arg Asn Gln Ala Gly Gln Lys Ala Ile Asp Asp Glu Asn
305                 310                 315                 320

Lys Ala Gly Gln Ala Ala Val Asp Thr Tyr Asn Lys Asn Gln Gln Lys
            325                 330                 335

Leu Val Thr Asp Arg Glu Asp Glu Ile Ala Ala Ile Lys Arg Asn
            340                 345                 350

Lys Glu Lys Glu Glu Ala Ala Lys Lys Glu Asn Glu Ala Ile Asp Ala
            355                 360                 365

Tyr Asn Ala Lys Glu Met Asn Arg Tyr Lys Arg Asp Leu Ala Asp Ile
370                 375                 380

Ser Lys Gly Glu Glu Gly Tyr Ile Ser Gln Ala Leu Ala Gln Ala Leu
385                 390                 395                 400

Asn Leu Asn Asn Gly Glu Pro Gln Ala Arg His Ser Ala Asp Thr Arg
            405                 410                 415

Asn Pro Asn Arg Ile Ile Ala Lys Gly Asp Ala Met Leu Gly Gly Tyr
            420                 425                 430

Ser Lys Ile Leu Asp Ser Thr Gly Phe Phe Val Tyr Asp Thr Phe Lys
            435                 440                 445

Thr Gly Glu Thr Leu Ser Phe Thr Tyr Gln Asn Leu Gln Asn Ala Ser
450                 455                 460

Phe Asp Gly Lys Lys Ile Thr Lys Val Ala Tyr Asp Ile Thr Asn Leu
465                 470                 475                 480

Val Ser Pro Thr Gly Thr Asp Ser Val Gln Leu Val Pro Asn Asp
            485                 490                 495

Pro Thr Glu Gly Phe Ile Ala Tyr Arg Asn Asp Gly Thr Gly Asn Trp
            500                 505                 510

Arg Thr Asp Lys Met Glu Phe Arg Val Lys Ala Lys Tyr Phe Leu Glu
            515                 520                 525

Asp Gly Ser Gln Val Ser Phe Thr Lys Glu Lys Pro Gly Val Phe Thr
530                 535                 540

His Ser Ser Leu Asn His Asn Asp Ile Gly Leu Glu Tyr Val Lys Asp
545                 550                 555                 560

Thr Ser Gly Lys Phe Val Pro Ile Asn Gly Ser Thr Ile Gln Val Thr
            565                 570                 575

Asp Glu Asp Leu Ala Arg Ser Leu Ser Ser Asn Arg Ala Ser Asp Leu
            580                 585                 590

Asn Leu Pro Glu Glu Trp Asp Thr Ser Phe Ser Lys Tyr Ala Tyr Lys
            595                 600                 605

Gly Ala Ile Val Ser Thr Val Thr Ser Gly Asn Thr Tyr Thr Val Thr
            610                 615                 620

Phe Gly Gln Gly Asp Met Pro Gln Asn Ala Gly Leu Thr Tyr Trp Phe
625                 630                 635                 640

Ala Leu Asn Thr Leu Pro Val Ala Arg Thr Val Lys Pro Tyr Ser Pro
            645                 650                 655

Lys Pro His Val Thr Pro Lys Leu Asp Pro Val Pro Glu Pro Ile Lys
            660                 665                 670

Val Val Pro Lys Thr Phe Thr Pro Lys Thr Phe Thr Pro Glu Pro Pro
            675                 680                 685

Val Ile Phe Lys Glu Lys Pro Leu Glu Lys Val Thr Gln Pro Arg Leu
            690                 695                 700

Thr Leu Thr Lys Val Thr Phe Ala Lys Glu Pro Arg Ser Glu Pro Leu
705                 710                 715                 720

Pro Lys Ala Pro Gln Val Pro Thr Val His Tyr Asp Tyr Arg Leu
                725                 730                 735

Thr Thr Thr Pro Glu Ile Met Lys Lys Val Val Asn Thr Asp Gln Asp
            740                 745                 750

Asn Leu His Asp Lys Thr Ile Ala Lys Asp Ser Thr Val Ile Tyr Pro
            755                 760                 765

Leu Thr Val Asp Val Phe Ser Ser Asn Arg Ala Lys Thr Thr Thr Leu
        770                 775                 780

Thr Phe Glu Asp Tyr Leu Pro Ala Gly Tyr Ala Phe Asp Lys Glu Lys
785                 790                 795                 800

Thr Gln Ala Glu Asn Glu Asn Tyr Thr Leu Thr Phe Asp Glu Ala Lys
                805                 810                 815

Asn Phe Val Thr Leu Thr Ala Lys Glu Ala Leu Leu Gln Glu Val Asn
            820                 825                 830

Gln Asp Leu Thr Lys Ser Tyr Gln Leu Val Ala Pro Lys Leu Tyr Gly
        835                 840                 845

Ser Leu Gln Asn Asp Gly Ala Thr Tyr Ser Asn Ser Tyr Lys Leu Leu
    850                 855                 860

Ile Asn Lys Gly Thr Ser Asn Ala Tyr Thr Val Thr Ser Asn Val Val
865                 870                 875                 880

Thr Val Arg Thr Pro Gly Asp Gly Lys Ile Thr Ser Arg Ile Thr Pro
                885                 890                 895

Gln Lys Arg Asn Glu Asn Glu Asp Gly Val Val Ile Asn Asp Thr Val
            900                 905                 910

Val Ala Leu Gly Thr Thr Asn His Tyr Arg Leu Thr Trp Asp Leu Asp
        915                 920                 925

Gln Tyr Lys Gly Asp Thr Ser Ser Lys Glu Thr Ile Ala Arg Gly Phe
    930                 935                 940

Phe Phe Val Asp Asp Tyr Pro Glu Glu Val Leu Asp Leu Val Asp Lys
945                 950                 955                 960

Gly Thr Ser Ile Thr Thr Leu Asp Gly Lys Ala Val Ser Gly Ile Thr
                965                 970                 975

Val Lys Ala Tyr Val Ser Leu Ser Glu Ala Pro Lys Asp Leu Gln Asp
            980                 985                 990

Lys Leu Ala His Ala Lys Ile Ser Pro Lys Gly Ala Phe Gln Ile Phe
        995                 1000                1005

Gln Pro Asn Asp Asn Gln Ala Phe Tyr Asp Gln Tyr Val Lys Thr Gly
    1010                1015                1020

Thr Ser Leu Asn Leu Leu Thr Lys Met Thr Val Lys Asp Ser Leu Tyr
1025                1030                1035                1040

Gly Gln Thr Lys Thr Tyr Arg Asn Lys Ala Tyr Gln Val Asp Phe Gly
                1045                1050                1055

Asn Gly Tyr Lys Thr Asn Glu Val Thr Asn Thr Leu Val Ser Pro Thr
            1060                1065                1070

Pro Lys Lys Gln Asn Leu Asn Lys Asp Lys Val Asp Ile Asn Gly Lys
        1075                1080                1085

Pro Met Val Val Gly Ser Gln Asn Tyr Tyr Thr Leu Ser Trp Asp Leu
    1090                1095                1100

Asp Gln Tyr Arg Gly Ile Lys Ala Asp Lys Ala Gln Ile Ala Lys Gly
1105                1110                1115                1120

Phe Tyr Phe Val Asp Asp Tyr Pro Glu Glu Ala Val Leu Pro Asp Asp
                1125                1130                1135

Thr Ala Ile Gln Leu Thr Thr Ser Asn Gly Lys Ala Val Ile Gly Val

```
                    1140                1145                1150
Thr Val Lys Asn Tyr Thr Ser Leu Ser Glu Val Pro Lys Pro Leu Gln
                1155                1160                1165

Ala Ala Phe Glu Lys Arg Lys Ile Ala Pro Lys Gly Ala Phe Gln Val
            1170                1175                1180

Phe Met Ala Glu Asp Pro Gln Ala Phe Tyr Asp Ser Tyr Val Thr Lys
1185                1190                1195                1200

Gly Gln Asn Ile Thr Ile Val Thr Pro Met Thr Val Arg Glu Glu Met
                    1205                1210                1215

Leu Asn Ser Gly Lys Ser Tyr Asp Asn Val Ala Tyr Gln Val Asp Phe
                1220                1225                1230

Gly Gln Val Tyr Glu Thr Asn Thr Val Thr Asn His Val Pro Lys Val
            1235                1240                1245

Asn Pro His Lys Thr Asn Thr Asn Lys Glu Gly Val Ser Ile Asp Gly
        1250                1255                1260

Lys Thr Val Leu Pro Asn Thr Val Asn Tyr Tyr Lys Ile Val Leu Asp
1265                1270                1275                1280

Tyr Ser Gln Tyr Lys Asp Leu Val Val Thr Glu Asp Thr Leu Ala Lys
                    1285                1290                1295

Gly Phe Tyr Met Val Asp Asp Tyr Pro Glu Ala Leu Thr Leu Asn
                1300                1305                1310

Ala Asp Gly Val Gln Val Met Asp Lys Ala Gly Asn Leu Val Lys Gly
            1315                1320                1325

Ile Ser Val Lys Ala Tyr Ala Ser Leu Ser Glu Ala Pro Gln Val Val
        1330                1335                1340

Gln Glu Ala Met Ala Lys Arg Gln Leu Thr Pro Lys Gly Ala Ile Gln
1345                1350                1355                1360

Val Leu Ser Ala Asp Asp Pro Lys Val Phe Tyr Glu Thr Tyr Val Lys
                    1365                1370                1375

Thr Gly Gln Thr Leu Val Val Thr Leu Pro Met Thr Ile Lys Asn Glu
                1380                1385                1390

Leu Thr Lys Thr Gly Gly Lys Tyr Glu Asn Thr Ala Tyr Gln Ile Asp
            1395                1400                1405

Phe Gly Leu Ala Tyr Val Thr Glu Thr Val Val Asn Asn Val Pro Lys
        1410                1415                1420

Leu Asp Pro Gln Lys Asp Val Val Ile Asp Leu Ser Gln Lys Glu Asn
1425                1430                1435                1440

Ser Leu Asp Gly Lys Glu Val Ala Leu Asn Gln Val Phe Asn Tyr Arg
                    1445                1450                1455

Leu Val Gly Val Leu Ile Pro Gly Asn Arg Ala Thr Pro Leu Ile Glu
                1460                1465                1470

Tyr Arg Phe Asp Asp Asp Tyr Asp Glu Ser His Asp Asp Tyr Asn Gly
            1475                1480                1485

Val Tyr Thr Ala Tyr Thr Val Val Asp Val Thr Leu Lys Asp Gly Thr
        1490                1495                1500

Val Leu Leu Lys Gly Thr Glu Val Thr Lys Tyr Thr Leu Gln His Val
1505                1510                1515                1520

Asp Thr Ser Lys Gly Thr Val Thr Ile Ser Phe Asp Lys Glu Phe Leu
                    1525                1530                1535

Glu Lys Leu Ala Glu Glu Ser Glu Phe Gln Ala Asp Val Tyr Leu Gln
                1540                1545                1550

Met Lys Arg Ile Ala Ser Gly Glu Val Glu Asn Thr Val Leu His Thr
            1555                1560                1565
```

```
Val Asn Gly Tyr Thr Ile Ser Ser Asn Thr Val Lys Thr Thr Thr Pro
        1570                1575                1580

Glu Pro Glu Pro Pro Thr Pro Asn Gln Pro Thr Pro Pro Gln Pro Pro
1585                1590                1595                1600

Ile Pro Thr Gln Glu Pro Pro Val Pro Ala Ser Val Leu Pro Asn Thr
                1605                1610                1615

Gly Glu Ser Gln Ser Leu Leu Ala Leu Val Gly Gly Gly Leu Leu Leu
                1620                1625                1630

Gly Leu Ala Tyr Val Leu Ala Lys Arg Lys Met Glu Asp Asn
                1635                1640                1645

<210> SEQ ID NO 2
<211> LENGTH: 1833
<212> TYPE: PRT
<213> ORGANISM: Streptococcus pneumonia

<400> SEQUENCE: 2

Met His Lys Ala Arg Glu Thr Lys Thr Tyr Gly Ser Ile Arg Lys Ser
1               5                   10                  15

Lys Ile Tyr Gly Thr Cys Gly Val Ile Leu Gly Leu Ala Ala Leu Ser
            20                  25                  30

Met Ile Ser Pro Val Ile Ala Asp Glu Arg Thr Glu Asn Lys Ala Thr
        35                  40                  45

Asn Ala Pro Tyr Ala Gln Thr Ser Pro Ser Ser Ile Ser Thr Glu Asn
    50                  55                  60

Gln Gly Lys Ser Glu Lys Thr Gly Thr Leu Glu Val Ser Ile Ser
65                  70                  75                  80

His Ser Ser Leu Asp Glu Thr Ile Arg Lys Ala Gln Glu Ala Gly Leu
                85                  90                  95

Lys Val Glu Phe Asp Ser Val Val Asp Lys Gly Thr Ala Ser Thr Ala
            100                 105                 110

Ser Glu Leu Glu Lys Lys Gln Lys Glu Val Ser Asp Tyr Cys Thr
            115                 120                 125

Gln Ala Asp Ser Ile Glu Lys Ala Thr Glu Lys Tyr Arg Glu Asp Gln
        130                 135                 140

Arg Gln Asn Gln Thr Asn Arg Lys Lys Ile Gln Asp Glu Asn Thr Ala
145                 150                 155                 160

Lys Lys Glu Gln Tyr Gln Lys Asp Leu Thr Ser Tyr Gln Ala Glu Val
                165                 170                 175

Asn Arg Ile Asn Gln Lys Asn Ala Ser Ile Arg Ala Glu Asn Glu Lys
            180                 185                 190

Asn Gln Arg Glu Asn Gln Ala Glu Ile Asp Arg Ile Asn Gln Glu Asn
        195                 200                 205

Ala Glu Ile Arg Lys Arg Asn Glu Ala Lys Arg Gly Ala Tyr Glu Ser
    210                 215                 220

Ser Leu Thr Asp Tyr Thr Lys Lys Leu Ala Thr Ile Lys Ala Glu Arg
225                 230                 235                 240

Asp Ala Ile Gln Thr Ser Lys Pro Leu Phe Gly Ser Glu Thr Gly Phe
                245                 250                 255

Lys Val Tyr Gly Gly Tyr Asn Ser Ala Gly Arg Gly Ser Leu Asp Tyr
            260                 265                 270

Tyr Asn Asp Phe Thr Val Val Pro Asp Asp Asn Leu Pro Val Glu Ser
        275                 280                 285

Met Arg Gly Phe Leu Gly Tyr His Ala Asp Thr Tyr Val Thr Gly Gly
```

```
              290                 295                 300
Ala Gly Thr Arg Val Ser Lys Asp Ser Thr Glu Thr Tyr Asp Ile Ile
305                     310                 315                 320

Lys Ser Pro Thr Phe Gly Asp Thr Phe Tyr Ile His Asn Ile Gly Thr
                325                 330                 335

Leu Thr Asp Gly Arg Lys Ile Met Ala Lys Val Met Val Ser Asp Leu
                340                 345                 350

Gly Asp Tyr Gln Gly Glu Val Arg Asn Gly Val Pro Val Thr Asp Ser
                355                 360                 365

Asp Ile Tyr Leu Lys Gly Gly Asp Gly Ser Phe Tyr Phe Val Tyr
370                 375                 380

Asn Asn His Thr Arg Leu Glu Met Val Phe Asp Phe Tyr Ile Glu Gly
385                     390                 395                 400

Thr Thr Thr Pro Val Ser Leu Leu Ile Gly Thr Val Ile Thr Asp Val
                405                 410                 415

Asp Trp Gly Gln Gly Ser Asn Leu Ser Tyr Gly Ser Ser Gly Arg Gly
                420                 425                 430

Met Val Leu Asn Pro Ser Gly Ser Gly Leu Asp Phe Asp Gly Arg Val
                435                 440                 445

Met Lys Gly Val Glu Asn Gly Val Asn Asp Thr Ser Asp Ile Pro Lys
450                     455                 460

Ala Ser Phe Ala Ser Val Gly Tyr Gly Ser Ser Leu Thr Tyr Leu His
465                     470                 475                 480

Thr Ser Ser Pro Gly Ser Thr Glu Gly Arg Thr Pro Ala Glu Trp Asp
                485                 490                 495

Ala Glu Asn Leu Ser Gly Asn Ala Gln Asn Val Val Phe Thr Ile Leu
                500                 505                 510

Gly Glu Gly Ala Glu Leu Lys Ser Ile Pro Pro Val Asn Pro Pro Arg
                515                 520                 525

Lys Pro Thr Tyr Glu Val Glu Thr Thr Pro Pro Asn Ser Pro Thr Gly
                530                 535                 540

Lys Pro Glu Glu Val Leu Pro Pro Lys Pro Glu Glu Ile Lys Glu Lys
545                     550                 555                 560

Glu Ile Pro Ser Leu Val Ser Pro Pro Thr Val Arg Val Arg Tyr Ala
                565                 570                 575

Arg Leu Gln Ala Met Pro Asp Leu Glu Lys Phe Val Lys Asn Ser Ser
                580                 585                 590

Gly Glu Ser Ile Asp Lys Ser Tyr Val Pro Lys Leu Ser Thr Val Gln
                595                 600                 605

Trp Glu Leu Thr Thr Lys Pro Leu Pro Ala Asn Arg Glu Ala Ile Thr
610                     615                 620

Asp Phe Glu Ile Val Asp Ala Leu Pro Ser Gly Phe Val Leu Asp Val
625                     630                 635                 640

Glu Ala Ser Lys Lys Ile Ser Ser Asp Phe Glu Leu Thr Tyr Asp Glu
                645                 650                 655

Ser Ser His Val Val Arg Met Lys Gly Leu Glu Ser Leu Lys Ser Lys
                660                 665                 670

Leu Asn Gln Asp Leu Ser Lys Glu Val Gln Val Pro Ala Pro Ile Leu
                675                 680                 685

Val Gly Lys Val Thr Asn Asp Gly Ala Thr Tyr Lys Asn Asn Phe Gln
                690                 695                 700

Leu Lys Ile Asn Asn Lys Tyr Glu Ser Tyr Ser Asn Ile Val Gln Ile
705                     710                 715                 720
```

```
Ser Thr Pro Gly Lys Pro Asn Asp Pro Asp Asn Pro Asn Asn Asn Phe
            725                 730                 735

Ile Gln Pro Leu Lys His Asn Tyr Asn Lys Asp Lys Val Ile Ile Asp
            740                 745                 750

Gly Lys Ser Val Leu Val Gly Ser Thr Asn Tyr Tyr His Ile Thr Leu
            755                 760                 765

Asp Tyr Asp Gln Tyr Lys Gly Met Lys Ala Asp Ser Ser Thr Ile Leu
            770                 775                 780

Lys Gly Phe Gly Ala Ile Asp Asp Tyr Pro Glu Glu Ala Val Thr Ile
785                 790                 795                 800

Asn Gln Ser Asp Ile Arg Tyr Ile Asp Ser Glu Gly Lys Glu Val Ala
            805                 810                 815

Gly Ile Ser Val Tyr Gln Tyr Asp Ser Ile Asp Ala Val Asp Asn Asp
            820                 825                 830

Lys Val Lys Ala Phe Leu Ala Ser Ser Glu Ile Lys Pro Lys Gly Ala
            835                 840                 845

Phe Gln Val Phe Leu Val Asp Asp Pro Glu Ala Tyr Phe Asn Gln Tyr
            850                 855                 860

Ile Lys Ser Gly Lys Ser Val Thr Ile Ile Asp Pro Met Val Thr Lys
865                 870                 875                 880

Glu Glu Leu Arg Asn Thr Gly Lys Ser Phe Glu Asn Thr Ala Tyr Gln
            885                 890                 895

Val Asp Phe Gly Asn Gly Tyr Gln Thr Asp Thr Val Val Asn Asn Val
            900                 905                 910

Pro Thr Val Lys Pro Thr Lys Lys Asn Leu Asn Lys Ala Gly Val Asn
            915                 920                 925

Ile Asp Gly Lys Gln Val Leu Ala Gly Phe Val Asn Tyr Tyr Lys Val
            930                 935                 940

Thr Ala Asp Tyr Ser Gln Tyr Lys Gly Ile Glu Ala Asp Lys Asp Arg
945                 950                 955                 960

Ile Gly Lys Gly Phe Tyr Ile Val Asp Asp Tyr Pro Glu Glu Ala Val
            965                 970                 975

Thr Ile Asn Gln Asp Gly Val Gln Val Thr Asp Ser Lys Gly Gln Val
            980                 985                 990

Val Lys Gly Leu Lys Met Ala Leu Tyr Asp Ser Leu Asp Lys Ala Pro
            995                 1000                1005

Ser Gly Val Gln Glu Ser Leu Glu Ser Ser His Phe Thr Pro Lys Gly
            1010                1015                1020

Ala Ile Gln Val Phe Glu Ala Glu Asn Pro Glu Glu Phe Tyr Lys Thr
1025                1030                1035                1040

Tyr Val Gln Ala Gly Glu Val Leu Thr Ile Thr Asn Pro Met Thr Val
            1045                1050                1055

Lys Lys Glu Leu Gly Gln Thr Gly Gly Lys Tyr Glu Asn Thr Ala Tyr
            1060                1065                1070

Gln Leu Asp Phe Gly Ser Gly Tyr Gln Thr Asp Lys Val Glu Asn Asn
            1075                1080                1085

Val Pro Thr Ala Lys Pro Thr Lys Lys Asn Leu Asn Lys Ala Gly Val
            1090                1095                1100

Asn Ile Asp Gly Lys Gln Val Leu Ala Gly Ser Val Asn Tyr Tyr Lys
1105                1110                1115                1120

Val Thr Ala Asp Tyr Ser Gln Tyr Arg Gly Ile Glu Ala Asp Lys Asp
            1125                1130                1135
```

-continued

Arg Ile Gly Lys Gly Phe Tyr Ile Val Asp Asp Tyr Pro Glu Ala
            1140                1145                1150

Val Thr Ile Asn Gln Asp Gly Val Gln Val Thr Asp Ser Lys Gly Gln
        1155                1160                1165

Val Val Lys Gly Leu Lys Met Ala Leu Tyr Asp Ser Leu Asp Lys Ala
        1170                1175                1180

Pro Ser Gly Val Gln Lys Ala Leu Lys Ser Ser Asn Phe Thr Pro Lys
1185                1190                1195                1200

Gly Ala Ile Gln Val Phe Glu Ala Glu Asn Pro Glu Glu Phe Tyr Lys
            1205                1210                1215

Thr Tyr Val Gln Ala Gly Glu Ile Leu Thr Ile Thr Asn Pro Met Thr
        1220                1225                1230

Val Lys Lys Glu Leu Gly Gln Thr Gly Gly Lys Tyr Glu Asn Thr Ala
        1235                1240                1245

Tyr Gln Val Asp Phe Gly Asn Gly Tyr Gln Thr Asp Thr Val Val Asn
        1250                1255                1260

Asn Val Pro Thr Val Lys Pro Thr Lys Asn Leu Asn Lys Ala Gly
1265            1270                1275                1280

Val Asn Ile Asp Gly Lys Gln Val Leu Ala Gly Ser Val Asn Tyr Tyr
        1285                1290                1295

Lys Val Thr Ala Asp Tyr Ser Gln Tyr Arg Gly Ile Glu Ala Asp Lys
        1300                1305                1310

Asp Arg Ile Gly Lys Gly Phe Tyr Ile Val Asp Asp Tyr Pro Glu Glu
            1315                1320                1325

Ala Val Thr Ile Asn Gln Asp Gly Val Gln Val Thr Asp Ser Lys Gly
        1330                1335                1340

Gln Val Val Lys Gly Leu Lys Met Ala Leu Tyr Asp Ser Leu Asp Lys
1345                1350                1355                1360

Ala Pro Ser Gly Val Gln Lys Ala Leu Lys Ser Ser Asn Phe Thr Pro
            1365                1370                1375

Lys Gly Ala Ile Gln Val Phe Glu Ala Glu Asn Pro Glu Glu Phe Tyr
        1380                1385                1390

Lys Thr Tyr Val Gln Ala Gly Glu Ile Leu Thr Ile Thr Asn Pro Met
    1395                1400                1405

Thr Val Lys Lys Glu Leu Gly Gln Thr Gly Gly Lys Tyr Glu Asn Thr
    1410                1415                1420

Ala Tyr Gln Ile Asp Phe Gly Ser Ala Tyr Ile Thr Glu Thr Val Val
1425                1430                1435                1440

Asn Asn Val Pro Thr Ala Lys Pro Thr Lys Asn Leu Asn Lys Ala
            1445                1450                1455

Gly Val Asn Ile Asp Gly Lys Gln Val Leu Ala Gly Ser Ile Asn Tyr
        1460                1465                1470

Tyr Lys Val Thr Ala Asp Tyr Ser Gln Tyr Lys Gly Ile Glu Ala Asp
        1475                1480                1485

Lys Asp Arg Ile Gly Lys Gly Phe Tyr Ile Val Asp Asp Tyr Pro Glu
    1490                1495                1500

Glu Ala Val Thr Ile Asn Gln Asp Gly Val Gln Val Thr Asp Ser Lys
1505                1510                1515                1520

Gly Gln Val Val Lys Gly Leu Lys Met Ala Leu Tyr Asp Ser Leu Asp
            1525                1530                1535

Lys Ala Pro Ser Gly Val Gln Glu Ser Leu Lys Ser Ser His Phe Thr
        1540                1545                1550

Pro Lys Gly Ala Ile Gln Val Phe Glu Ala Glu Asn Pro Glu Glu Phe

```
                    1555              1560              1565
Tyr Lys Thr Tyr Val Gln Ala Gly Glu Val Leu Thr Ile Thr Asn Pro
        1570              1575              1580

Met Thr Val Lys Lys Glu Leu Gly Gln Thr Gly Gly Lys Tyr Glu Asn
1585              1590              1595              1600

Thr Ala Tyr Gln Val Asp Phe Gly Met Ala Tyr Val Thr Glu Thr Ala
                1605              1610              1615

Val Asn Asn Val Pro Lys Ile Glu Pro Lys Lys Asp Val Val Ile Asp
                1620              1625              1630

His Leu Ser Lys Glu Ser Leu Asp Gly Lys Glu Val Lys Met Asn Gln
                1635              1640              1645

Thr Phe Asn Tyr Lys Leu Val Gly Ser Leu Val Pro Lys Asp Arg Ser
                1650              1655              1660

Glu Gln Leu Phe Glu Tyr Lys Phe Ser Asp Asp Tyr Asp Glu Thr His
1665              1670              1675              1680

Asp Glu Tyr Gln Gly Val Tyr Gln Val Phe Ala Thr Val Asp Phe Glu
                1685              1690              1695

Thr Ser Asp Gly Gln Lys Phe Lys Ala Gly Asp Glu Leu Thr Lys Phe
                1700              1705              1710

Thr Ser Gln Val Val Asp Lys Ala Lys Gly Lys Val Asp Ile Ser Phe
                1715              1720              1725

Asp Gly Ala Phe Leu Lys Ser Ile Leu Glu Thr Ser Glu Phe Gln Ala
                1730              1735              1740

Glu Val Tyr Leu Gln Met Thr Arg Ile Gln Ser Gly Ala Val Glu Asn
1745              1750              1755              1760

Thr Tyr Tyr His Thr Val Asn Gly Val Glu Val Val Ser Asn Thr Val
                1765              1770              1775

Val Thr Gln Thr Pro Glu Glu Pro Lys Thr Pro Glu His Pro Gln
                1780              1785              1790

Gln Pro Glu Arg Ser Leu Pro Ser Thr Gly Glu Gln Ala Ser Ala Glu
                1795              1800              1805

Leu Leu Leu Ala Gly Leu Thr Met Gly Ser Leu Ala Thr Gly Leu Leu
                1810              1815              1820

Tyr Ser Lys Arg Lys Lys Lys Glu Ala
1825              1830

<210> SEQ ID NO 3
<211> LENGTH: 644
<212> TYPE: PRT
<213> ORGANISM: Streptococcus pneumonia

<400> SEQUENCE: 3

Met Lys Leu Arg Thr Thr Ile Leu Ala Thr Thr Ala Ser Val Thr Leu
1               5                   10                  15

Leu Gly Leu Gly Asn Ser Gln Pro Val Tyr Ala Asn Ser Thr Thr Ser
                20                  25                  30

Ser Gln Val Glu Ser Leu Lys Ser Glu Phe Ile Lys Ala Lys Arg Glu
            35                  40                  45

Tyr Glu Gln Ala Lys Ser Ile Tyr Asp Asn Ala Leu Ser Ser Ser Pro
        50                  55                  60

Ser Asn Thr Ile Ile Leu Ser Asp Lys Tyr Ile Lys Ala Leu Lys Thr
65                  70                  75                  80

Ala Phe Ser Asp Phe Asn Ile Ser Gln Thr Glu Arg Asp Ser Ala Lys
                85                  90                  95
```

```
Ser Ile Leu Gln Ser Glu Ser Leu Arg Leu Lys Asn Gln Asn Ser Phe
            100                 105                 110
His Lys Asp Val Ala Asp Glu Gly Glu Arg Leu Asp Val Asn Asn Leu
    115                 120                 125
Pro Leu Ala Val Arg Gln Glu Leu Ser Phe Phe Ala Gln Asp Leu Ile
130                 135                 140
Asn Gln Val Arg Ser Gln Val Gly Thr Pro Arg Val Ser Val Ser Ile
145                 150                 155                 160
Ser Ala Leu Asp Phe Ala Asp Lys Val Ala Lys Ala Tyr Val Gln Asp
                165                 170                 175
Asn Trp Gly Trp His Lys Met Ser Val Ser Gly Thr Leu Gly His Asp
            180                 185                 190
Ala Thr Gly Ile Asn His Val Ala Arg Glu Tyr Gly Leu Pro Thr Thr
        195                 200                 205
Asn Ser Glu Glu Glu Lys Lys Gly Glu Gln Asn Tyr Glu Asn Leu Ala
210                 215                 220
Ser Arg Leu Pro Gly Phe Lys Thr Ala Asn Lys Ala Gln Leu Lys Glu
225                 230                 235                 240
Ala Ile Tyr Ile Gly Met Ile Glu Phe Met Phe Asn Asp Thr Glu Trp
                245                 250                 255
Met His Ala Gln Ser Ile Ala Gly Leu Asn Trp Gly Asn Val Asn Ser
            260                 265                 270
Lys Asp Tyr Phe Gly Leu Ser Phe Ser Ser Arg Ser Ser Val Ser Ser
        275                 280                 285
Ala His Phe Ile Thr Val Ser Gln Glu Asp Ile Lys Arg Ala Ser Lys
    290                 295                 300
Ser Ser Phe Ser Thr Ala Ala Val Ser Asp Pro Thr Ser Val Asn Arg
305                 310                 315                 320
Arg Gln Ala Ile Lys Lys Leu Glu Glu Asp Tyr Lys Ala Lys Glu Lys
                325                 330                 335
Ile Tyr Gln Asp Phe Gln Lys Gln Ala Asp Ser Lys Gly Ser Gln Gly
            340                 345                 350
Gln Ser Asn Gln Gly Ser Ala Thr Val Thr Glu Pro Ser Lys Pro Ser
        355                 360                 365
Ala Gly Ser Ala Glu Pro Thr Lys Ser Ile Glu Asn Thr Ser Asp Leu
370                 375                 380
Arg Asp Gln Trp Lys Gln Glu Gly Ser Tyr Trp Tyr Phe Asp Arg
385                 390                 395                 400
Ala Gly Lys Ala Leu Val Asn Ser Trp Lys Gly Asn Tyr Tyr Leu Lys
                405                 410                 415
Ser Asn Gly Val Met Ala Arg Asn Glu Trp Val Tyr Asp Thr Asn Tyr
            420                 425                 430
Lys Ala Trp Tyr Tyr Leu Lys Ser Asp Gly Ser Tyr Ala Gln Asn Ser
        435                 440                 445
Trp Gln Gly Ser Tyr Tyr Leu Lys Ser Asp Gly Lys Met Ala Gln Ser
    450                 455                 460
Glu Trp Leu Tyr Asp Ser Ser Tyr Lys Ala Trp Tyr Tyr Leu Lys Ser
465                 470                 475                 480
Asp Gly Ser Tyr Ala Gln Asn Ser Trp Gln Gly Ser Tyr Tyr Leu Lys
                485                 490                 495
Ser Asp Gly Lys Met Ala Gln Ser Glu Trp Leu Tyr Asp Ser Ser Tyr
            500                 505                 510
Lys Ala Trp Tyr Tyr Leu Lys Ser Asp Gly Ser Tyr Ala Gln Asn Ser
```

-continued

```
            515                 520                 525

Trp Gln Gly Ser Tyr Tyr Leu Lys Ser Asp Gly Lys Met Ala Gln Ser
        530                 535                 540

Glu Trp Leu Tyr Asp Ser Ser Tyr Lys Ala Trp Tyr Tyr Leu Lys Ser
545                 550                 555                 560

Asp Gly Ser Tyr Ala Gln Asn Ser Trp Gln Gly Ser Tyr Tyr Leu Lys
                565                 570                 575

Ser Asp Gly Lys Met Ala Gln Ser Glu Trp Leu Tyr Asp Ser Ser Tyr
            580                 585                 590

Lys Ala Trp Tyr Tyr Leu Lys Ser Asp Gly Ser Tyr Leu Arg Asp Gln
        595                 600                 605

Trp Phe Lys Asp Gly Ser Ala Trp Tyr Tyr Leu Lys Ala Asp Gly Lys
        610                 615                 620

Met Ala Gln Asn Glu Thr Ile Gly Ala Tyr Tyr Leu Asp Tyr Ser Gly
625                 630                 635                 640

Lys Trp Ile Ser

<210> SEQ ID NO 4
<211> LENGTH: 1523
<212> TYPE: PRT
<213> ORGANISM: Streptococcus pneumonia

<400> SEQUENCE: 4

Met Lys Glu Phe Gln Phe Glu Arg Lys Lys Arg Phe Ser Leu Arg Lys
1               5                   10                  15

Tyr Ala Ile Gly Ala Cys Ser Val Leu Leu Gly Thr Ser Leu Phe Phe
            20                  25                  30

Ala Gly Met Asp Ala Gln Pro Val Gln Ala Thr Glu Thr Ser Ser Thr
        35                  40                  45

Leu Ile Ser Ser His Tyr Leu Asp Glu Gln Asp Leu Ser Glu Lys Leu
    50                  55                  60

Lys Ser Glu Leu Gln Trp Phe Glu Glu Asn Lys Ile Glu Val Lys Glu
65                  70                  75                  80

Gly Lys Glu Tyr Tyr Phe Val Tyr Arg Lys Leu Ala Thr Arg Leu Pro
                85                  90                  95

Glu Thr Gly Leu Phe Ser Asn Asp Gly Thr Phe Ile Leu Gly Ala Gly
            100                 105                 110

Leu Leu Leu Leu Ser Phe Thr Leu Ile Lys Arg Lys Arg Gly Ala Ser
        115                 120                 125

Tyr Phe Leu Val Thr Val Phe Ala Val Gly Gly Trp Gly Ala Ser Ile
    130                 135                 140

Ser Ala Phe Glu Asn Leu Val Glu Leu Gln Pro Ala Leu Val Lys Arg
145                 150                 155                 160

Val Glu Gly Gln Phe Leu Pro Ser Pro Glu Arg Val Gln Gly Tyr Glu
                165                 170                 175

Phe Thr Gly Tyr Tyr Leu Val Arg Asp Ser Gly Asn Lys Glu Leu Ser
            180                 185                 190

Val Asp Lys Val Glu Ser Pro Ala Leu Ser Gln Lys Glu Asp Ser Ser
        195                 200                 205

Glu Pro Gln Ser Lys Lys Ile Val Pro Gln Thr Ala Ser Tyr Phe Ser
    210                 215                 220

Ser Thr Glu Asp Leu Val Gln Ser Pro Gln Pro Ser Tyr Ala Val Glu
225                 230                 235                 240

Lys Ile Val Glu Ala Pro Asp Glu Met Val Pro Ile Gly Thr Lys Glu
```

```
            245                 250                 255
Glu Val Ala Gly Asn Pro Gln Val Glu Gln Pro Lys Ala Lys Asp Asn
            260                 265                 270

Ser Asp His Lys Thr Ser Pro Glu Glu Gly Val Leu Asn Val Thr Val
            275                 280                 285

Glu Lys Pro Glu Leu Leu Ile Thr Thr Glu Glu Val Ala Phe Gln Thr
            290                 295                 300

Ile Glu Gln Glu Asp Ala Thr Leu Ala Lys Gly Gln Thr Lys Val Val
305                 310                 315                 320

Gln Lys Gly Val Val Gly Glu Arg Thr Ile Tyr Thr Glu Val Thr Val
            325                 330                 335

Val Asn Gly Glu Lys Ser Ser Lys Val Ile Glu Asn Ile Ile Thr Lys
            340                 345                 350

Glu Pro Val Asn Lys Val Ile Ala Val Gly Thr Lys Glu Glu Val Ala
            355                 360                 365

Pro Lys Pro Thr Gln Pro Val Thr Pro Glu Pro Glu Glu Val Lys Pro
            370                 375                 380

Val Gln Pro Glu Lys Thr Pro Ile Val Glu Asn Glu Thr Glu Thr Lys
385                 390                 395                 400

Pro Val Asp Gly Ile Gly Gln Pro Thr Pro Gly Ala Glu Glu Thr Pro
            405                 410                 415

Gly Thr Glu Ala Thr Ser Gly Glu Lys Gln Thr Pro Asp Lys Pro Glu
            420                 425                 430

Ala Glu Pro Lys Gln Pro Glu Arg Glu Glu Asp Gln Ser Pro Val Gly
            435                 440                 445

Gln Lys Val Glu Glu Asn Gln Leu Glu Asn Ser Val Glu Gly Ala Lys
            450                 455                 460

Asp Ala Gly Glu Thr Ala Pro Gln Glu Pro Lys Gln Pro Glu Gln
465                 470                 475                 480

Thr Ala Pro Ser Pro Glu Val Asn Pro Ser Gln Gly Asn Glu Pro Ala
            485                 490                 495

Pro Ala Val Gln Pro Asp Pro Leu Ala Pro Gln Glu Gln Ser Asp Ser
            500                 505                 510

Gln Val Gln Pro Thr Val Pro Ser Pro Val Thr Lys Glu Lys Val Leu
            515                 520                 525

Asp Tyr Lys Thr Ile Tyr Thr Ala Ser Pro Ala Leu Asn Tyr Gln Glu
            530                 535                 540

Gln Gln Val Glu Val Ala Gly Glu Asn Gly Lys Glu Val Ile Thr Thr
545                 550                 555                 560

Ser Tyr Ser Phe Asp Glu Ser Thr Gly Lys Ile Val Glu Asn Thr Ser
            565                 570                 575

Thr Lys Ile Glu Lys Gln Pro Val Asp Arg Ile Val Lys Val Gly Asn
            580                 585                 590

Val Glu Glu Thr Arg Ser Thr Val Lys Arg Glu Gln Phe Val Ala
            595                 600                 605

Asp Glu Ser Leu Asp Lys Gly Val Lys Glu Val Arg Asn Gln Gly Gln
            610                 615                 620

Asp Glu Glu Thr Thr Thr Ile Arg Val Tyr Lys Val Asn Glu Gln Thr
625                 630                 635                 640

Gly Ser Ile Ser Glu Glu Thr Thr Ile Glu Asn Thr Pro Ala Lys Asp
            645                 650                 655

Lys Val Ile Lys Val Gly Asn Val Glu Lys Leu Val Ser Pro Ile Glu
            660                 665                 670
```

```
Ile Thr Glu Leu Lys Lys Glu Asp Ser Thr Leu Pro Lys Gly Lys Glu
            675                 680                 685

Lys Val Glu Asp Ala Gly Glu Gln Gly Glu Thr Thr Val Thr Lys Thr
        690                 695                 700

Tyr Glu Val Asn Pro Glu Thr Gly Glu Leu Thr Asn Pro Val Glu Lys
705                 710                 715                 720

Thr Glu Thr Thr Lys Ala Met Arg Gln Lys Val Ile Leu Val Gly Thr
                725                 730                 735

Lys Glu Glu Lys Pro His Leu Leu Pro Val Asn Ser Glu Leu Glu Asn
            740                 745                 750

Ala Val Asn Val Thr Glu Ala Thr Ala Glu Met Arg Asn Val Asp Leu
        755                 760                 765

Leu Thr Asn Glu Lys Leu Lys Ala Gln Leu Ala Pro Ser Asp Ile Glu
    770                 775                 780

Ile Asn Arg Asp Leu Phe Leu Lys Arg Lys Glu Leu Gln Lys Thr Asn
785                 790                 795                 800

Pro Gln Ile Arg Asp Asp Glu Val Arg Glu Ile Leu Arg Lys Glu Tyr
                805                 810                 815

Leu Glu Lys Leu Ser Ile Lys Glu Thr Leu Asp Ala Thr Lys Thr Asp
            820                 825                 830

Leu Glu Val Ser Leu Lys Lys Val Ala Ala His Thr Leu Ser Ile Leu
        835                 840                 845

Gly Asp Asn Gln Gln Asn Arg Glu Lys Val Lys Gly Asp Ile Glu Ala
    850                 855                 860

Asn Lys Glu Lys Ile Leu Leu Gly Leu Ser Tyr Ile Asn Arg Phe Tyr
865                 870                 875                 880

Asn Ile Asp Phe Gly Asp Ala Asn Ile Arg Asp Ile Leu Ala Tyr Asn
                885                 890                 895

Pro Ser Ser Phe Gly Lys Lys Asp Leu Thr Ser Leu Asp Trp Leu Thr
            900                 905                 910

His Leu Gly Ser Met Ser Tyr Asp Glu Leu Arg Leu Thr Asn Ser Pro
        915                 920                 925

Lys Thr Phe Glu Lys Tyr Phe Ser Lys Ile Thr Asn Lys Thr Thr Leu
    930                 935                 940

Leu Asp Phe Leu Asp Tyr Asn Arg Met Thr Phe Thr Asn Met Asp Gly
945                 950                 955                 960

Asp Thr Trp Leu Lys Lys Ala Thr Lys Ala Ile Val Glu Lys Ala
                965                 970                 975

Ser Lys Glu Lys Thr Asp Glu Lys Val Glu Leu Tyr Thr Lys Leu Thr
            980                 985                 990

Thr Asp Pro Glu Lys Tyr Gly Ala Glu Gly Leu Gln Ile Asn Asn Arg
        995                 1000                1005

Lys Gln Gln Asn Ile Ala Thr Leu Leu Gly Leu Val Asn Ile Lys Glu
    1010                1015                1020

Pro Ser Val Tyr Ala Ile Thr Asn Ile Ala Thr Val Thr Tyr Gly Asn
1025                1030                1035                1040

Ile Gly Thr Tyr Met Asp Thr Ser Leu Glu Lys Thr Asn Lys Ala Lys
                1045                1050                1055

Tyr Thr Gly Glu Leu Asn Lys Val Lys Glu Leu Ile Glu Leu Thr Ala
            1060                1065                1070

Thr Arg Gln Ala Ala Tyr Val Asp Thr Leu Tyr Arg Ile Thr Lys Glu
        1075                1080                1085
```

-continued

Glu Asn Arg Ser Lys Leu Val Thr Asn Arg Val Ile Val Asp Thr Met
1090                1095                1100

Lys Lys Tyr Thr Thr Asp Thr Ser Ala Gly Ile Gly Thr Thr Trp Ser
1105                1110                1115                1120

Lys Glu Ser Gly Pro Thr Ala Asp Lys Gly Val Lys Asp Phe Met Thr
            1125                1130                1135

Pro Leu Gly Leu Tyr Ser Pro Ser Gln Asn Val Gly Ala Glu Ala Asn
            1140                1145                1150

Gly Val Gly Val Arg Tyr Phe Ile Asp Arg Val Leu Asp Asp Arg Gly
            1155                1160                1165

Ser Ala Thr Tyr Ser His Glu Met Thr His Leu Leu Asp Arg Thr Val
1170                1175                1180

Leu Phe Asn Asn His Gly Arg Arg Asp Gly Thr Gly Ala Glu Phe Tyr
1185                1190                1195                1200

Ala Arg Gly Ile Phe Glu Asn Ser Tyr Asn Pro Glu Lys Asp Thr Tyr
            1205                1210                1215

Phe Asn Leu Asn Phe Val Cys Asp Glu Ser Asp Lys Asn Gly Phe Tyr
            1220                1225                1230

Asn Arg Thr Pro Asp Arg Phe Lys Thr Ala Glu Asp Leu Lys Ser Tyr
            1235                1240                1245

Met Lys Gly Ser Phe Asp Val Leu Tyr Thr Leu Asp Tyr Leu Glu Ala
1250                1255                1260

Glu Ala Ser Arg Gly Leu Ser Thr Glu Asp Lys Met Ser Tyr Phe Lys
1265                1270                1275                1280

Lys Ile Ala Pro Ile Thr Ser Ser Gly Pro Arg Thr Trp Val Asp Tyr
            1285                1290                1295

Arg Asn Thr Ala Val Lys Pro Thr His Lys Ser Glu Glu Ile Gln Ser
            1300                1305                1310

Leu Thr Leu Glu Asp Ala Lys Lys Leu Thr Asp Ile Asp Ser Leu Ile
            1315                1320                1325

Asp Asn His Ile Leu Val Asn Arg Tyr Ile Ile Ala Gly Phe Ser Asp
            1330                1335                1340

Lys Gly Lys Ile Thr Ala Asn Gly Tyr Tyr Thr Val Asp Met Phe Asp
1345                1350                1355                1360

Thr Ile Tyr Gly Val Ser Gln Asn Asp Ser Gly Met Ser Gly Asp Ile
            1365                1370                1375

Thr Phe Arg Lys Gln Ala Phe Glu Leu Met Ala Ala Leu Gly Tyr Tyr
            1380                1385                1390

Glu Gly Phe Val Pro Tyr Val Ser Asn Gln Tyr Lys Gln Ala Ala Glu
            1395                1400                1405

Ala Glu Asn Lys Pro Leu Ser Asp Thr Tyr Ile Phe Asn Lys Ile Leu
            1410                1415                1420

Asn Gly Lys Ser Tyr Ala Glu Phe Lys Lys Ala Gln Phe Lys Glu Arg
1425                1430                1435                1440

Val Ala Lys Ile Asp Gln Leu Lys Pro Leu Thr Ile Gln Tyr Glu Gly
            1445                1450                1455

Gln Gln Ile Ser Leu Thr Ser Gln Lys Leu Lys Glu Leu Met Gln Lys
            1460                1465                1470

Ala Val Gln Glu Glu Leu Lys Gln Ile Lys Ala Gly Lys Thr Thr Ala
            1475                1480                1485

Arg Thr Tyr Thr Phe Ile Glu Thr Pro Val Gln Lys Leu Lys Lys Ala
            1490                1495                1500

Ile Tyr Lys Ala Tyr Leu Lys Asp Ser Asp Asp Phe Arg Gln Ser Ile

| | | | |
|---|---|---|---|
|1505|1510|1515|1520|

Tyr Asn Ser

<210> SEQ ID NO 5
<211> LENGTH: 1161
<212> TYPE: PRT
<213> ORGANISM: Streptococcus pneumonia

<400> SEQUENCE: 5

Met Ile Gly Leu Ala Ala Pro Asp Leu Pro Val Ile Gly Gly Gly Val
1               5                   10                  15

Val Ala Ala Asp Val Ile Gln Gly Gly Asn Asp Ile Lys Asp Val Asn
            20                  25                  30

Val His Ser Lys Ser Ala Glu Gly Val Ala Met Thr Tyr Thr Thr Tyr
        35                  40                  45

Asp Ser Gly Thr Ser Gly Lys Gln Thr Ala Ser Gly Ser Gly Val Phe
    50                  55                  60

Val Ala Pro Asn Val Met Val Thr Val Ala His Asn Tyr Tyr Asp Lys
65                  70                  75                  80

Asn Gln Glu Asp Lys Ser Ala Val Leu Arg Gly Gly Ala Ser Ala Arg
                85                  90                  95

Ser Tyr Val Val Met Asn Ser Glu Thr Glu Lys His Asn Lys Val Pro
            100                 105                 110

Thr Ser Gly Val Ser Glu Thr Leu Glu Lys Asp Ser Ile His Leu Tyr
        115                 120                 125

Asp Glu Lys Asn Phe Gly Lys Asp Tyr Ile Asn Asp Leu Ala Val Val
    130                 135                 140

Val Thr Lys Lys Thr Val Glu Ala Met Thr Gly Gly Glu Asp Ser Pro
145                 150                 155                 160

Arg Glu Leu Ser His Lys Glu Val Ser Thr Gly Asp Lys Ile Ser Met
                165                 170                 175

Val Gly Tyr Pro Asn Asp Phe Ser Thr Pro Asn Leu Ser Ala Glu Asn
            180                 185                 190

Lys Ala Arg Leu Lys Asp Gly Lys Ala Tyr Ser Val Thr Thr Thr Val
        195                 200                 205

Ser Ser Val Asn Lys Glu Ser Gly Thr Val Thr Tyr His Ser Ser Ala
    210                 215                 220

Leu Gly Gly Phe Ser Gly Ala Pro Leu Phe Asn Asp Lys Gly Glu Val
225                 230                 235                 240

Val Gly Ile His Gln His Gly Thr Asn Thr Pro Asn Ala Gln Glu Ser
                245                 250                 255

Glu Arg Ile Gly Gly Gly Thr Leu Phe Thr Glu Lys His Arg Ala Trp
            260                 265                 270

Ile Arg Ser Met Ile Asp Lys Tyr Gly Ile Lys Gly Trp Tyr Ile Asp
        275                 280                 285

Gly Ala Asn Arg Tyr Tyr Asp Glu Asn His Arg Ala Leu Lys Asp
    290                 295                 300

Val Glu Ser Glu Ile Asp Gly Ala Leu Tyr Arg Phe Asp Glu Lys Gly
305                 310                 315                 320

Arg Ala Thr Leu Leu Glu Gly Glu Glu Lys Gly Arg Val Leu Leu Arg
                325                 330                 335

Val Glu Asp Thr Lys Gly Thr Pro Leu Ile Ser Asp Lys Val Val Gln
            340                 345                 350

Glu Gly Ser Val Gly Ser Gly Leu Asn Phe His Leu Arg Gln Asn Pro

-continued

```
                355                 360                 365
Asn Phe Lys Gln Leu Ile Ala Thr Ser Pro Thr Ala Lys Val Val Ser
    370                 375                 380
Tyr Asn Gly Val Pro Ile Asn Lys Leu Ala Ser Asp Thr Ser Trp Ser
385                 390                 395                 400
Asp Glu Tyr Val Ser Lys Leu Ala Leu Gly Asp Thr Ile Ile Arg Ala
                405                 410                 415
Val Val Asp Ser Val Thr Pro Pro Ser Thr Ser Ser Ser Asp Phe Ala
                420                 425                 430
Arg Thr Glu Val Gly Lys Val Asp Leu Ser Gly Lys Ser Asn Leu Pro
            435                 440                 445
Val Pro Ser Lys Glu Val Leu Gln Ala Pro Asn Gly Ser Glu Asn Phe
        450                 455                 460
Tyr Ala Thr Thr His Ile Gln Thr Pro Asp Gly Ser Gly Ser Gly Thr
465                 470                 475                 480
Leu Ile Ala Pro Asn Leu Val Leu Thr Val Ala His Asn Phe Leu Thr
                485                 490                 495
Val Lys Gly Ser Glu Val Val Thr Lys Ser Gly Arg Thr Asn Thr Val
                500                 505                 510
Tyr Lys Ala Thr Leu Pro Ser Gly Gln Pro Val Asn Phe Ser Asp Asp
            515                 520                 525
Asp Ile Val Tyr Trp Asn Lys Lys Asp Ser Val Phe Gly Phe Lys Asn
545                 535                 540
Asp Leu Ala Leu Val Arg Leu Lys Glu Lys Leu Thr Ala Val Ser Pro
545                 550                 555                 560
Val Glu Val Val Ser Glu Ser Thr Ser Ile Thr Lys Gly Asp Lys Val
                565                 570                 575
Ser Val Tyr Gly Phe Pro Asp Gly Arg Leu Ser Pro Val Leu Asp Ser
            580                 585                 590
Glu Val Val Ala Thr Thr Asp Phe Gly Ser Gly Ile Glu Gly Ile Ser
        595                 600                 605
Tyr Gly Gly Thr Lys Pro Gly Ala Ser Gly Gly Leu Tyr Asn Asp
    610                 615                 620
Lys Gly Ser Leu Ile Gly Val His Gln Asn Gly Val Val Gly Ser Arg
625                 630                 635                 640
Ser Gly Gly Leu Val Leu Ser Lys Glu Gln Leu Asp Trp Val Arg Ser
                645                 650                 655
Tyr Ile Glu Gly Lys Pro Lys Ala Pro Val Tyr Val Thr Asp Asn Ile
            660                 665                 670
Leu Val Asp Glu Lys Asp Lys Asp Lys Leu Pro Ser Thr Ser Lys Glu
        675                 680                 685
Glu Lys Pro Thr Thr Pro Lys Val Glu Ser Asp Lys Asp Lys Pro Asn
    690                 695                 700
Thr Pro Leu Lys Pro Gln Glu Lys Pro Lys Thr Glu Val Ile Thr Ser
705                 710                 715                 720
Tyr Glu Gly Asp Ser Thr Leu Glu Val Gly Lys Glu Arg Thr Glu Glu
                725                 730                 735
Thr Glu Gly Glu Lys Glu Gly Val Ser Leu Ile Tyr Arg Thr Val Tyr
            740                 745                 750
Lys Gly Thr Lys Ser Lys Thr Glu Met Ser Pro Ile Ala Phe Asp Thr
        755                 760                 765
Val Tyr Gln Gly Asp Glu Thr Lys Glu Leu Gly Phe Arg Ser Val Leu
    770                 775                 780
```

Glu Gly Lys Glu Gly Leu Val Thr Arg Thr Thr Ser Tyr Gln Val Asp
785                 790                 795                 800

Lys Tyr Thr Gly Ala Val Ser Ser Lys Ile Ser Glu Lys Ile Ala
            805                 810                 815

Pro Gln Ser Gln Val Ile Thr Leu Gly Ile Lys Lys Asn Ser Ser Thr
            820                 825                 830

Lys Glu Val Pro Ile Thr Glu Arg Phe Glu Asp Ser Ala Glu Leu Glu
            835                 840                 845

Lys Gly Lys Thr Glu Val Ile Ser Glu Gly Ser Val Gly Lys Glu Val
            850                 855                 860

Thr Thr Val Thr Tyr Lys Val Leu Pro Asp Gly Lys Val Ile Glu Asn
865                 870                 875                 880

Ser Arg Thr Val Asp Val Thr Pro Met Arg Glu Arg Val Val Arg Lys
                885                 890                 895

Gly Val Lys Glu Val Val Ser Pro Asp Lys Val Glu Ser Leu Val Pro
                900                 905                 910

Lys Asp Ala Pro Ile Arg Glu Glu Gln Pro Ala Leu Ser Glu Gly Phe
            915                 920                 925

Ser Glu Ser Asp Ala Leu Val Ser Gly Glu Lys Ile Gln Gly Asp Leu
            930                 935                 940

Gly Ile Leu Ile Val Ser Ser Glu Glu Leu Val Pro Glu Arg Val Glu
945                 950                 955                 960

Val Pro Asp Phe Val Thr Lys Val Thr Gly Gly Lys Leu Thr Val
                965                 970                 975

Glu Gly His Arg Asn Glu Ser Lys Ile Lys Thr Pro Ser Lys Gln Glu
            980                 985                 990

Arg Ser Ser Arg Pro Glu Thr Thr Ala Gln Phe Thr Thr Asn Gly Thr
            995                 1000                1005

Gly Ser Ser Ser Leu Thr Ala Val Phe Gly Gly Lys Thr Asp Lys Ile
        1010                1015                1020

Leu Leu Ser Thr Val Glu His Ser Val Ile Lys His Asn Gln Gln Arg
1025                1030                1035                1040

Gly Trp His Lys Ile Asn Asn Gln Trp Tyr Phe Arg Asn Ser Asp Gly
            1045                1050                1055

Lys Glu Arg Thr Gly Trp Met Lys Glu Asn Asp Ala Trp Tyr Tyr Phe
            1060                1065                1070

Asp Thr Asn Gly Thr Met Gln Thr Gly Trp Leu Glu Asp Thr Asp Gly
        1075                1080                1085

Asn Trp Tyr Tyr Leu Asn Asp Asn Gly Arg Met Glu Ile Gly Trp Phe
        1090                1095                1100

Gln Asp Ser Ser Gly Ala Trp Tyr Tyr Leu Gly Ser Ser Gly Arg Met
1105                1110                1115                1120

Glu Ser Asn Thr Trp Ile Tyr Tyr Lys Gly Lys Trp Tyr Tyr Ile Asp
            1125                1130                1135

Ala Leu Gly Lys Leu Leu Phe Asn Ser Val Thr Pro Asp Gly Tyr Arg
            1140                1145                1150

Val Asn Glu Tyr Gly Glu Trp Ile Asn
        1155                1160

<210> SEQ ID NO 6
<211> LENGTH: 960
<212> TYPE: PRT
<213> ORGANISM: Streptococcus pneumonia

<400> SEQUENCE: 6

```
Met Glu Lys Val Lys Gly Leu Gln Asn Ala Thr Val His Val Glu Phe
1               5                   10                  15

Lys Pro Ala Ala Asp Gly Pro Ser Phe Tyr Asn Leu Phe Ser Ala Ser
            20                  25                  30

Ser Thr Thr Lys Val Asn Glu Tyr Phe Thr Met Ala Ile Asn Asn Gly
        35                  40                  45

Thr Ala Leu Ile Glu Gly Arg Gly Ala Asp Gly Ser Gln Phe Tyr Gly
    50                  55                  60

Ser Tyr Thr Asp Ala Pro Leu Lys Ile Arg Pro Gly Lys Tyr Asn Ser
65                  70                  75                  80

Val Thr Phe Thr Val Glu Arg Pro Lys Asp Ser Pro Asn Gly Gln
                85                  90                  95

Val Arg Leu Tyr Val Asn Gly Val Leu Ser Arg Thr Asn Lys Lys Ser
                100                 105                 110

Gly Lys Phe Leu Ala Asp Met Pro Asp Val Asp Lys Leu Gln Leu Gly
            115                 120                 125

Ala Thr Asn Arg Ala Gly Glu Leu Lys Trp Gly Ser Asp Leu Ser Ile
    130                 135                 140

Arg Asn Leu Thr Val Tyr Asn Arg Ala Leu Thr Pro Glu Glu Val Lys
145                 150                 155                 160

Lys Arg Ser Gln Leu Phe Asp Val Ile Asp Ile Glu Pro Leu Leu Ala
                165                 170                 175

Glu Gly Ala Val Leu Thr Glu Lys Gln Glu Leu Phe Met Ser Gly Val
            180                 185                 190

Asn Gly Lys Pro Asn Ser Glu Gly Ile Lys Ser Tyr Arg Ile Pro Pro
        195                 200                 205

Leu Leu Arg Thr Asp Lys Gly Thr Leu Leu Ala Gly Ala Asp Gln Arg
    210                 215                 220

Arg Leu His His Ser Asp Trp Gly Asp Ile Ala Met Val Val Arg Arg
225                 230                 235                 240

Ser Glu Asp Gly Gly Thr Thr Trp Gln Pro Thr Leu Thr Leu Thr Asn
                245                 250                 255

Leu Arg Asp Asn Pro Glu Ala Lys Asp Pro Gln Ala Ser Ser Ser Leu
            260                 265                 270

Asn Ile Asp Met Val Leu Val Gln Asp Pro Thr Thr Lys Arg Ile Phe
        275                 280                 285

Ser Ile Tyr Asp Met Phe Pro Glu Gly Arg Ala Val Phe Gly Met Pro
    290                 295                 300

Asn Lys Pro Gln Lys Ala Tyr Gln Gln Val Gly Asp Lys His Tyr Gln
305                 310                 315                 320

Leu Leu Tyr Lys Gln Gly Glu Asn Gln Ala Tyr Thr Val Arg Glu Asn
                325                 330                 335

Gly Glu Val Tyr Asp Ala Asn Asn Gln Lys Thr Asp Tyr Arg Val Val
            340                 345                 350

Val Asp Pro Lys Glu Glu Ala Tyr Arg Asp Lys Gly Asp Leu Tyr Lys
        355                 360                 365

Arg Glu Glu Leu Leu Gly Asn Ile Tyr Phe Ala Gln Ser Ala Lys Thr
    370                 375                 380

Pro Phe Arg Val Ala Tyr Thr Ser Tyr Leu Trp Leu Ser Tyr Ser Asp
385                 390                 395                 400

Asp Asp Gly Lys Thr Trp Ser Gln Pro Arg Asp Ile Thr Pro Ser Ile
                405                 410                 415
```

```
Arg Gln Asp Trp Met Lys Phe Leu Gly Thr Gly Pro Gly Thr Gly Ile
                420                 425                 430

Val Leu Arg Thr Gly Glu His Lys Gly Arg Ile Leu Val Pro Thr Tyr
            435                 440                 445

Thr Thr Asn Ala Ile Ser His Leu Ser Gly Ser Gln Ser Ser Arg Leu
        450                 455                 460

Ile Tyr Ser Asp Asp His Gly Glu Thr Trp Gln Ala Gly Ala Ala Val
465                 470                 475                 480

Asn Asp Asp Arg Thr Val Gly Arg Arg Lys Ile His Ser Ser Thr Met
                485                 490                 495

Asn Asn Arg Asn Thr Gln Asn Thr Glu Ser Val Ala Val Gln Leu Asn
                500                 505                 510

Asn Gly Asp Val Lys Leu Phe Met Arg Gly Leu Thr Gly Asp Leu Gln
            515                 520                 525

Val Ala Thr Ser Lys Asp Asp Gly Gln Thr Trp Asp Lys Glu Ile Lys
        530                 535                 540

Arg Tyr Asn Gln Val Lys Asp Val Tyr Val Gln Met Ala Ala Ile His
545                 550                 555                 560

Thr Met His Glu Gly Lys Glu Tyr Ile Ile Leu Thr Asn Ser Gly Gly
                565                 570                 575

Leu Lys Arg Thr Asn Gly Met Ala His Leu Ala Arg Val Glu Asp Asn
            580                 585                 590

Gly Asp Leu Thr Trp Leu His His Arg Pro Ile Gln Lys Gly Glu Phe
        595                 600                 605

Ala Tyr Asn Ser Leu Gln Glu Leu Gly Asn Gly Glu Tyr Gly Ile Leu
        610                 615                 620

Tyr Glu His Thr Glu Lys Gly Gln Asn Asp Tyr Thr Leu Ser Phe Arg
625                 630                 635                 640

Lys Phe Asn Trp Asp Phe Leu Thr Lys Asp Pro Val Tyr Pro Thr Ser
                645                 650                 655

Val Thr Ile Arg Asp Val Arg Lys Leu Glu Thr Glu Glu Asp Ala
                660                 665                 670

Glu Gln Gly Ile Leu Ala Met Gln Phe Asp Ser Glu Val Leu Val Asn
            675                 680                 685

Ala Ile Pro Thr Leu Thr Leu Ala Asn Gly His Lys Ala Thr Phe Leu
        690                 695                 700

Thr Gln Ala Asp Gln Lys Thr Leu Leu Phe Thr Phe Asn Lys Glu Asp
705                 710                 715                 720

Ala Gly Gln Glu Ile Thr Gly Leu Met Ala Gly Arg Ile Asp Ser Met
                725                 730                 735

His Asp Leu Pro Val Thr Leu Ala Gly Ser Arg Ile Pro Glu Asp Ala
            740                 745                 750

Lys Glu Asn Pro Val Glu Thr Met Asn Thr Val Arg Glu Asn Val Ser
        755                 760                 765

Glu Glu Met Thr Glu Arg Lys Ser Glu Lys Asp Lys Leu Ser Leu Glu
        770                 775                 780

Ser Ser Asp Arg Met Val Ala Asn Ser His Leu Thr Ser Phe Ala Pro
785                 790                 795                 800

Arg Tyr Leu Gln Ser Tyr Val Gly Asp Val Ile Lys Thr Glu Thr Lys
                805                 810                 815

Val Pro Ile Thr Thr Gly Trp Lys Gln Glu Asn Gly Ala Trp Tyr Phe
            820                 825                 830
```

```
Tyr Thr Ser Ala Gly Glu Val Val Lys Gly Trp His Gln Glu Ala Asp
            835                 840                 845

Lys Trp Tyr Tyr Leu Ser Ser Thr Gly Ala Met Ala Thr Gly Trp Val
850                 855                 860

Arg Asp Gly Asn Gln Trp Tyr Tyr Leu Ser Glu Ser Gly Ala Met Ser
865                 870                 875                 880

Thr Gly Trp Val Glu Ser Ser Gly Val Trp Tyr Tyr Leu His Ser Asn
                885                 890                 895

Gly Ser Met Ala Thr Gly Trp Ile Lys Asp Gly Asp His Trp Tyr Tyr
            900                 905                 910

Gln Glu Ser Ser Gly Ala Met Arg Val Asn Gln Trp Phe Gln Val Gly
            915                 920                 925

Asp Lys Trp Tyr Tyr Val Asn Glu Ser Gly Arg Leu Ala Val Asn Thr
            930                 935                 940

Ile Val Asp Gly Tyr Gln Val Asn Ser Asn Gly Glu Trp Val Asn Tyr
945                 950                 955                 960

<210> SEQ ID NO 7
<211> LENGTH: 383
<212> TYPE: PRT
<213> ORGANISM: Streptococcus pneumonia

<400> SEQUENCE: 7

Met Lys Gln Phe Leu Glu Arg Ala Ser Ile Leu Ala Leu Ser Leu Val
1               5                   10                  15

Leu Ile Thr Ser Phe Ser Ile Ser Ser Ala Leu Pro Ala Met Phe Asp
            20                  25                  30

Tyr Tyr Gln Gly Tyr Ser Lys Glu Gln Ile Glu Leu Leu Val Ser Leu
        35                  40                  45

Pro Ser Phe Gly Ile Met Met Met Leu Leu Leu Asn Gly Phe Leu Glu
    50                  55                  60

Lys Ile Phe Pro Glu Arg Leu Gln Ile Ser Leu Gly Leu Leu Ile Leu
65                  70                  75                  80

Ser Leu Ser Gly Thr Ala Pro Phe Trp Tyr Gln Ala Tyr Pro Phe Val
                85                  90                  95

Phe Gly Thr Arg Leu Leu Phe Gly Leu Gly Leu Gly Met Ile Asn Ala
            100                 105                 110

Lys Ala Ile Ser Ile Ile Ser Glu Arg Tyr Gln Gly Lys Arg Arg Ile
        115                 120                 125

Gln Met Leu Gly Leu Arg Ala Ser Ala Glu Val Val Gly Ala Ser Leu
    130                 135                 140

Ile Thr Leu Ala Val Gly Gln Leu Leu Ala Phe Gly Trp Thr Ala Ile
145                 150                 155                 160

Phe Leu Ala Tyr Ser Ala Gly Phe Leu Val Leu Pro Leu Tyr Leu Leu
                165                 170                 175

Phe Val Pro Tyr Gly Lys Ser Lys Lys Glu Val Lys Lys Arg Ala Lys
            180                 185                 190

Glu Ala Ser Arg Leu Thr Arg Glu Met Lys Gly Leu Ile Phe Thr Leu
        195                 200                 205

Ala Ile Glu Ala Ala Val Val Val Cys Thr Asn Thr Ala Ile Thr Ile
    210                 215                 220

Arg Ile Pro Ser Leu Met Val Glu Arg Gly Leu Gly Asp Ala Gln Leu
225                 230                 235                 240

Ser Ser Phe Val Leu Ser Ile Met Gln Leu Ile Gly Ile Val Ala Gly
                245                 250                 255
```

```
Val Ser Phe Ser Phe Leu Ile Ser Ile Phe Lys Glu Lys Leu Leu Leu
            260                 265                 270

Trp Ser Gly Ile Thr Phe Gly Leu Gly Gln Ile Val Ile Ala Leu Ser
        275                 280                 285

Ser Ser Leu Trp Val Val Ala Gly Ser Val Leu Ala Gly Phe Ala
290                 295                 300

Tyr Ser Val Val Leu Thr Thr Val Phe Gln Leu Val Ser Glu Arg Ile
305                 310                 315                 320

Pro Ala Lys Leu Leu Asn Gln Ala Thr Ser Phe Ala Val Leu Gly Cys
                325                 330                 335

Ser Phe Gly Ala Phe Thr Thr Pro Phe Val Leu Gly Ala Ile Gly Leu
            340                 345                 350

Leu Thr His Asn Gly Met Leu Val Phe Ser Ile Leu Gly Gly Trp Leu
            355                 360                 365

Ile Val Ile Ser Ile Phe Val Met Tyr Leu Leu Gln Lys Arg Ala
        370                 375                 380

<210> SEQ ID NO 8
<211> LENGTH: 395
<212> TYPE: PRT
<213> ORGANISM: Streptococcus pneumonia

<400> SEQUENCE: 8

Met Lys Lys Ile Val Phe Ala Ser Ala Leu Ala Leu Thr Leu Ala Gly
1               5                   10                  15

Ala Val Leu Thr Asn Asp Val Phe Ala Asn Asp Arg Leu Val Ala Thr
            20                  25                  30

Gln Ser Thr Asp Gly Asn Val Leu Thr Ser Glu Val Leu Lys Pro Ser
        35                  40                  45

Ser Gly Asn Val Leu Val Gly Ile Lys Gly Glu Phe Leu Pro Pro His
    50                  55                  60

Gln Gln Ser Ile Leu Asp Ala Ile Asn Lys Ile Arg Lys Glu Ala Ala
65                  70                  75                  80

Asp Glu Gly Leu Val Asp Lys Tyr Val Pro Val Lys Trp Ser Val Asp
                85                  90                  95

His Glu Lys Thr Ala Phe Val Arg Ala Ala Glu Val Ser Val Thr Leu
            100                 105                 110

Lys Ala Glu Arg Leu Ser Ser Lys Asn Asn Trp Thr Ala Phe Pro Ser
        115                 120                 125

Gly Asn Ser Leu Ser Gly Glu Val Leu Asp Leu Asn Pro Asp Gly Phe
    130                 135                 140

Leu Lys Ala Ile Glu Asn Trp His Ala Glu Lys Ala Asn Tyr Val Ala
145                 150                 155                 160

Lys Lys Lys Asp Lys Thr Ser Lys Glu Phe Ser Phe Tyr Glu Asn
                165                 170                 175

Leu Ile Asn Pro Lys Phe Thr Tyr Val Gly Leu Ala Ala Phe Lys Asn
            180                 185                 190

Ala Ala Ser Pro Gln Lys Ala Ala Thr Val Ala Leu Ala Leu Gly Thr
        195                 200                 205

Thr Thr Ser Ser Glu Glu Leu Ala Gly Gly Tyr Gly Ser Ala Val Gln
    210                 215                 220

Tyr Thr Glu Val Thr Ala Ser Asn Leu Ser Thr Val Lys Ser Lys Ala
225                 230                 235                 240

Met Val Val Glu Thr Pro Leu Lys Asp Phe Arg Lys Ser Thr Ser Asp
```

```
                  245                 250                 255
Gln Ser Gly Trp Val Gln Ser Asn Gly Lys Trp Tyr Phe Tyr Glu Ser
            260                 265                 270

Gly Asp Val Lys Thr Gly Trp Leu Lys Thr Gly Gly Lys Trp Tyr Tyr
            275                 280                 285

Leu Asn Asp Leu Gly Val Met Gln Thr Gly Phe Val Glu Val Asp Gly
            290                 295                 300

Ser Val Tyr Tyr Leu Ser Asn Ser Gly Ala Met Phe Thr Gly Trp Gly
305                 310                 315                 320

Thr Asp Gly Ser Arg Trp Phe Tyr Cys Asp Gly Ser Val Ala Met Lys
                325                 330                 335

Thr Gly Trp Tyr Lys Glu Asn Gly Thr Trp Tyr Tyr Leu Asp Glu Glu
                340                 345                 350

Gly Ile Met Lys Thr Gly Trp Phe Lys Val Gly Gln His Trp Tyr Tyr
                355                 360                 365

Ala Asn Gly Ser Gly Ala Leu Ala Val Ser Thr Thr Thr Pro Asp Gly
            370                 375                 380

Tyr Arg Val Asn Ala Asn Gly Glu Trp Val Ser
385                 390                 395

<210> SEQ ID NO 9
<211> LENGTH: 615
<212> TYPE: PRT
<213> ORGANISM: Streptococcus pneumonia

<400> SEQUENCE: 9

Met Ser Lys Ser Asn His Glu Arg Arg Met Arg Tyr Ser Ile Arg Lys
1               5                   10                  15

Phe Ser Val Gly Val Ala Ser Val Leu Val Ala Ser Phe Phe Met Gly
            20                  25                  30

Ser Val Ala His Ala Ser Gly Leu Val Lys Asp Asp Ser Val Lys Thr
        35                  40                  45

Thr Glu Ile Ala Ala Thr Asn Arg Glu Lys Glu Asn Asp Ala Lys Ser
    50                  55                  60

Gly Trp Gly Gly Ile Ile Asp Gly Ser Gly Lys Leu Leu Gly Gly Phe
65                  70                  75                  80

Ser Glu Ile Lys Glu Lys Leu Glu Lys Glu Ile Asp Glu Ser Ser Leu
                85                  90                  95

Thr Ser Glu Gln Lys Lys Ser Tyr Lys Glu Lys Ile Val Lys Val Lys
            100                 105                 110

Gln Asn Asp Val Asp Gly Leu Phe Gly Val His Arg Glu Tyr Leu Asn
        115                 120                 125

Gln Leu Asp Phe Gln Tyr Leu Glu Leu Ser Lys Val Glu Glu Glu Phe
    130                 135                 140

Lys Tyr Gln Glu Glu Gln Ile Gln Arg Met Phe Glu Gln Lys Gly Ile
145                 150                 155                 160

Thr Asn Glu Asp Lys Asp Ala Met Leu Lys Lys Ile Ala Glu Ile His
                165                 170                 175

Gln Glu Ala Glu Lys Asp Ile Lys Ala Ser Gly Gly Tyr Arg Asp Lys
            180                 185                 190

Leu Asn Gly Thr Lys Val Lys Phe Leu Gln Asn Leu Asp Lys Leu Phe
        195                 200                 205

Thr Ser Thr Lys Ser Lys Phe Glu Lys Glu Met Gln Glu Leu Tyr Arg
    210                 215                 220
```

```
Lys Lys Glu Ala Glu Ile Val Lys Glu Lys His Leu Glu Lys Asp Lys
225                 230                 235                 240

Ile Tyr Asp Asp Ala Asp Val Gln Lys Leu Arg Glu Leu Glu Lys Asp
            245                 250                 255

Ala Leu Lys Lys Leu Asp Glu Ala Lys Thr Asn Asp Glu Ala Leu Arg
        260                 265                 270

Val Lys Leu Glu Phe Ala Arg Asn Val Glu Lys Asn Ser Gln Gln Val
    275                 280                 285

Gln Lys Ile Asp Asp Lys Leu Gln Glu Leu Ile Lys Glu Ala Lys Arg
290                 295                 300

Glu Leu Glu Lys Leu Asn Gln Gly Ile Ala Glu Val Asp Lys Leu Pro
305                 310                 315                 320

Glu Leu Pro Ala Asn Asp Ser Asp Tyr Met Val Gln Lys Lys Tyr Ile
            325                 330                 335

Trp Asp Glu Asp Lys Glu Thr Ile Pro Lys Lys Ile Ala Lys Phe Lys
            340                 345                 350

Glu Asn Leu Gly Asn Lys Thr Tyr Thr Lys Glu Ser Leu Gln Lys Phe
        355                 360                 365

Ile Asp Asp Cys Ile Tyr Tyr Gln Thr His Ala Lys Ile Glu Val Met
370                 375                 380

Thr Arg Lys Val Ala Gly Tyr Arg Lys Ala Tyr Pro Asn Asn Pro Glu
385                 390                 395                 400

Ile Glu Lys Glu Phe Val Ser His Ile Lys Gln Thr Ser Ser Leu Thr
            405                 410                 415

Tyr Ala Ser Leu Glu Asn Asp Ser Leu Lys Arg Tyr Phe Glu Lys Asp
        420                 425                 430

Phe Ala Pro Ala Phe Glu Arg Ile Lys Gln Ile Val Glu Gly Leu Glu
    435                 440                 445

Lys Pro His Thr Pro Ala Gln Pro Gly Ile Glu Asn Gln Lys Pro Ser
450                 455                 460

Ala Pro Lys Thr Glu Lys Ser Ala Glu Gln Pro Lys Ala Gly Trp Lys
465                 470                 475                 480

Gln Glu Asn Gly Met Trp Tyr Phe Tyr Asn Thr Asp Gly Ser Met Ala
            485                 490                 495

Thr Gly Trp Leu Gln Asn Asn Gly Ser Trp Tyr Tyr Leu Asn Ala Asn
        500                 505                 510

Gly Ala Met Ala Thr Gly Trp Leu Gln Asn Asn Gly Ser Trp Tyr Tyr
    515                 520                 525

Leu Asn Ala Asn Gly Ser Met Ala Thr Gly Trp Leu Gln Asn Asn Gly
530                 535                 540

Ser Trp Tyr Tyr Leu Asn Ala Asn Gly Ser Met Ala Thr Asp Trp Val
545                 550                 555                 560

Lys Asp Gly Asn Thr Trp Tyr Tyr Leu Glu Ala Ser Gly Ala Met Lys
            565                 570                 575

Ala Ser Gln Trp Phe Lys Val Ser Asp Lys Trp Tyr Tyr Val Asn Gly
        580                 585                 590

Leu Gly Ala Leu Val Val Asn Thr Thr Val Asp Gly Tyr Arg Val Asn
    595                 600                 605

Ala Asn Gly Glu Trp Val Ser
610                 615

<210> SEQ ID NO 10
<211> LENGTH: 758
<212> TYPE: PRT
```

<213> ORGANISM: Streptococcus pneumonia

<400> SEQUENCE: 10

```
Met Ser Lys Ser Asn His Glu Arg Arg Met Arg Tyr Ser Ile Arg Lys
1               5                   10                  15

Phe Ser Val Gly Val Ala Ser Val Ala Val Ala Ser Leu Phe Met Gly
            20                  25                  30

Ser Val Val His Ala Thr Glu Asn Val Ser Ala Asn Pro Pro Ile Pro
        35                  40                  45

Gln Ile Val Ser Pro Gly Asp Lys Lys Glu Tyr Glu Asp Ala Val Gln
    50                  55                  60

Arg Val Asn Lys Glu Ile Ser Asp Tyr Val Thr Ser Arg Leu Asp Ser
65                  70                  75                  80

Leu Asp Arg Ser Val Ser Gly Phe Ser Glu Ile Val Thr Lys Val Gln
                85                  90                  95

Val Val Val Asp Lys Tyr Arg Asp Lys Ile Asp Arg Val Ser Thr Lys
            100                 105                 110

Ser Met Val Glu Glu Leu Gly Arg Glu Val Lys Lys Val Asp Glu
            115                 120                 125

Glu Ile Lys Leu Phe Gln Asn Arg Ser Gly Ser Lys Ser Thr Pro Lys
    130                 135                 140

Gly Leu Ser Leu Asn Asp Gly Leu Gln Gly Gly Asp Pro Ser Val
145                 150                 155                 160

Gly Gln Gly Pro Gly Val Val Pro Gln Pro Gly Gln Ala Gly Gly
                165                 170                 175

Ser Met Val Val Pro Pro Val Thr Gln Thr Pro Pro Ser Thr Ser Pro
            180                 185                 190

Ser Pro Gly Gln Lys Ala Thr Glu Ala Glu Lys Lys Leu Gln Asp
            195                 200                 205

Leu Ile Arg Gln Gly Gln Glu Glu Leu Lys Lys Leu Glu Asp Tyr Leu
    210                 215                 220

Arg Glu Val Asn Asn Tyr Pro Glu Leu Pro Asp Asn Asp Pro Asp Tyr
225                 230                 235                 240

Lys Val Gln Lys Lys Asp Ile Trp Asp Asn Ser Lys Asp Thr Ala Pro
                245                 250                 255

Lys Lys Ile Gln Val Phe Lys Glu Gln Leu Glu Lys Gln Thr Tyr Thr
            260                 265                 270

Glu Lys Thr Leu Lys Asp Ala Val Ala Glu Phe Ile Tyr Tyr Gln Phe
            275                 280                 285

His Ala Gln Ile Glu Thr Met Thr Arg Lys Ile Ala Thr Tyr Arg Lys
    290                 295                 300

Lys His Pro Asn Val Ala Glu Val Glu Arg Leu Phe Ser Glu Lys Leu
305                 310                 315                 320

Lys Gln Thr Ala Asn Ser Thr Tyr Ala Thr Leu Glu Gly Glu Ala Leu
            325                 330                 335

Lys Thr Tyr Phe Glu Arg Asp Phe Leu Pro Val Phe Asn Lys Ile His
            340                 345                 350

Ser Ile Ile Glu Glu Leu Glu Lys Ser Ser Gln Gly Glu Leu Lys
    355                 360                 365

Lys Gln Asp Lys Val Ala Glu Ala Gln Lys Val Glu Glu Ala Glu
            370                 375                 380

Lys Lys Ala Lys Ala Gln Lys Glu Glu Asp Arg Arg Asn Tyr Pro Thr
385                 390                 395                 400
```

Asn Thr Ser Lys Thr Ile Glu Leu Glu Ile Ala Glu Ala Gln Val Glu
                405                 410                 415

Val Ala Lys Ala Glu Leu Glu Leu Ala Gln Ala Gln Ala Gln Thr Pro
        420                 425                 430

Gln Asp Thr Asp Lys Ile Asn Thr Ala Lys Ala Lys Val Glu Thr Ala
        435                 440                 445

Lys Ser Lys Val Lys Thr Leu Glu Lys Ile Lys Ser Asp Ser Gly Arg
    450                 455                 460

Ala Gln Ala Gly Asp Gln Lys Pro Ser Met Pro Ala Pro Asp Thr Lys
465                 470                 475                 480

Pro Asp Leu Gln Pro Gln Pro Glu Val Pro Ser Thr Ser Pro Glu Pro
                485                 490                 495

Lys Pro Ile Pro Gln Pro Asp Gly Lys Gln Pro Ser Thr Pro Lys Glu
            500                 505                 510

Pro Glu Asn Lys Lys Pro Ser Val Pro Thr Gln Glu Lys Pro Ile Pro
        515                 520                 525

Gln Pro Glu Lys Pro Lys Pro Glu Val Lys Pro Gln Pro Glu Thr Pro
    530                 535                 540

Lys Thr Ser Lys Ile Ile Thr Ala Ser Asp Gly Lys Thr Lys Val Thr
545                 550                 555                 560

Val Val Phe Asp Lys Ala Val Asp Ala Asp Lys Val Asn Ile Lys Glu
                565                 570                 575

Val Thr Thr Lys Glu Leu Ala Glu Lys Ile Ala Arg Gln Thr Gly Gly
            580                 585                 590

Gly Thr Val Arg Ile Phe Asp Leu Ser Leu Ser Lys Gly Gly Lys Glu
        595                 600                 605

Thr His Val Asn Gly Glu Arg Thr Val Arg Leu Ala Leu Gly Gln Thr
    610                 615                 620

Ala Ser Asp Val His Val Tyr His Val Lys Glu Asn Gly Asp Leu Glu
625                 630                 635                 640

Arg Ile Pro Ser Lys Val Glu Asn Gly Gln Val Val Phe Lys Thr Asn
                645                 650                 655

His Phe Ser Leu Phe Ala Ile Lys Thr Leu Ser Lys Asn Gln Asn Val
            660                 665                 670

Thr Thr Pro Lys Gln Ile Lys Pro Ser Val Gln His Gly Gln Thr Gln
        675                 680                 685

Ile Gly Glu Asn Gln Thr Gly Lys Phe Gln Asn Lys Glu Val Asn His
    690                 695                 700

Lys Pro Leu Ala Thr Gly Asn Glu Thr Met Ala Lys Glu Asn Pro Thr
705                 710                 715                 720

Ser Ala Thr Glu Lys Asn Leu Pro Ser Thr Gly Ala Ala Thr Asn Leu
                725                 730                 735

Val Leu Glu Ile Ile Gly Leu Leu Gly Leu Ala Gly Thr Ser Leu Ile
            740                 745                 750

Ala Met Lys Arg Arg Lys
        755

<210> SEQ ID NO 11
<211> LENGTH: 4941
<212> TYPE: DNA
<213> ORGANISM: Streptococcus pneumonia

<400> SEQUENCE: 11
ttgttgctac ttatcaaaag aaaagaagga cttttttatga ccaaacaatg tcatcatcac      60

```
tttttagtca atcaggaaca agcagaaaag catgtcttcc gtaaaagtaa gaagtatcgt    120
acgctgtgtt cggtagcact tggaactatg gtgacagctg ttgtcgcttg gggtggccaa    180
gtagcacaag ctgacgaagt gacaatgcca ccactagata agactgttca gttaacggaa    240
aataatgcga ccaatttacc agaagctcag ccagcaccag ttgctgaaca gactgatagc    300
cttttctcaa ctggccaatc agatgggact atcacagtaa cggttcctca tgatacggta    360
accaatgcca tcaatcaagc aaccgctgaa gggcttacta ccattcagga taaacctatg    420
gatttaggca acacgacttc tgctagtgag accagtaagc aattggatac cgctgaagcg    480
gatgctgcca acaagctgac ggacatcact cgggtgacaa atacctataa agctgacaaa    540
gtcgcttatg aacaagataa aactcgtgtc gaaaaaggaa atgctgcgtt ggttgctagt    600
cataaagaag ctactcaagc aggaaaggcc ttgaatagtt cagtagatac cacggcttca    660
gaagtgaaga ctcaggacaa gtctgcgaac gtgactatta caactcaaac cgttccgtca    720
ggagagggat caactgtttc aggttatcag gactacacat ctgcggtagc tgctattgat    780
aaacaaaaca aggctagtct tgcggactat atcacgaaaa acaagccgc agatgccatt     840 accgcaaaga acctagctgt tcaaaaggaa aatgaagcag gtcttgcgaa tgcaaaggca    900
gagaatgaag cgattactaa acgcaatcaa gcaggacaaa aagcgattga tgatgaaaat    960
aaagcaggtc aagctgctgt ggataccac aataagaacc aacaaaaatt ggtgacagac    1020
cgtgaagatg agattgctgc tattataaaa cgcaataagg agaaagaaga agctgctaag    1080
aaagaaaatg aagccattga tgcctacaat gccaagaaaa tgaaccgata caacgtgac    1140 ttagctgaca tctcaaaagg agaggaaggt tacatctcac aagctcttgc tcaggctctc    1200
aacttgaaca atggggaacc gcaagcccga cattcagctg acacgagaaa tcctaatcgc    1260
atcattgcta agggtgacgc catgcttggt gggtattcta aaatcctaga ttctactggt    1320
ttcttcgtct atgatacctt taaaactgga gaaaccctt cattcactta tcaaaacctt    1380
caaaatgcga gttttgatgg taaaaagatt accaaagttg cttatgacat cacaaaccta    1440
gtgtctccaa ctgggacgga ttctgtacaa ttagttgtgc ctaatgaccc aacagaaggc    1500
tttattgcct atcgtaatga tgggacaggg aattggcgaa ccgataaaat ggagtttcgt    1560
gtcaaagcca agtatttctt agaggatggc tcgcaagtca gctttaccaa ggaaaaacca    1620
ggtgtcttta cccattcctc acttaatcat aatgacattg gcttagagta tgtcaaagac    1680
acatcaggca gtttgtccc tatcaatggc tcaaccattc aagtgacaga tgaagaccta    1740
gcacgttcac tttcttcaaa ccgtgctagt gatttgaacc tcccagaaga atgggatacc    1800
tcttttagca agtatgctta caagggagcg attgtctcaa ccgtcacatc aggcaatacc    1860
tacaccgtga ctttggaca aggcgatatg ccccaaaatg caggactgac ctattggttt    1920
gccttaaaca ccttacctgt tgcacgaacc gtcaaacctt atagtccgaa accacatgtg    1980
accccaaaac tagacccagt cccagagccg attaaagtcg tgccaaaaac ctttacccca    2040 aagacccttta ccccagagcc acctgtgatc tttaaggaaa aaccactgga gaaagtgact    2100
caacctcgct tgactttgac aaaggtgacc tttgctaaag aacctaggtc tgaacctttg    2160
cctaaagcac cacaagtacc aacggttcat tatcacgact atcgtctgac aacgacccct    2220
gaaatcatga aaaagtggt caataccgac caagacaatc ttcatgacaa aactattgcc    2280
aaggattcga cagttattta tccttttaaca gttgacgttt tttcttcaaa tcgtgccaaa    2340
acaactaccc ttacgtttga agattacctt ccagcaggct atgcctttga taagaaaaaa    2400
acacaagcag aaaatgagaa ttatacgctt acctttgatg aagctaagaa ctttgtgacc    2460
```

```
ctgactgcca aagaagcctt gcttcaagag gtcaatcaag acctcactaa gtcttatcaa    2520
ctggtggctc ctaaacttta tggtagcctt caaaatgatg gggctaccta ttccaatagt    2580
tataagctcc tcatcaataa gggaacgtca aatgcctata cagtgacctc taacgtggtg    2640
accgttcgta cacctggtga tgggaaaatc actagccgta ttactcctca aaaacgcaat    2700
gagaatgaag acggtgtggt cattaacgat acggtggtgg ctttaggaac gactaaccat    2760
taccgtttga cgtgggattt agatcaatat aaaggtgata cctcttctaa agaaacgatt    2820
gctcgtggtt tcttctttgt ggatgattac ccagaagaag tcttggattt ggtggataaa    2880
ggaacaagta tcaccactct tgatggtaaa gctgtatcag ggattactgt taaggcctat    2940
gtgtcgctgt cagaagctcc taaagacctt caagataaac tcgctcatgc caagatttct    3000
cctaaaggag cttccaaat cttccagcct aacgacaatc aggctttcta tgaccagtac    3060
gttaaaacag gaacctcttt gaaccttctc accaaaatga ccgtcaaaga cagcctttat    3120
ggtcaaaacta agacttatcg aaacaaagcc taccaagttg attttgggaa tggctataaa    3180
acaaatgagg tgaccaatac ccttgtcagc cccacaccta agaaacaaaa ccttaataag    3240
gataaagtgg acatcaatgg aaaaccgatg gtagtgggtt cacaaaacta ctataccttg    3300
tcatgggatt tagaccaata ccgtggcatt aaagctgata agctcaaat cgcaaaaggc    3360
ttctactttg tggatgacta tcctgaagaa gctgtgctac cagatgacac agctattcaa    3420
ctaacgacat ctaacggcaa ggctgtcata ggtgttacgg taaaaaacta cacgagttta    3480
tcagaagtcc ctaaacccct acaagcagcc tttgagaaac gcaagattgc gcctaaagga    3540
gctttccaag tctttatggc agaagatcca caagcctttt atgattctta tgtgaccaaa    3600
ggccaaaaca ttaccatcgt tacaccgatg acagttcgtg aggagatgct taattcaggg    3660
aagtcttatg ataacgtggc ttaccaagta gactttgggc aagtctatga aaccaatacg    3720
gtgaccaatc acgtgccaaa ggtaaatcct cataagacca ataccaataa agagggagtg    3780
tctattgatg gcaaaaccgt tcttcctaat accgtaaatt actataagat tgttctggat    3840
tatagtcagt acaaggactt ggtagtgacg gaggataccc ttgccaaagg ttttttacatg    3900
gtagatgact atccagaaga agctctaaca ctaaatgcag acggtgttca agtgatggat    3960
aaggcgggaa atcttgtcaa agggatttct gtcaaagcct atgcttcgtt atcagaagcg    4020
cctcaagtgg tacaagaagc tatggccaaa cgccaactta caccaaaagg agccattcaa    4080
gttttaagtg ctgatgatcc aaaagttttt tacgagacct atgttaagac aggtcaaacc    4140
ttggtggtga cgcttccgat gaccattaag aatgagttga caaagactgg tggcaagtat    4200
gaaaacacgg cttatcagat tgactttggt ttggcttatg tgacagaaac agtggtcaat    4260
aatgtgccaa aactagaccc acaaaaagat gtggtgattg atttgtcaca aaaggagaac    4320
agtcttgatg gaaaagaggt tgccttgaat caggtcttta actaccgctt ggtgggagta    4380
cttattcctg gtaatcgtgc gacaccactc atcgaatacc gctttgacga tgattacgat    4440
gaaagccatg acgactataa tggtgtttac acggcttata ctgtggtaga tgtcactcta    4500
aaagatggga cggttttact aaaagggaca gaagtgacta agtacacgct acaacatgtc    4560
gacacgtcaa aaggaacggt taccatcagt tttgacaagg aattcctaga aaaactagca    4620
gaagaatccg agtttcaggc agatgtttac ttgcagatga acgaatcgc ttcaggtgaa    4680
gtagaaaata cggtactaca taccgtcaat ggctacacca tcagttcaaa cacggttaaa    4740
acaactactc ctgaaccaga gccaccaact ccgaatcaac caacaccacc ccaaccacct    4800
```

| | |
|---|---:|
| attccaacac aagaaccacc agttccagca agtgtcttac caaatacagg agagagtcaa | 4860 |
| tctcttttgg cgcttgtcgg tggaggcctt cttttaggct tagcctatgt ccttgctaaa | 4920 |
| cgcaaaatgg aggacaatta a | 4941 |

<210> SEQ ID NO 12
<211> LENGTH: 5502
<212> TYPE: DNA
<213> ORGANISM: Streptococcus pneumonia

<400> SEQUENCE: 12

| | |
|---|---:|
| atgcacaaag caagagaaac aaaaacatat ggatctattc ggaaatcaaa aatttatgga | 60 |
| acttgtggag tgatactagg tttagcagct ttaagcatga taagcccagt tatagcagat | 120 |
| gaacgaactg aaaataaggc tacaaatgcg ccttatgccc agacgagtcc aagcagtatt | 180 |
| tctactgaaa atcaaggaaa gagtgaagaa aaaacaggaa cgttagaagt ttctatttcc | 240 |
| cattccagtt tagatgaaac tattcgaaag gcacaagaag ctggattgaa ggtggaattt | 300 |
| gattctgtag tagataaagg aactgcaagt acagcctctg agttgaaaaa aaagcaaaag | 360 |
| gaagtcgaga gtgattattg cacacaagca gatagtattg agaaagctac tgaaaaatat | 420 |
| cgtgaagatc aaagacaaaa tcaaacgaac cgaaagaaaa tccaagatga aaatactgcg | 480 |
| aagaaggaac aatatcaaaa ggatttaact tcttatcaag ctgaagtgaa tcgaattaat | 540 |
| cagaagaatg ctagtattcg tgcagagaat gaaaaaaatc aacgagagaa tcaggcagaa | 600 |
| atagatcgta tcaatcaaga gaatgcagaa atccgaaaac gaaatgaagc taagagagga | 660 |
| gcttatgaaa gctctttgac agactataca aagaagctag caactattaa agctgagcga | 720 |
| gatgcaattc aaacaagtaa gcctttattt ggatctgaaa caggtttcaa agtttatgga | 780 |
| ggatataatt cagctggtcg gggaagctta gactattata tgattttac agtagtacca | 840 |
| gatgataatc taccagtaga gagtatgcgt ggtttttag gttatcatgc agatacttat | 900 |
| gtaacaggag gcgcaggaac tcgagttagt aaggatagta cggaaactta tgatatcatt | 960 |
| aaatctccaa catttggaga tacattttat attcataaca ttggaacgtt gacagatggt | 1020 |
| agaaagatca tggcaaaagt catggttttcg gatttaggag actatcaggg agaagttcga | 1080 |
| aatggtgttc ctgtgacaga ttcagatatc tacctcaagg gtggagatgg tggaagtttc | 1140 |
| tactttgtct ataataatca tacccgtttg gaaatggttt ttgattttta tattgaaggt | 1200 |
| acgacaactc ctgtttccct cttaattgga acagttatta ccgatgtaga ttggggtcaa | 1260 |
| ggttcaaatt tgagttatgg ctcatctggt cgtggaatgg ttcttaatcc aagtggttca | 1320 |
| ggtttggatt ttgatggtcg cgttatgaag ggagtagaaa atggagttaa tgatacctca | 1380 |
| gatattccta aggcttcctt tgcttcagta gggtatggtt ctagtttaac gtaccttcac | 1440 |
| acatcatctc ctggttcgac agagggaaga actcccgctg aatgggatgc agagaatttg | 1500 |
| agtggaaatg ctcaaaacgt tgtcttcaca attcttgggg aggggcgga gttgaaaagc | 1560 |
| attccaccag taaatccacc tcgcaaacca acttatgaag ttgaaactac tccacccaat | 1620 |
| tctccaactg aaaacctga gaggtactc ccacccaaac ctgaggagat aaaggaaaaa | 1680 |
| gagatcccct ctttagtatc ccctccaaca gtaaggggtta gatatgcacg cttacaggca | 1740 |
| atgcctgacc tagaaaagtt tgtaaaaaat tcttctggtg aatctattga taaaagctat | 1800 |
| gtacctaaac tttcaacagt acagtgggaa ctaacaacta gcctcttcc agctaatcgt | 1860 |
| gaagctatta cagactttga aattgtggat gccttgcctt caggttttgt gttagatgtt | 1920 |
| gaagcttcca aaaaaattag ctcagatttt gaattaactt atgacgagtc gagccatgtt | 1980 |

```
gttcggatga aaggcttaga aagtttaaaa tctaagctta atcaagattt aagtaaggaa    2040
gtacaagtac cagctccaat tttagttggt aaagtaacga atgatggagc gacctacaag    2100
aataacttcc aattaaagat taacaataag tacgaaagtt attcaaacat tgttcagatt    2160
tcaacacctg gtaaaccgaa tgatccggac aatccgaata taatttcat tcaacctctt     2220 aaacataatt acaataagga taaagttatc attgatggta aatcagttct agttggttcg    2280
acaaattact accatattac cttggattat gatcaatata aggggatgaa ggcagattca    2340
tctactattt taaaaggatt cggagcaatt gatgattacc cagaagaggc tgttacgatt    2400
aatcaatcgg acattcgtta tattgacagc gaaggaaaag aagttgctgg tatctcggtg    2460
tatcagtatg attctataga tgccgttgat aatgataagg ttaaagcttt tcttgctagt    2520
tctgaaatta gcccaagggg tgctttccaa gtattttag tggatgatcc agaagcttat     2580
tttaaccagt atattaaatc aggaaaatcg gttacaatta ttgatccaat ggtaactaag    2640
gaagaactgc gaaatacagg aaaatcattt gagaatacgg cttaccaagt tgattttggt    2700
aacggatatc aaactgatac agttgtcaat aatgttccta ctgttaaacc aaccaaaaag    2760
aatttgaaca aagcaggtgt gaacatcgat gggaaacagg tcttggcagg ctttgtcaac    2820
tactacaagg taacggcaga ttatagtcaa tacaagggca ttgaagcgga taaagaccgt    2880
attggcaaag ggttctatat cgttgatgat tatccagaag aagctgttac catcaatcaa    2940
gacggtgttc aagtgacgga ttctaaaggg caagtggtca aaggtttgaa aatggctctt    3000
tatgatagtc tggataaggc accatcaggt gtacaagaat ccttggagtc tagccatttc    3060
actccgaaag gagcgattca agtattcgag gcagagaatc cagaggagtt ctacaagact    3120
tatgtgcaag ctggagaagt tctgaccatt accaatccaa tgactgttaa gaaggaattg    3180
ggtcaaacag gtggtaagta tgagaataca gcttatcaat tagactttgg tagtggctac    3240
cagacggata aggtagagaa caatgttcct actgcgaaac ctaccaagaa aaatctgaat    3300
aaagcaggcg tgaacatcga tgggaaacaa gtcttggcag gctctgtcaa ctactacaag    3360
gtaacggcag attatagcca atacagggc attgaagcgg ataaagaccg tattggcaaa    3420
gggttctata tcgttgacga ttaccagaa gaagctgtta ccatcaatca agatggtgtt     3480
caagtaacgg attctaaagg tcaagtagtt aaaggtttga aaatggctct ttatgatagt    3540
ctggataagg caccatcagg tgtccaaaaa gccctgaagt ctagtaattt cactccgaaa    3600
ggagcgattc aagtattcga ggcagagaat ccagaggagt tctacaagac ctacgtgcaa    3660
gctggagaaa ttctgaccat taccaaccca atgactgtta agaaggaatt gggtcaaaca    3720
ggtggtaagt atgagaatac agcttaccaa gttgatttcg gtaacggtta tcaaactgat    3780
acagttgtaa ataacgttcc tactgttaaa ccaaccaaga gaatttgaa caaggcaggc     3840 gtgaacatcg atgggaaaca agtcttggca ggctctgtca actactacaa ggtaacggca    3900
gattatagcc aatacagggg cattgaagcg gataaagacc gtattggcaa agggttctat    3960
atcgttgatg attacccaga agaagctgtt accatcaatc aagatggtgt tcaagtgacg    4020
gattctaaag gcaagtggt caaaggtttg aaaatggctc tttatgatag tctggataag     4080
gcaccatcag gtgtccaaaa agccctgaag tctagtaatt tcactccgaa aggagcgatt    4140
caagtattcg aggcagagaa tccagaggag ttctacaaga cttatgtgca agctggagaa    4200
attctgacca ttaccaaccc aatgactgtt aagaaggaat tgggtcaaac aggtggtaag    4260
tatgagaata cagcttacca aattgatttt ggttcagctt atatcacgga aacagtcgta    4320
```

| | |
|---|---|
| aacaatgttc ctactgcgaa accaactaag aagaatctga acaaagcagg tgtgaacatc | 4380 |
| gatgggaaac aagtcttggc aggctctatc aactactaca aggtaacggc agattatagt | 4440 |
| caatacaagg gcattgaagc ggataaagac cgtattggca aagggttcta tatcgttgat | 4500 |
| gattacccag aagaagctgt taccatcaat caagatggtg ttcaagtgac ggattctaaa | 4560 |
| gggcaagtgg tcaaaggttt gaaaatggct ctttatgata gtctggataa ggcaccatca | 4620 |
| ggtgtacaag aatccttgaa gtctagccat ttcactccga aaggagcgat tcaagtattc | 4680 |
| gaggcagaga atccagagga gttctacaag acttatgtgc aagctggaga agttctgacc | 4740 |
| attaccaacc caatgactgt taagaaggaa ttgggtcaaa caggtggtaa gtatgagaat | 4800 |
| acagcttatc aagttgattt tgggatggcc tatgtaactg aaacagcagt caataatgtt | 4860 |
| ccaaagattg aaccgaagaa agatgtagtg atcgaccatc taagtaaaga aagtttggat | 4920 |
| ggaaagagg tcaagatgaa tcaaacattt aattacaaat tagttggttc cttagtgcca | 4980 |
| aaagatcgct cagaacagtt gtttgagtat aaatttagcg atgattacga tgaaacacat | 5040 |
| gatgagtatc aaggtgtata tcaagtgttt gcgactgtag attttgaaac aagtgatggt | 5100 |
| caaaaattca agctggtga tgaattaact aagttcacaa gtcaagtagt agacaaggct | 5160 |
| aaaggtaaag tagatattag ctttgatggt gctttcttaa agtcgatttt agaaacatca | 5220 |
| gagtttcaag cagaagtata tctacaaatg acacgcattc agtcaggagc agtagaaaac | 5280 |
| acttactatc atacagttaa cggtgtggaa gttgtttcca atacggttgt gactcagact | 5340 |
| ccagaagagc caaaaactcc tgaagaacat ccgcaacaac agaacgaag cctgccatct | 5400 |
| acaggtgagc aggcttctgc agaattgctg ttagctggtc tgacaatggg aagccttgct | 5460 |
| acaggattgc tctacagcaa gcgcaagaaa aaagaggctt ag | 5502 |

<210> SEQ ID NO 13
<211> LENGTH: 1935
<212> TYPE: DNA
<213> ORGANISM: Streptococcus pneumonia

<400> SEQUENCE: 13

| | |
|---|---|
| atgaaattga gaacaaccat cttggcaaca actgctagcg taacgttgct tgggttagga | 60 |
| aatagtcaac ctgtgtatgc aaatagtaca acgagtagtc aagtagagag cttaaaaagt | 120 |
| gaatttatta agcaaagag agaatatgaa caagctaaaa gtatctatga caatgcttta | 180 |
| tcatcttcac ctagcaatac gattatactg agtgataagt atataaaggc tttgaagacg | 240 |
| gcttttctg attttaatat tagccagact gaacgtgaca gtgcgaaatc tattttgcag | 300 |
| tcagaaagtt tgagattaaa gaatcaaaat agtttccaca aagatgttgc tgatgaggga | 360 |
| gaacgtctgg atgtcaacaa tctaccgcta gctgttcgtc aggagttgtc attttttgcc | 420 |
| caagatttaa ttaaccaagt tcgttctcag gttgggacac ctagagtcag tgtttcaatt | 480 |
| tcggcacttg actttgcaga taaggtggcg aaagcatatg ttcaagataa ctggggttgg | 540 |
| cataaaatga gcgtatctgg tacacttggt catgatgcga ctggaatcaa tcatgtggcg | 600 |
| agagaatatg gactgcctac aaccaattct gaagaagaga aaaaggggga gcaaaactat | 660 |
| gaaaatctag cttctcgtct acctggtttc aaaacagcta acaaggctca gttaaaagag | 720 |
| gctatctata ttgggatgat agagtttatg ttcaatgata ctgagtggat gcatgctcag | 780 |
| agtattgctg gcttgaactg ggaaatgtg aactcaaaag attattttgg gctttcattc | 840 |
| tctagtcgtt cttctgttag ttcagcccat tttatcacgg tttcccaaga agatatcaag | 900 |
| cgtgcaagca aatcaagctt tagcacggct gctgtgagtg atccaactag tgtcaatcgc | 960 |

```
cgtcaagcaa tcaaaaagct agaggaagac tacaaagcca aggaaaaaat ttatcaagat    1020
tttcaaaaac aagcagatag taaaggatct caagggcagt ctaaccaagg ttcagctact    1080
gtgacagaac caagtaaacc aagcgctggc tcagctgagc ctactaaatc gattgaaaac    1140
acatctgatt tgcgtgacca atggaaacaa gagggaagtt attggtatta ttttgatcgt    1200
gcagggaaag ctcttgttaa tagttggaag ggaaactatt atctcaaatc aaatggtgtg    1260
atggcacgta atgaatgggt ttatgataca aactataaag cttggtatta tctcaaatca    1320
gatggaagct atgcacaaaa tagttggcaa ggaagttact accttaagtc agatggaaaa    1380
atggcacaaa gtgagtggct atacgattcc agctataaag cttggtatta tctcaagtca    1440
gatggaagct atgcacaaaa tagctggcaa ggaagctact accttaagtc agatgggaaa    1500
atggcacaaa gtgagtggct atacgattcc agctataaag cttggtatta tctcaagtca    1560
gatggaagct atgcacaaaa tagctggcaa ggaagttact accttaagtc agatggaaaa    1620
atggcacaaa gtgagtggct atacgattcc agctataaag cttggtacta tctcaaatca    1680
gatggaagct atgcacaaaa tagttggcaa ggaagttact accttaagtc agatggaaaa    1740
atggcacaaa gtgagtggct atatgattcc agttataaag cttggtacta tctcaaatca    1800
gatggaagtt atctgagaga tcaatggttc aaggacggaa gtgcttggta ttatttgaaa    1860
gcagatggta agatggcaca aaatgagacg attggtgctt attatttaga ttattctggt    1920
aagtggattt cttaa                                                    1935

<210> SEQ ID NO 14
<211> LENGTH: 4572
<212> TYPE: DNA
<213> ORGANISM: Streptococcus pneumonia

<400> SEQUENCE: 14
atgaaagaat tcaatttga gcgaaagcag cgttttttctt tgaggaaata tgcaatagga     60
gcttgttcgg tcttgctagg aacgagttta ttttttgctg gtatggatgc tcagcctgta    120
caggctaccg aaacgagttc aacactaatt tcaagtcatt atttggatga gcaggattta    180
tctgaaaagc tgaaatctga gttgcaatgg tttgaagaaa ataagattga ggtaaaagag    240
ggaaaagaat actactttgt ctatcgaaaa ttggctacaa gattaccaga aacaggtctt    300
ttttctaatg atgggacgtt tatcctggga gcaggattat tattgctttc cttcactta    360 atcaagagaa aaggggagc gtcttacttc cttgtgacag tctttgctgt tggtggatgg    420
ggagcatcca tctctgcttt cgaaaatctg gtagaattgc aaccagccct tgttaagaga    480
gtagaaggtc agttttttacc aagtcctgaa agagttcaag gatatgaatt tacgggatat    540
tatttggtaa gagatagtgg taacaaggaa ctttctgtcg ataaggtaga gtcgccagca    600
ttatctcaaa aggaggacag ttcagagcct caatctaaga gattgtacc acagactgca    660 tcttatttca gctcgactga agaccttgtg caatctcctc aaccatctta cgcagttgag    720
aaaattgttg aagctcctga tgaaatggtg cctatagga ctaaggaaga agttgcagga    780
aatccccaag tagaacaacc gaaagcaaaa gataatagtg atcataaaac aagtcctgag    840
gaaggtgtgt taaatgtcac agtagagaaa ccagaattgt taatcactac agaggaggtt    900 gcttccaaa cgatagaaca agaagatgca accttagcta aagggcaaac taaagttgtt    960
caaaaaggtg ttgttggtga acgcaccatc tatacgaag tcactgtcgt taatggggaa   1020
aagtctagca aagttataga aaatataatc acaaaagaac cagtgaacaa ggtgattgca   1080
```

-continued

```
gttgggacta aggaagaagt tgcaccaaaa ccaacacaac ctgtaactcc agagccagag    1140
gaagttaaac cagttcaacc tgaaaaaact ccaatagtag agaatgaaac agagacaaaa    1200
ccagttgatg gaataggaca accaacacca ggagcagaag aaacgccggg tacagaagcg    1260
acatcgggcg agaaacaaac acctgataaa cccgaagccg agccgaagca accagaacga    1320
gaagaagatc aatcccctgt gggacaaaag gttgaggaga accagctgga gaactcagtt    1380 gaggggggcaa aagatgctgg tgaaactgcc ccacaagaac cccaaaaaca accagaacaa    1440
acggctccat ctccagaggt caacccaagt caaggaaatg aaccagctcc agctgttcag    1500 cctgaccect tagctcccca agagcagtca gattcacaag tgcaaccaac tgtcccgagt    1560
ccagtaacta agaaaaagt actggactat aaaacaatct atacagcatc gccagcttta    1620
aattaccaag agcaacaagt agaagtagca ggcgaaaatg gtaaggaagt gataactact    1680
tcttacagtt ttgatgaaag tactgggaaa atagtagaaa acacttcgac aaaaatagag    1740
aaacaaccgg tggatagaat tgttaaggtt gggaatgtag aagaaacaag atcaacagtc    1800
aaaagacgtg aacagtttgt cgcggatgag tcacttgata aggtgtcaa agaagtcaga    1860 aatcaaggtc aggacgaaga aacaaccact attcgtgttt ataaagtaaa tgaacaaaca    1920
ggatctatct cagaagaaac tacaatgaaa aacactccag ctaaagataa agtaataaaa    1980
gtaggaaacg tagaaaagct agtgtcacct atagaaatca ctgaattgaa gaaagaagat    2040
tcaacacttc caaaggtaa agaaaaagtt gaagatgcag gtgagcaagg ggaaacaacc    2100
gtcactaaaa cttatgaagt taatccggag acaggagagt taacaaatcc agtagagaaa    2160
actgaaacaa ctaaagctat gcgccaaaaa gtaatcttgg ttggtactaa agaagagaaa    2220
cctcatttac tcccagttaa tagcgaatta gaaaatgcag taaacgtaac ggaagctact    2280
gcggagatga gaaatgtaga cttgttgaca aatgaaaagt taaagcgca gttagctcca    2340 tcagatatag aaataaatcg agatttattc ttaaaacgaa agaattaca aaaaactaat    2400 ccgcagataa gggatgatga agtaagagaa attctacgaa aagagtatct tgaaaaatta    2460
tcgattaaag aaacactcga tgcgactaaa accgatttag aagttagttt gaaaaaagtt    2520
gcggcgcata ccttgagtat tttaggtgac aatcaacaaa atagagaaaa agtaaaaggt    2580
gatattgaag ctaataaaga aaaatatta ttaggtctat cctatatcaa tcgttttat    2640 aatattgatt ttggagatgc caacatccgt gatattctag cttataatcc aagctcgttc    2700
ggtaaaaaag accttacttc tttagattgg ttaacacacc ttggatctat gagttatgat    2760
gaattaagat taacgaatag tccaaaaaca tttgagaaat actttagtaa aataacgaat    2820
aagactacac tattagattt cctagactac aatagaatga cattcactaa tatggatggc    2880
gatacgtggt tgaagaaagc gactaaagct atcgtagttg aaaaagcttc gaaagaaaaa    2940
accgatgaaa aagtagaatt atatactaaa ttaactactg atcctgaaaa atatggagct    3000
gaaggacttc aaataaataa tagaaaacaa caaaacattg ctacattgtt aggtttggtg    3060
aacattaaag aaccaagcgt gtatgctata actaacatag cgacggtaac ctacggaaac    3120
atcggaacgt atatggatac ttctttagag aaaacaaata aagctaagta taccggagag    3180
cttaataagg ttaaagaatt gatagaatta actgcgacaa gacaggctgc atacgttgat    3240
actttataca gaattacaaa agaagaaaat cgttctaaat tagttacaaa tagagtgatt    3300
gtagacacga tgaaaaaata cacgacggat acgtctgctg gaatagggac aacatggtct    3360
aaagaatcag gaccaacagc agataaaggg gttaaagact ttatgacacc tctaggactg    3420 tattccaccat cgcaaaatgt aggtgcagaa gcgaatggag tgggtgtccg ttacttcata    3480
```

```
gatagagttc tggatgatag aggttcagcg acttactctc acgaaatgac gcacttacta    3540
gatagaacgg tcttgtttaa taatcatggt cgtcgagatg gtacaggagc agagttttat    3600
gcgcgtggta tttttgaaaa ctcctataat ccagaaaagg atacttattt caatctcaac    3660
tttgtatgtg atgagagtga taagaatgga ttttacaata gaacacctga tcgatttaaa    3720
acagcagaag atttgaaatc ttatatgaag ggaagtttcg atgtccttta tactctagat    3780
tatctagaag ctgaggcaag tagaggctta tctacagaag acaaaatgag ttatttcaaa    3840
aaaatagcgc caatcacttc atcaggtcct agaacttggg tagattaccg taatacagcg    3900
gttaaaccga ctcataaaag tgaggaaatt caatctctga ccttagaaga tgccaaaaaa    3960
ttgacagata ttgatagttt gattgacaat catatcctgg tcaatcgtta tatcattgct    4020 ggttttttcag ataaaggaaa aattacagca aatggttatt ataccgttga tatgtttgat    4080
accatttatg gtgttagtca aaatgactct ggtatgagtg gggacatcac ctttagaaaa    4140
caagcctttg aattgatggc tgctttgggc tattatgaag gatttgttcc ttatgtgtca    4200
aatcaataca acaagcagc agaggctgag aacaagcctc tatctgatac ttacattttc    4260
aataaaattt tgaatggtaa gagctatgct gagttcaaaa aagcacagtt caaggaaaga    4320
gtagctaaga ttgatcaatt gaaacctttg acaatccaat atgaaggtca gcaaataagt    4380
ctgacaagtc agaagttaaa agaattgatg cagaaagctg ttcaaggaga gttgaaacag    4440
attaaggcag gcaaaacaac tgcgcgcacc tatacctta ttgaaactcc agttcaaaaa    4500
ctcaaaaaag cgatttataa agcttatctc aaagattcag atgactttag acagtcgatt    4560
tacaatagtt aa                                                         4572
```

<210> SEQ ID NO 15
<211> LENGTH: 3486
<212> TYPE: DNA
<213> ORGANISM: Streptococcus pneumonia

<400> SEQUENCE: 15

```
atgattggat tagctgcacc agacttacca gttattggtg gtggagtcgt tgctgctgat     60
gttattcagg gtggtaacga tataaaagat gtgaacgttc atagtaaatc tgcggaaggt    120
gttgctatga cctataccac ttatgatagc ggaacaagtg gaaaacaaac cgcatcaggt    180
agcggtgtct ttgtagcgcc gaatgtgatg gtaacagtag ctcataacta ctatgataaa    240
aaccaagagg ataagtctgc ggtcttgcgt ggtggggcgt ctgctcgtag ttatgttgtg    300
atgaactcag agacgaaaaa gcacaataaa gtacctactt ctggtgtatc agaaactctt    360
gaaaaagact ctattcattt gtatgatgag aaaaatttg ggaaagacta tatcaacgac    420
ttagcagtag tggtaactaa aaagactgta gaagctatga caggtggtga agattccacca    480 agagaattga gccataaaga ggtttctact ggtgataaaa tctctatggt cggctatcct    540
aatgactttt caactccgaa tttaagtgca gaaaacaaag cacgattgaa agacggtaag    600
gcttattcag ttacaacaac tgtaagtagt gtcaataaag agagtggtac agtcacttat    660
cattcctcag ctttaggagg ttttttcaggt gctcctttgt ttaatgataa gggagaggta    720
gtcggtatcc accaacatgg gacaaatact ccaaacgctc aagaaagtga gcgtattggt    780
ggtggtaccc tctttacgga aaagcacaga gcttggattc gttctatgat tgataaatat    840
ggtataaagg gttggtatat agatggtgca aaccgttact actatgatga aaatcacaga    900
gccttaaaag atgtagagtc tgagattgac ggtgctttgt atcgttttga tgaaaaaggc    960
```

```
cgagctactt tactagaggg tgaagaaaaa ggtcgcgttc tacttcgagt ggaagatact   1020
aaaggaactc ctttgatttc agataaggtt gttcaagaag gttctgttgg aagtggtttg   1080
aattttcatt taagacaaaa tccaaacttc aaacagttaa tagcaacttc tccaacagct   1140
aaagtggtat cctataacgg agtgccaatt aacaaattag caagtgatac aagttggtct   1200
gatgaatatg tcagtaagtt agctttgggt gatacaatta taagagcggt agtagattcg   1260
gtaactcctc catctacgtc ttcttcggat tttgcaagaa ctgaagttgg taaggttgat   1320
ttgagtggta atcgaactt acctgtgcct agtaaagagg tattacaagc tccgaatggt   1380
tcagaaaact tctatgctac aacgcatatt caaacgccag atgggtcggg gtcaggtact   1440
ttaattgcac caaatttggt gttaacagtc gctcataatt tcttaacagt taaaggttct   1500
gaggtagtta cgaagtctgg tcgcaccaat acagtgtata aagctacttt gccaagtggt   1560
cagcctgtga attttccga tgatgatatt gtttattgga caagaaaga ctcagtattt    1620 ggatttaaaa atgacttagc tttggttcgt ttgaaagaaa agcttacagc ggtatctcct   1680
gtagaggtgg tatctgagtc aacttcgatt actaaaggtg acaaagtttc cgtttatggt   1740
tttcctgatg gtcgtttgtc tccagttttg gatagtgaag tagtagctac tactgacttt   1800
ggttcaggta ttgaagggat tagctatggt ggtacaaaac ccggagcttc tggtggtggt   1860
ctttataatg acaaaggttc tttaattgga gttcaccaaa atggtgttgt aggaagccgc   1920
agtggtgggt tagtcttatc aaaagaacaa ttagattggg ttcgttccta tattgagggt   1980
aaacccaaag cccctgttta tgtaacagat aatattttgg tggatgaaaa agacaaggat   2040
aaacttccat caacttcaaa agaagaaaaa ccgaccacac caaagtaga gtcggataaa    2100 gataaaccaa atacacctct aaaaccgcaa gaaaagccga aaacagaggt tataacgagt   2160
tatgagggtg atagtaccct tgaagttggg aaagagcgta cagaggaaac tgagggcgaa   2220
aaagaaggtg tttcccttat ttatcgaacg gtgtataaag gtactaaatc gaaaacagaa   2280
atgtcaccta ttgcctttga cacggtttac caaggagatg aaactaaaga gcttggtttc   2340
cgttcagttt tagagggtaa agagggtcta gttactcgca ctacaagtta ccaagtagat   2400
aagtacacag gagcggtatc ctccaagatt tctgaagaga aaatagcacc tcaatctcaa   2460
gtcatcacat taggtattaa gaaaaatagc agcacaaaag aagttccaat tacagaacgt   2520
tttgaagatt ccgcagaact agagaaaggt aaaactgagg ttatttctga aggttctgta   2580
ggtaaagagg ttactacggt tacttataag gttttacctg atggaaaggt tattgaaaat   2640
tctcgtacag ttgacgttac acccatgaga gagcgtgtag ttcgtaaggg tgtgaaggaa   2700
gtggtatctc cagataaagt agagtctcta gttccaaaag atgcgccgat tagagaagag   2760
cagcctgcgc ttagtgaggg attttcagag tcagatgctt tagtatcagg agaaaaaata   2820
caaggagatc ttgggatact tatagtatct tcagaagaac tagtccctga aagagtagaa   2880
gttccagatt ttgtgactaa agttacaggt ggagaaaaat tgacagtaga agggcaccga   2940
aatgagagta aaataaagac tccatcaaaa caggaaagat catctcgccc agaaaccact   3000
gctcaattca caacgaacgg gacaggttcg tcatcgttaa cagctgtttt tggcggtaaa   3060
acggataaaa tattactttc tactgttgaa cattctgtta ttaaacataa tcaacaagaa   3120
ggatggcata agataaataa tcagtggtat tttagaaatt ctgatgggaa agaacggaca   3180
ggttggatga agaaaaatga tgcatggtat tattttgata cgaatggaac catgcaaact   3240
ggttggctag aggatacaga cggtaattgg tattatctca atgataatgg taggatggag   3300
ataggctggt tccaagattc aagtggcgcg tggtactact taggatcatc tggtcgcatg   3360
```

```
gaatccaata catggattta ttataaagga aagtggtact atattgatgc tttgggtaaa    3420
ctacttttca attcggtaac accagacggc tatagagtga acgagtatgg ggaatggatc    3480
aactga                                                               3486
```

<210> SEQ ID NO 16
<211> LENGTH: 2883
<212> TYPE: DNA
<213> ORGANISM: Streptococcus pneumonia

<400> SEQUENCE: 16

```
ttggagaaag taaagggact ccaaaatgca actgttcatg tggagttcaa accggctgct      60
gatggtccta gttttacaa tctctttct gcttccagta caactaaagt aaatgaatac       120
tttacaatgg caatcaataa tgggacagct tgatagagg acgtggagc tgatggtagc       180 caattttatg gaagttatac agatgcgcct ttgaagatta gaccaggcaa gtataattcg      240
gttactttta ctgttgaaag accaagaaag gatagtccaa atggtcaggt tcgtctttat      300
gtgaatggtg tattatctcg tacgaataaa aagtcaggga aattcctggc agatatgcca      360
gatgtagata aactccagtt aggtgcaact aatagagcag gagaactgaa gtggggctca      420
gatctttcta ttcgtaatct gactgtatac aatcgtgctc taactccaga ggaagtcaaa      480
aaacgtagcc agttgtttga tgtgatagat attgagcctt tacttgctga aggggcagtc      540 tgacagaga agcaagagtt gtttatgagt ggtgtcaatg gtaagccaaa tagtgaggga      600
attaagagtt atcggattcc acctttgcta cgtacggata aggaacatt actggcaggg      660 gcagatcagc gtcgtctcca ccattctgac tggggagata ttgctatggt tgttaggaga      720
agtgaggatg ggggaactac ttggcagcca accttaacct tgaccaacct gcgagacaat      780
ccagaagcaa aagatccgca ggcatcatct tcacttaata tcgatatggt cttggttcaa      840
gatcctacca caaagagaat tttttcaatc tacgatatgt ttccagaggg tcgagctgtc      900
tttggaatgc caaacaaacc tcaaaaagct tatcaacaag ttggagacaa gcactatcaa      960
ttactatata acaaggggga aaatcaagca tatactgttc gagaaaacgg agaagtatat     1020
gatgcaaata atcaaaaaac agattatcgc gttgtagtgg atccaaaaga agaagcctat     1080
agagataagg gcgacctcta taaaagagaa gagcttcttg ggaatatcta ctttgctcaa     1140
tctgctaaaa ctccatttcg tgtagcctat acgagctatt tgtggctttc ctatagtgat     1200
gatgatggga aacttggtc gcaaccaaga gatattacac catcaattcg ccaagattgg     1260
atgaaatttt taggaacagg tccaggtaca ggaattgtgc ttagaacagg agagcacaag     1320
ggacgtatcc tagttcccac ttataccacc aatgctatct cccatctaag cggctcccag     1380
tcttcacgtt tgatttattc agatgatcat ggagaaacat ggcaggctgg agctgctgtt     1440
aatgatgata ggacggtagg cagaaggaaa attcattcct caactatgaa taataggaat     1500
acccaaaata ctgagtcagt tgctgtgcag ttaaataatg gtgatgtgaa actctttatg     1560
agagggttaa cggtgatttt acaggttgcc acaagtaaag atgatgggca aacttgggac     1620
aaggaaatca agagatataa tcaggttaaa gatgtttatg tccaaatggc tgctattcac     1680
accatgcacg aaggaaaaga atatatcatt ttaaccaatt caggaggact aaacggacg     1740 aatggaatgg ctcatttggc tcgtgtagag acaacggag acttgacttg gttacatcat     1800
agaccaattc aaaaaggaga gtttgcctat aattcgcttc aagaattagg aaatggggag     1860
tatggtatct tgtatgaaca tactgaaaaa ggacaaaatg actataccct atcatttaga     1920
```

-continued

```
aaatttaatt gggactttt  aacaaaggat ccggtatatc caacgagtgt aactatcagg    1980
gacgttcgta aattggaaac agaagaagag gatgcagaac aaggcatctt agctatgcaa    2040
tttgattctg aggtactagt gaatgctatt ccgactttga ctttagcgaa tggacacaaa    2100
gctaccttct tgacccaagc agatcaaaaa actctacttt tcacctttaa taaagaagat    2160
gcaggtcaag aaattacagg tctaatggcc ggtagaattg acagtatgca tgatttacca    2220
gttacactag ctggtagtag aattcctgaa gatgcgaaag aaaatcctgt cgagaccatg    2280
aatacagtaa gagaaaatgt atctgaggag atgacagaaa ggaagtcaga gaaggataaa    2340
ttatctttgg agtcttcaga tagaatggta gcaaactctc atcttacttc ttttgctcct    2400
cgttacctcc aatcttatgt aggagatgtt attaaaactg agactaaagt tccaataacg    2460
actggttgga agcaagaaaa tggtgcgtgg tatttttata catctgctgg tgaagtggtg    2520
aaaggctggc atcaggaagc ggataaatgg tactacttga gttctactgg tgcgatggca    2580
actggttggg tcagagatgg taatcaatgg tattatttga gtgagagtgg agcaatgtct    2640
actggctggg ttgaatccag tggtgtgtgg tactatctcc attctaacgg ttcaatggcg    2700
actggttgga taaaagatgg agaccattgg tactatcagg aatcatctgg tgcaatgagg    2760
gtaaatcaat ggttccaagt tggagacaaa tggtactatg tcaatgaaag cggaagatta    2820
gctgttaata ccatagtgga tggttatcaa gttaactcca atggagagtg ggtcaactac    2880
tag                                                                  2883

<210> SEQ ID NO 17
<211> LENGTH: 1068
<212> TYPE: DNA
<213> ORGANISM: Streptococcus pneumonia

<400> SEQUENCE: 17
gccatgtttg actattatca gggttattct aaggaacaaa ttgagctctt ggtgagcttg      60
ccttcctttg gaatcatgat gatgttactg ctaaatggtt tcttagaaaa aatatttcct     120
gagcgcttac agattagttt gggcttgctg atttatcat tgagcggtac agctcccttc     180
tggtaccaag cctatccctt tgtctttgga acacggcttc tctttggttt gggtcttggg    240
atgatcaatg ccaaggccat ttctattatc agtgaacgct accaaggaaa aaggcgaatt    300
cagatgttag ggctacgcgc ttctgcagag gtcgttggag cttctctcat aaccttggcc    360
gtcggtcagt tgttggcctt tggttggaca gctatctttc tagcctatag tgctggattt    420
ttggtgctgc cccttatct gctctttgtc ccttatggaa aatcaaagaa agaagtcaag    480
aaaagagcga aggaagcaag tcgtttaact cgagaaatga aaggcttgat ttttacctta    540
gctatcgaag cggcagttgt agtttgtacc aatacagcta ttaccatccg tattccaagt    600
ttgatggtgg aaagaggatt ggggatgcc cagttatcta gttttgttct tagtatcatg    660
cagttgatcg ggattgtggc tggggtgagt ttttctttct tgatttctat ctttaaagag    720
aaactgctcc tctggtctgg tattacccttt ggcttggggc aaatcgtgat tgccttgtct    780
tcatccttgt gggtggtagt agcaggaagt gttctggctg gatttgccta tagtgtagtc    840
ttgacgacgt tctttcaact tgtctctgaa cgaattccag ctaaactcct caatcaagca    900
acttcatttg ctgtattagg ctgtagtttc ggagcccttta cgaccccatt tgttctaggt    960
gcaattggct tactaactca caatgggatg ttggtcttta tatcttagg aggttggttg    1020 attgtaatct ctatctttgt catgtaccta cttcagaaga gagcttag                1068
```

<210> SEQ ID NO 18
<211> LENGTH: 1188
<212> TYPE: DNA
<213> ORGANISM: Streptococcus pneumonia

<400> SEQUENCE: 18

| | | | | | |
|---|---|---|---|---|---|
| atgaagaaaa | ttgtatttgc | tagcgccttg | gccttgacct | tggcaggagc | agttttgaca | 60 |
| aatgatgttt | ttgcgaatga | cagactggtt | gcaacacaat | ctactgatgg | taatgtattg | 120 |
| acctcagagg | tgctaaaacc | ttctagtggc | aatgttttgg | ttggaatcaa | aggagaattt | 180 |
| ttgcctcctc | atcaacaatc | tattttagat | gccattaata | aaattcgtaa | agaagcagct | 240 |
| gacgaaggtt | tggtagataa | gtatgttcct | gtcaaatggt | cagttgacca | tgagaaaacg | 300 |
| gcttttgtac | gcgctgctga | ggtatccgtt | acgttgaagg | ctgaacgtct | ttccagtaaa | 360 |
| aacaactgga | ctgcatttcc | atctggtaat | agcctaagtg | agaagtcct | agatttgaat | 420 |
| cctgatggat | ttctaaaagc | cattgagaat | tggcatgctg | aaaaggcgaa | ctatgtggcg | 480 |
| aaaaagaaag | ataaaacatc | aaaagaattt | tcattttatt | atgagaactt | gattaaccct | 540 |
| aaatttacct | atgtgggtct | tgctgctttt | aaaaatgcag | ctagtcctca | gaaggcagca | 600 |
| accgttgctt | tggctctagg | aactacgact | tcttcagagg | aattggctgg | tggatatggt | 660 |
| tctgctgttc | agtacacaga | agtgactgcc | tcaaaccttt | caacagttaa | agtaaagca | 720 |
| atggttgtag | aaacaccgtt | gaaagatttc | agaaaatcta | cgtctgatca | gtctggctgg | 780 |
| gtgcagtcta | atggcaagtg | gtatttttat | gagtctggtg | atgtgaagac | aggctggttg | 840 |
| aaaacaggtg | gtaaatggta | ctacttgaat | gaccctaggtg | ttatgcagac | tggatttgta | 900 |
| gaagttgatg | gatcggtgta | ttatctaagt | aactcaggcg | ctatgtttac | aggctgggga | 960 |
| acagatggta | gcagatggtt | ctactgtgat | ggctcagtag | ctatgaaaac | aggctggtac | 1020 |
| aaggaaaatg | gtacatggta | ttaccttgat | gaagaaggga | tcatgaagac | gggttggttt | 1080 |
| aaagtaggtc | aacactggta | ctatgcaaat | ggttcaggcg | ctttggctgt | tagcacaaca | 1140 |
| acaccagatg | gttaccgtgt | aaatgctaat | ggtgaatggg | taagctag | | 1188 |

<210> SEQ ID NO 19
<211> LENGTH: 1848
<212> TYPE: DNA
<213> ORGANISM: Streptococcus pneumonia

<400> SEQUENCE: 19

| | | | | | |
|---|---|---|---|---|---|
| atgtctaaat | caaatcatga | aagaagaatg | cgttattcta | ttcgcaaatt | tagtgtagga | 60 |
| gtggctagtg | tactagtagc | tagcttcttt | atggggagtt | tgctcatgc | aagtgggctt | 120 |
| gtaaaggatg | atagtgttaa | gactacggag | attgcagcta | ctaatagaga | aaaagaaaat | 180 |
| gatgcgaagt | ctggctgggg | aggtatcatt | gatggtagtg | gaaaactatt | gggtggattt | 240 |
| tctgaaataa | aagaaagtt | ggaaaaagag | atagacgaat | ccagtctcac | gtcagagcaa | 300 |
| aagaaatcct | ataaggaaaa | aattgttaag | gtaaacaaa | atgatgtaga | cgggttgttt | 360 |
| ggtgttcaca | gagaatactt | aaaccaacta | gactttcaat | atcttgaact | atccaaagtt | 420 |
| gaggaagagt | ttaaatacca | agaggaacag | atccaaagga | tgttcgagca | aaaaggcatt | 480 |
| acgaatgaag | ataaggatgc | tatgctgaaa | aaaatagcag | aaatccatca | agaggccgaa | 540 |
| aaagatatta | aggcttcagg | aggctatcgt | gataagctaa | atggaacaaa | agttaagttt | 600 |
| cttcagaact | tggacaagct | tttcacctcg | acaaaatcaa | aatttgaaaa | ggaaatgcaa | 660 |
| gagctctatc | gcaagaaaga | ggcagaaatt | gttaaggaaa | agcatttaga | aaaagataag | 720 |

```
atttatgacg atgctgacgt tcaaaaactt cgtgagctag aaaagatgc actgaaaaaa      780 ttggacgagg caaaaacaaa tgatgaagcg ctcagagtga agttggaatt tgctcgaaac      840
gttgagaaaa atagccaaca agtgcaaaaa atagatgata agttgcaaga gttgattaaa      900
gaagccaaac gtgaactgga aaaattaaat caaggaattg cagaagttga taagttacca      960
gaattaccag ctaatgattc tgattatatg gtacagaaaa aatatatctg ggacgaagac     1020
aaagaaacta tacctaaaaa aattgcaaaa tttaaagaga atttgggaaa taaaacgtat     1080
actaaggaat cgttacagaa gtttatagat gattgtattt attaccaaac tcatgcgaaa     1140
atcgaagtca tgactagaaa ggtagctggt tatagaaaag catatcctaa taatccagaa     1200
attgaaaagg aatttgtaag ccatatcaaa caaacaagta gcttaacata tgctagttta     1260
gaaaatgata gcttaaaacg ttattttgaa aaagatttcg ctccggcttt tgagcgaatc     1320
aagcagattg tagaaggact ggagaaacca cacacccccgg cgcaacccgg tattgaaaat     1380
cagaagccat ctgctccaaa aacagagaag tcagctgaac aaccaaaagc aggctggaaa     1440
caagaaaacg gtatgtggta cttctacaat actgatggtt caatggcgac aggatggctc     1500
caaaacaacg gttcatggta ctatctaaac gctaatggtg ctatggcgac aggatggctc     1560
caaaacaatg gttcatggta ctacctcaac gctaacggtt caatggcaac aggatggctc     1620
caaaacaatg gctcatggta ctacctcaac gctaacggtt caatggcaac agattgggtg     1680
aaagatggaa ataccctggta ctatcttgaa gcatcaggtg ctatgaaagc aagccaatgg     1740
ttcaaagtat cagataaatg gtactatgtc aatggcttag gtgcccttgt agtcaacaca     1800
actgtagatg gctatagagt caatgccaat ggtgaatggg taagctaa                  1848
```

<210> SEQ ID NO 20  
<211> LENGTH: 2277  
<212> TYPE: DNA  
<213> ORGANISM: Streptococcus pneumonia
<400> SEQUENCE: 20

```
ttatttctt ctttttcatcg cgattaatga agttccagcc aaaccaagga gaccaatgat       60
ttcaagaact aaattagttg ctgcccctgt ggatggcaaa ttcttctcag ttgctgatgt      120
aggattttct tttgccattg tttcatttcc agtagccagt ggtttatgat taacttcttt      180
attctggaat tttccagttt ggttttctcc tatctgtgtt tgaccatgtt ggacagaagg      240
tttaatctgc ttaggtgtgg tgacattttg attcttagaa agtgtcttaa tcgcaaacaa      300
actgaagtgg ttggttttaa agacaacttg cccattttca actttagaag gaatacgctc      360
aaggtcacca ttttcccttta cgtgatagac gtgaacatct gatgcagtct gcccaagcgc      420
cagcctaaca gttcgttctc cattgacatg agtttccttg cctcctttag ataaagaaag      480
atcaaagatg cgaacagttc ctccaccagt ttggcgagcg attttttcag ccaactcctt      540
cgtcgtcact tcctttatat ttaccttatc agcatcaaca gccttatcaa atacaaccgt      600
aaccttagtt ttcccgtcag aagctgtaat gattttttgaa gttttttgggg tttctggttg      660 tggtttaacc tctggttttg gttttttctgg ttgtggaatc ggcttttcct gtgttggaac      720
agacggtttt tgttctccg gttctttcgg tgtacttggt tgcttaccgt ctggctgtgg      780
gattggttta ggttccggac ttgtactcgg aacttctggc tgaggttgaa ggtctggttt      840
ggtatccggg gctggcattg aaggtttttt atcacctgct tgcgctcttc cactgtctga      900 tttaatttttt tctagggttt taaccttgct cttagctgtt tctaccttgg ctttagcagt      960
attaattttg tcagtatctt gaggtgtttg ggcttgagct tgtgcaagct cgagctctgc     1020
```

```
ctttgcgact tctacttgtg cttccgcaat ttccagttcg attgttttac tagtattggt    1080
tgggtagtta cggcgatctt cttctttttg agccttggct ttttttctcag cctcttcaac   1140
cttcttctga gcttctgcta ccttgtcctg tttcttgagc tctccctgac ttgatttctt    1200
ttctagttcc tcgataatac tgtggatttt gttaaagacc ggtaaaaagt ctctttcaaa    1260
atacgttttc aaggcttccc cctctaaggt agcataagta ctgttagccg tttgttttag    1320
cttttcagaa aatagtcttt caacttcagc cacattagga tgttttttc tatatgtggc     1380
tatctttcta gtcatcgtct caatttgtgc atgaaattga taatagataa attcagcaac    1440
agcatcttt aaagttttt ctgtataggt ctgtttttca agctgttctt tgaatacctg      1500
gattttctta ggcgcagtat ccttactatt atcccaaata tctttttct gcactttgta     1560
atctggatca ttatccggta gctctggata gttattgact tctctgagat agtcctctag    1620
cttttcaat tcttcttggc cttgacgaat caagtcttgt aactttttct tttcagcttc     1680
ggtcgccttt tgtcctggac ttggggaagt tgatggaggt gtttgcgtca ccggtggtac    1740
aaccattgaa ccgcctgctt gtcctcctgg ttggggtacg actccaggtc cttgtcctac    1800
tgaagggtca ccccccccct gtaaaccatc atttagagag agcccttag gagtactttt     1860
actacctgaa cgattttgaa ataactttat ttcttcatct actttttct taacttccct     1920
tcccagctcc tctaccatgc ttttagtaga aactctatca atcttatctc tgtatttatc    1980
tacaaccacc tgaacctttg tgacaatttc tgaaaatcca gaaacagatc gatccagtga    2040
gtctaaacga ctagtcacat agtccgaaat tctttgtta actctttgta cagcatcctc     2100
atattcttt ttatcacctg gagatactat ttgtggaata gggggattag cagaaacatt     2160
ctctgtcgca tgaaccacac ttcccataaa aagactggca acagctacac tagccactcc    2220
tacactaaat ttgcgaatag aataacgcat tcttcttca tgatttgatt tagacat        2277
```

<210> SEQ ID NO 21
<211> LENGTH: 134
<212> TYPE: PRT
<213> ORGANISM: Streptococcus pneumoniae

<400> SEQUENCE: 21

```
Ala Lys Ser Ser Asp Ser Ser Val Gly Glu Glu Thr Leu Pro Ser Pro
1               5                   10                  15

Ser Leu Lys Pro Glu Lys Lys Val Ala Glu Ala Glu Lys Lys Val Glu
            20                  25                  30

Glu Ala Lys Lys Lys Ala Glu Asp Gln Lys Glu Glu Asp Arg Arg Asn
        35                  40                  45

Tyr Pro Thr Asn Thr Tyr Lys Thr Leu Glu Leu Glu Ile Ala Glu Ser
    50                  55                  60

Asp Val Glu Val Lys Lys Ala Glu Leu Glu Leu Val Lys Glu Glu Ala
65                  70                  75                  80

Lys Glu Pro Arg Asn Glu Glu Lys Val Lys Gln Ala Lys Ala Glu Val
                85                  90                  95

Glu Ser Lys Lys Ala Glu Ala Thr Arg Leu Glu Lys Ile Lys Thr Asp
            100                 105                 110

Arg Lys Lys Ala Glu Glu Glu Ala Lys Arg Lys Ala Ala Glu Glu Asp
        115                 120                 125

Lys Val Lys Glu Lys Pro
    130
```

```
<210> SEQ ID NO 22
<211> LENGTH: 134
<212> TYPE: PRT
<213> ORGANISM: Streptococcus pneumoniae

<400> SEQUENCE: 22

Ala Lys Ser Ser Asp Ser Ser Val Gly Glu Glu Thr Leu Pro Ser Ser
1               5                   10                  15

Ser Leu Lys Ser Gly Lys Lys Val Ala Glu Ala Glu Lys Lys Val Glu
            20                  25                  30

Glu Ala Glu Lys Lys Ala Lys Asp Gln Lys Glu Glu Asp Arg Arg Asn
        35                  40                  45

Tyr Pro Thr Asn Thr Tyr Lys Thr Leu Asp Leu Glu Ile Ala Glu Ser
    50                  55                  60

Asp Val Lys Val Lys Glu Ala Glu Leu Glu Leu Val Lys Glu Glu Ala
65                  70                  75                  80

Lys Glu Pro Arg Asp Glu Glu Lys Ile Lys Gln Ala Lys Ala Lys Val
                85                  90                  95

Glu Ser Lys Lys Ala Glu Ala Thr Arg Leu Glu Asn Ile Lys Thr Asp
            100                 105                 110

Arg Lys Lys Ala Glu Glu Ala Lys Arg Lys Ala Ala Glu Glu Asp
        115                 120                 125

Lys Val Lys Glu Lys Pro
    130

<210> SEQ ID NO 23
<211> LENGTH: 125
<212> TYPE: PRT
<213> ORGANISM: Streptococcus pneumoniae

<400> SEQUENCE: 23

Glu Lys Asn Ser Gln Gln Val Gln Lys Ile Asp Asp Lys Leu Gln Glu
1               5                   10                  15

Leu Ile Lys Glu Ala Lys Arg Glu Leu Glu Lys Leu Asn Gln Gly Ile
            20                  25                  30

Ala Glu Val Asp Lys Leu Pro Glu Leu Pro Ala Asn Asp Ser Asp Tyr
        35                  40                  45

Met Val Gln Lys Lys Tyr Ile Trp Asp Glu Lys Glu Thr Ile Pro
    50                  55                  60

Lys Lys Ile Ala Lys Phe Lys Glu Asn Leu Gly Asn Lys Thr Tyr Thr
65                  70                  75                  80

Lys Glu Ser Leu Gln Lys Phe Ile Asp Asp Cys Ile Tyr Tyr Gln Thr
                85                  90                  95

His Ala Lys Ile Glu Val Met Thr Arg Lys Val Ala Gly Tyr Arg Lys
            100                 105                 110

Ala Tyr Pro Asn Asn Pro Glu Ile Glu Lys Glu Phe Val
        115                 120                 125

<210> SEQ ID NO 24
<211> LENGTH: 132
<212> TYPE: PRT
<213> ORGANISM: Streptococcus agalactiae

<400> SEQUENCE: 24

Asp Ser Lys Thr Glu Glu Lys Val Pro Gln Glu Pro Lys Ser Asn Asp
1               5                   10                  15

Lys Asn Gln Leu Gln Glu Leu Ile Lys Ser Ala Gln Gln Glu Leu Glu
            20                  25                  30
```

```
Lys Leu Glu Lys Ala Ile Lys Glu Leu Met Glu Gln Pro Glu Ile Pro
        35                  40                  45

Ser Asn Pro Glu Tyr Gly Ile Gln Lys Ser Ile Trp Glu Ser Gln Lys
 50                  55                  60

Glu Pro Ile Gln Glu Ala Ile Thr Ser Phe Lys Ile Ile Gly Asp
 65                  70                  75                  80

Ser Ser Ser Lys Tyr Tyr Thr Glu His Tyr Phe Asn Lys Tyr Lys Ser
                85                  90                  95

Asp Phe Met Asn Tyr Gln Leu His Ala Gln Met Glu Met Leu Thr Arg
                100                 105                 110

Lys Val Val Gln Tyr Met Asn Lys Tyr Pro Asp Asn Ala Glu Ile Lys
                115                 120                 125

Lys Ile Phe Glu
        130

<210> SEQ ID NO 25
<211> LENGTH: 40
<212> TYPE: PRT
<213> ORGANISM: Streptococcus agalactiae

<400> SEQUENCE: 25

Gln Val Glu Lys Met Ala Glu Gln Lys Gly Ile Thr Asn Glu Asp Lys
 1               5                  10                  15

Asp Ser Met Leu Lys Lys Ile Glu Asp Ile Arg Lys Gln Ala Gln Gln
                20                  25                  30

Ala Asp Lys Lys Glu Asp Ala Glu
        35                  40

<210> SEQ ID NO 26
<211> LENGTH: 40
<212> TYPE: PRT
<213> ORGANISM: Streptococcus pneumoniae

<400> SEQUENCE: 26

Gln Ile Arg Arg Met Gly Glu Gln Lys Gly Ile Thr Asn Glu Asp Lys
 1               5                  10                  15

Asp Ala Met Leu Lys Lys Ile Ala Glu Ile His Gln Glu Ala Glu Lys
                20                  25                  30

Asp Ile Lys Ala Ser Gly Gly Tyr
        35                  40

<210> SEQ ID NO 27
<211> LENGTH: 40
<212> TYPE: PRT
<213> ORGANISM: Streptococcus pneumoniae

<400> SEQUENCE: 27

Lys Asp Gln Lys Glu Glu Asp Arg Arg Asn Tyr Pro Thr Ile Thr Tyr
 1               5                  10                  15

Lys Thr Leu Glu Leu Glu Ile Ala Glu Ser Asp Val Glu Val Lys Lys
                20                  25                  30

Ala Glu Leu Glu Leu Val Lys Val
        35                  40

<210> SEQ ID NO 28
<211> LENGTH: 40
<212> TYPE: PRT
<213> ORGANISM: Streptococcus pneumoniae
```

```
<400> SEQUENCE: 28

Glu Asp Gln Lys Glu Glu Asp Arg Arg Asn Tyr Pro Thr Asn Thr Tyr
1               5                   10                  15

Lys Thr Leu Glu Leu Glu Ile Ala Glu Phe Asp Val Lys Val Lys Glu
                20              25                  30

Ala Glu Leu Glu Leu Val Lys Glu
            35              40
```

UNITED STATES PATENT AND TRADEMARK OFFICE
CERTIFICATE OF CORRECTION

PATENT NO.      : 10,420,826 B2                                       Page 1 of 1
APPLICATION NO. : 15/524576
DATED           : September 24, 2019
INVENTOR(S)     : Michael Valentino and Michael S. Gilmore It is certified that error appears in the above-identified patent and that said Letters Patent is hereby corrected as shown below:

In the Claims

In Column 133, Line 21, Claim 1, delete "(SE" and insert -- (SEQ --

Signed and Sealed this
Sixteenth Day of June, 2020

Andrei Iancu
*Director of the United States Patent and Trademark Office*